(12) United States Patent
Pollard et al.

(10) Patent No.: US 11,464,774 B2
(45) Date of Patent: Oct. 11, 2022

(54) METHOD FOR TREATING CANCER USING A COMBINATION OF DNA DAMAGING AGENTS AND ATR INHIBITORS

(71) Applicant: VERTEX PHARMACEUTICALS INCORPORATED, Boston, MA (US)

(72) Inventors: John Robert Pollard, Abingdon (GB); Peter Littlewood, Abingdon (GB); Philip Michael Reaper, Abingdon (GB); Mohammed Asmal, Newton, MA (US); Scott Zachary Fields, Towaco, NJ (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 15/763,366

(22) PCT Filed: Sep. 30, 2016

(86) PCT No.: PCT/US2016/054996
§ 371 (c)(1),
(2) Date: Mar. 26, 2018

(87) PCT Pub. No.: WO2017/059357
PCT Pub. Date: Apr. 6, 2017

(65) Prior Publication Data
US 2018/0303829 A1 Oct. 25, 2018

Related U.S. Application Data

(60) Provisional application No. 62/345,191, filed on Jun. 3, 2016, provisional application No. 62/323,055, filed (Continued)

(51) Int. Cl.
*A61K 31/497* (2006.01)
*A61K 33/243* (2019.01)
(Continued)

(52) U.S. Cl.
CPC .......... *A61K 31/497* (2013.01); *A61K 31/282* (2013.01); *A61K 31/4965* (2013.01);
(Continued)

(58) Field of Classification Search
CPC ................ A61K 31/497; A61K 31/282; A61K 31/7068; A61P 35/00
See application file for complete search history.

(56) References Cited

U.S. PATENT DOCUMENTS

| 4,309,430 A | 1/1982 | Bock et al. |
| 5,143,824 A | 9/1992 | Yamakawa et al. |

(Continued)

FOREIGN PATENT DOCUMENTS

| CN | 1551869 | 12/2004 |
| CN | 101001606 | 7/2007 |

(Continued)

OTHER PUBLICATIONS

Huntoon et al. ATR Inhibition broadly sensitzes ovarian cancer cells to chemotherapy independent on BRCA status. Cancer Res., 73(12); 3683-91.*

(Continued)

*Primary Examiner* — Theodore R. Howell
(74) *Attorney, Agent, or Firm* — Dechert LLP; Andrea L.C. Reid; Danielle M. Nihan

(57) ABSTRACT

Described herein are methods of treating a proliferative disorder (e.g., cancer) in a patient by administering a DNA damaging agent and between about 12 and about 48 hours later administering to the subject a compound that inhibits ATR protein kinase. Methods of treating a proliferative disorder (e.g., cancer) in a patient by administering a compound that inhibits ATR protein kinase are also described. Exemplary ATR inhibitors are represented by Formulae A-I (Continued)

Optimization of Compound A-2 Dose Schedule In Vitro and A-II or a pharmaceutically acceptable salt thereof, wherein the variables are as defined herein.

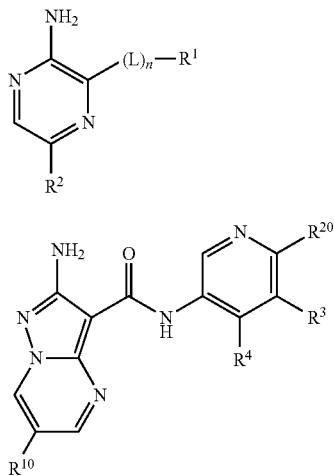

14 Claims, 17 Drawing Sheets

Related U.S. Application Data on Apr. 15, 2016, provisional application No. 62/303,153, filed on Mar. 3, 2016, provisional application No. 62/287,136, filed on Jan. 26, 2016, provisional application No. 62/251,640, filed on Nov. 5, 2015, provisional application No. 62/235,393, filed on Sep. 30, 2015.

(51) Int. Cl.
| | |
|---|---|
| A61P 35/00 | (2006.01) |
| A61K 45/06 | (2006.01) |
| A61K 31/7068 | (2006.01) |
| A61K 31/4965 | (2006.01) |
| A61K 31/555 | (2006.01) |
| A61K 31/519 | (2006.01) |
| A61K 31/282 | (2006.01) |
| A61N 5/10 | (2006.01) |

(52) U.S. Cl.
CPC .......... *A61K 31/519* (2013.01); *A61K 31/555* (2013.01); *A61K 31/7068* (2013.01); *A61K 33/243* (2019.01); *A61K 45/06* (2013.01); *A61N 5/10* (2013.01); *A61P 35/00* (2018.01)

(56) References Cited

U.S. PATENT DOCUMENTS

| | | | |
|---|---|---|---|
| 5,902,773 A | 5/1999 | Benoit et al. | |
| 6,060,478 A | 5/2000 | Gilligan et al. | |
| 6,191,131 B1 | 2/2001 | He et al. | |
| 6,235,741 B1 | 5/2001 | Bilodeau et al. | |
| 6,420,637 B1 | 7/2002 | Ueda et al. | |
| 6,469,002 B1 | 10/2002 | Ohshima et al. | |
| 6,495,541 B1 | 12/2002 | Webber et al. | |
| 6,605,617 B2 | 8/2003 | Renhowe et al. | |
| 6,660,753 B2 | 12/2003 | Van Wagenen et al. | |
| 6,762,194 B2 | 7/2004 | Renhowe et al. | |
| 6,774,237 B2 | 8/2004 | Renhowe et al. | |
| 6,790,935 B1 | 9/2004 | Mutter et al. | |
| 6,800,760 B2 | 10/2004 | Renhowe et al. | |
| 6,858,600 B2 | 2/2005 | Hamilton et al. | |
| 6,967,198 B2 | 11/2005 | Benedict et al. | |
| 6,992,087 B2 | 1/2006 | Verhoest et al. | |
| 7,041,672 B2 | 5/2006 | Verhoest et al. | |
| 7,043,079 B2 | 5/2006 | Malvar et al. | |
| 7,132,533 B2 | 11/2006 | Benedict et al. | |
| 7,145,002 B2 | 12/2006 | Brands et al. | |
| 7,199,123 B2 | 4/2007 | Munchhof | |
| 7,277,118 B2 | 10/2007 | Foote | |
| 7,385,626 B2 | 6/2008 | Aggarwal et al. | |
| 7,394,926 B2 | 7/2008 | Bryll et al. | |
| 7,429,578 B2 | 9/2008 | Webber et al. | |
| 7,449,464 B2 | 11/2008 | Martin et al. | |
| 7,452,993 B2 | 11/2008 | Arnold et al. | |
| 7,462,713 B2 | 12/2008 | Benedict et al. | |
| 7,528,138 B2 | 5/2009 | Knegtel et al. | |
| 7,550,470 B2 | 6/2009 | Fraley | |
| 7,550,603 B2 | 6/2009 | Zhu et al. | |
| 7,574,131 B2 | 8/2009 | Chang et al. | |
| 7,622,583 B2 | 11/2009 | Ungashe et al. | |
| 7,626,021 B2 | 12/2009 | Arnold et al. | |
| 7,700,601 B2 | 4/2010 | Chan et al. | |
| 7,704,995 B2 | 4/2010 | Buhr et al. | |
| 7,829,558 B2 | 11/2010 | Arnold et al. | |
| 7,872,031 B2 | 1/2011 | Lauffer et al. | |
| 7,902,197 B2 | 3/2011 | Elworthy et al. | |
| 7,932,254 B2 | 4/2011 | DuBois et al. | |
| 7,939,531 B2 | 5/2011 | Bamberg et al. | |
| 7,981,893 B2 | 7/2011 | Mortensen et al. | |
| 8,012,976 B2 | 9/2011 | Wang et al. | |
| 8,063,032 B2 | 11/2011 | Chytil et al. | |
| 8,071,623 B2 | 12/2011 | Jones et al. | |
| 8,093,244 B2 | 1/2012 | Diaz et al. | |
| 8,106,197 B2 | 1/2012 | Cui et al. | |
| 8,143,241 B2 | 3/2012 | Ashworth et al. | |
| 8,211,854 B2 | 7/2012 | Guzi et al. | |
| 8,247,416 B2 | 8/2012 | Menear et al. | |
| 8,252,802 B2 | 8/2012 | Foote et al. | |
| 8,410,112 B2 | 4/2013 | Charrier et al. | |
| 8,420,650 B2 | 4/2013 | Wang et al. | |
| 8,436,185 B2 | 5/2013 | Foley et al. | |
| 8,492,582 B2 | 7/2013 | Yokotani et al. | |
| 8,623,869 B2 | 1/2014 | Charrier et al. | |
| 8,765,751 B2 | 7/2014 | Charrier et al. | |
| 8,822,469 B2 | 9/2014 | MacCormick et al. | |
| 8,841,308 B2* | 9/2014 | Charrier ............... | C07D 401/14 |
| | | | 514/255.06 |
| 8,841,337 B2 | 9/2014 | Charrier et al. | |
| 8,841,449 B2 | 9/2014 | Charrier et al. | |
| 8,841,450 B2 | 9/2014 | Charrier et al. | |
| 8,846,686 B2 | 9/2014 | Charrier et al. | |
| 8,846,917 B2 | 9/2014 | Charrier et al. | |
| 8,846,918 B2 | 9/2014 | Charrier et al. | |
| 8,853,217 B2 | 10/2014 | Charrier et al. | |
| 8,877,759 B2 | 11/2014 | Charrier et al. | |
| 8,912,198 B2 | 12/2014 | Charrier et al. | |
| 8,957,078 B2 | 2/2015 | Brenchley et al. | |
| 8,962,631 B2 | 2/2015 | Charrier et al. | |
| 8,969,356 B2 | 3/2015 | Charrier et al. | |
| 8,969,360 B2 | 3/2015 | Charrier et al. | |
| 8,999,632 B2 | 4/2015 | Falcon et al. | |
| 9,035,053 B2 | 5/2015 | Charrier et al. | |
| 9,062,008 B2 | 6/2015 | Charrier et al. | |
| 9,096,584 B2 | 8/2015 | Charrier et al. | |
| 9,096,602 B2 | 8/2015 | Everitt et al. | |
| 9,309,250 B2 | 3/2016 | Storck et al. | |
| 9,334,244 B2 | 5/2016 | Charrier et al. | |
| 9,340,546 B2 | 5/2016 | Ahmad et al. | |
| 9,365,557 B2 | 6/2016 | Charrier et al. | |
| 9,650,381 B2 | 5/2017 | Ahmad et al. | |
| 9,670,215 B2 | 6/2017 | Ahmad et al. | |
| 9,701,674 B2 | 7/2017 | Charrier et al. | |
| 9,718,827 B2 | 8/2017 | Ahmad et al. | |
| 9,791,456 B2 | 10/2017 | Falcon et al. | |
| 9,862,709 B2 | 1/2018 | Charrier et al. | |
| 10,093,676 B2 | 10/2018 | Ahmad et al. | |
| 10,160,760 B2 | 12/2018 | Charrier et al. | |

(56) References Cited

U.S. PATENT DOCUMENTS

| | | |
|---|---|---|
| 10,208,027 B2 | 2/2019 | Charrier et al. |
| 10,392,391 B2 | 8/2019 | Ahmad et al. |
| 10,478,430 B2 * | 11/2019 | Pollard ............... C07D 413/04 |
| 10,479,784 B2 | 11/2019 | Charrier et al. |
| 10,787,452 B2 | 9/2020 | Ahmad et al. |
| 10,800,781 B2 | 10/2020 | Ahmad et al. |
| 10,813,929 B2 | 10/2020 | Pollard et al. |
| 10,815,239 B2 | 10/2020 | Charrier et al. |
| 10,822,331 B2 | 11/2020 | Charrier et al. |
| 10,961,232 B2 | 3/2021 | Charrier et al. |
| 11,110,086 B2 | 9/2021 | Pollard et al. |
| 11,117,900 B2 | 9/2021 | Ahmad et al. |
| 11,179,394 B2 | 11/2021 | Helleday et al. |
| 2002/0041880 A1 | 4/2002 | Canella et al. |
| 2002/0064314 A1 | 5/2002 | Comaniciu et al. |
| 2002/0068828 A1 | 6/2002 | Schnatterer et al. |
| 2002/0158984 A1 | 10/2002 | Brodsky et al. |
| 2002/0180759 A1 | 12/2002 | Park et al. |
| 2002/0195563 A1 | 12/2002 | Lida et al. |
| 2003/0008882 A1 | 1/2003 | Hamilton et al. |
| 2003/0028018 A1 | 2/2003 | Renhowe et al. |
| 2003/0055085 A1 | 3/2003 | Wagenen et al. |
| 2003/0199511 A1 | 10/2003 | Li et al. |
| 2004/0034037 A1 | 2/2004 | Harbeson et al. |
| 2004/0043998 A1 | 3/2004 | Kato et al. |
| 2004/0075741 A1 | 4/2004 | Berkey et al. |
| 2004/0100560 A1 | 5/2004 | Stavely et al. |
| 2004/0175042 A1 | 9/2004 | Kroeker et al. |
| 2004/0180905 A1 | 9/2004 | Munchhof |
| 2004/0202382 A1 | 10/2004 | Pilu |
| 2004/0252193 A1 | 12/2004 | Higgins |
| 2004/0264793 A1 | 12/2004 | Okubo |
| 2005/0116968 A1 | 6/2005 | Barr et al. |
| 2005/0123902 A1 | 6/2005 | Meneses et al. |
| 2005/0207487 A1 | 9/2005 | Monroe |
| 2005/0261339 A1 | 11/2005 | Ohi et al. |
| 2005/0276765 A1 | 12/2005 | Nghiem et al. |
| 2006/0046991 A1 | 3/2006 | Cui et al. |
| 2006/0083440 A1 | 4/2006 | Chen |
| 2006/0142307 A1 | 6/2006 | Hellberg et al. |
| 2006/0156482 A1 | 7/2006 | Lim et al. |
| 2006/0211709 A1 | 9/2006 | Buhr et al. |
| 2007/0010556 A1 | 1/2007 | Ashwell et al. |
| 2007/0032501 A1 | 2/2007 | Augeri et al. |
| 2007/0037794 A1 | 2/2007 | Ungashe et al. |
| 2007/0082900 A1 | 4/2007 | Guzi et al. |
| 2007/0092245 A1 | 4/2007 | Bazakos et al. |
| 2007/0112006 A1 | 5/2007 | Schiemann et al. |
| 2007/0120954 A1 | 5/2007 | Allen et al. |
| 2007/0149547 A1 | 6/2007 | Bonnefo et al. |
| 2007/0197389 A1 | 8/2007 | Schwogler et al. |
| 2007/0254868 A1 | 11/2007 | Lauffer et al. |
| 2007/0270420 A1 | 11/2007 | Harbeson et al. |
| 2007/0287711 A1 | 12/2007 | Arnold et al. |
| 2008/0132698 A1 | 6/2008 | Fagnou et al. |
| 2008/0176892 A1 | 7/2008 | Heinrich et al. |
| 2008/0287463 A1 | 11/2008 | Herrmann et al. |
| 2009/0001843 A1 | 1/2009 | Enomoto et al. |
| 2009/0005381 A1 | 1/2009 | Brown et al. |
| 2009/0143410 A1 | 6/2009 | Patel |
| 2009/0156512 A1 | 6/2009 | Umemura et al. |
| 2009/0215724 A1 | 8/2009 | DuBois et al. |
| 2009/0215750 A1 | 8/2009 | Bamberg et al. |
| 2009/0215785 A1 | 8/2009 | DuBois et al. |
| 2009/0215788 A1 | 8/2009 | Elworthy et al. |
| 2009/0306087 A1 | 12/2009 | Ibrahim et al. |
| 2009/0318436 A1 | 12/2009 | Albrecht et al. |
| 2010/0036118 A1 | 2/2010 | Arnold et al. |
| 2010/0167931 A1 | 7/2010 | Mueller et al. |
| 2010/0168138 A1 | 7/2010 | DeGoey et al. |
| 2010/0179194 A1 | 7/2010 | Mihara et al. |
| 2010/0190980 A1 | 7/2010 | Umemiya et al. |
| 2010/0204214 A1 | 8/2010 | Chytil et al. |
| 2010/0222318 A1 | 9/2010 | Charrier et al. |
| 2010/0233091 A1 | 9/2010 | Neumann et al. |
| 2010/0249112 A1 | 9/2010 | O'Connor |
| 2010/0249387 A1 | 9/2010 | Inouye |
| 2011/0015231 A1 | 1/2011 | Al-Abed et al. |
| 2011/0053923 A1 | 3/2011 | Foote et al. |
| 2011/0059936 A1 | 3/2011 | Lauffer et al. |
| 2011/0098325 A1 | 4/2011 | Raynham et al. |
| 2011/0112144 A1 | 5/2011 | Ball et al. |
| 2011/0275797 A1 | 11/2011 | Yokotani et al. |
| 2011/0288067 A1 | 11/2011 | Hendricks et al. |
| 2012/0025805 A1 | 2/2012 | Matshita et al. |
| 2012/0027874 A1 | 2/2012 | Charrier et al. |
| 2012/0035407 A1 | 2/2012 | Charrier et al. |
| 2012/0035408 A1 | 2/2012 | Charrier et al. |
| 2012/0040020 A1 | 2/2012 | Charrier et al. |
| 2012/0046295 A1 | 2/2012 | Charrier et al. |
| 2012/0065247 A1 | 3/2012 | Thompson et al. |
| 2012/0122884 A1 | 5/2012 | Charrier et al. |
| 2012/0177748 A1 | 7/2012 | Charrier et al. |
| 2012/0178756 A1 | 7/2012 | Charrier et al. |
| 2012/0178915 A1 | 7/2012 | Xu |
| 2012/0220587 A1 | 8/2012 | Emde et al. |
| 2012/0225857 A1 | 9/2012 | Augeri et al. |
| 2012/0238518 A1 | 9/2012 | Maciag |
| 2013/0017273 A1 | 1/2013 | Everitt et al. |
| 2013/0018035 A1 | 1/2013 | MacCormick et al. |
| 2013/0034616 A1 | 2/2013 | Storck et al. |
| 2013/0089624 A1 | 4/2013 | Charrier et al. |
| 2013/0089625 A1 | 4/2013 | Charrier et al. |
| 2013/0089626 A1 | 4/2013 | Pollard et al. |
| 2013/0095193 A1 | 4/2013 | Charrier et al. |
| 2013/0096139 A1 | 4/2013 | Charrier et al. |
| 2013/0115310 A1 | 5/2013 | Charrier et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0115314 A1 | 5/2013 | Charrier et al. |
| 2013/0172273 A1 | 7/2013 | Aizpurua Iparraguirre et al. |
| 2013/0184292 A1 | 7/2013 | Charrier et al. |
| 2014/0044802 A1 * | 2/2014 | Pollard ............... A61K 31/4965 424/649 |
| 2014/0100229 A1 | 4/2014 | Follmann et al. |
| 2014/0107093 A1 | 4/2014 | Charrier et al. |
| 2014/0113005 A1 | 4/2014 | Charrier et al. |
| 2014/0134596 A1 * | 5/2014 | Falcon ............... G01N 33/5047 435/2 |
| 2014/0163000 A1 | 6/2014 | Ahmad |
| 2014/0187529 A1 | 7/2014 | Shetty et al. |
| 2014/0249157 A1 | 9/2014 | Ahmad et al. |
| 2014/0275009 A1 | 9/2014 | Brenchley et al. |
| 2014/0275021 A1 | 9/2014 | Charrier et al. |
| 2014/0275130 A1 | 9/2014 | Charrier et al. |
| 2014/0288347 A1 | 9/2014 | Charrier et al. |
| 2014/0356456 A1 | 12/2014 | Pollard et al. |
| 2015/0031661 A1 | 1/2015 | Charrier et al. |
| 2015/0051187 A1 | 2/2015 | Charrier et al. |
| 2015/0158868 A1 | 6/2015 | Boyall et al. |
| 2015/0158872 A1 | 6/2015 | Charrier et al. |
| 2015/0216175 A1 | 8/2015 | Heil et al. |
| 2015/0239874 A1 | 8/2015 | Charrier et al. |
| 2015/0247866 A1 | 9/2015 | Falcon et al. |
| 2015/0274710 A1 | 10/2015 | Charrier et al. |
| 2015/0291601 A1 | 10/2015 | Brenchley et al. |
| 2015/0299205 A1 | 10/2015 | Charrier et al. |
| 2015/0353560 A1 | 12/2015 | Ahmad et al. |
| 2015/0359797 A1 | 12/2015 | Helleday et al. |
| 2015/0376187 A1 | 12/2015 | Everitt et al. |
| 2016/0009723 A1 | 1/2016 | Charrier et al. |
| 2016/0030424 A1 | 2/2016 | Pollard et al. |
| 2016/0271129 A1 | 9/2016 | Charrier et al. |
| 2016/0311809 A1 | 10/2016 | Charrier et al. |
| 2016/0326180 A1 | 11/2016 | Boyall et al. |
| 2016/0347754 A1 | 12/2016 | Ahmad et al. |
| 2017/0349596 A1 | 12/2017 | Ahmad et al. |
| 2018/0072735 A1 | 3/2018 | Ahmad et al. |
| 2018/0155346 A1 | 6/2018 | Ahmad et al. |
| 2018/0170922 A1 | 6/2018 | Charrier et al. |
| 2019/0047995 A1 | 2/2019 | Charrier et al. |
| 2020/0140441 A1 | 5/2020 | Ahmad et al. |
| 2020/0222392 A1 | 7/2020 | Pollard et al. |

(56) References Cited

U.S. PATENT DOCUMENTS

| | | |
|---|---|---|
| 2020/0390761 A1 | 12/2020 | Pollard et al. |
| 2021/0032255 A1 | 2/2021 | Charrier et al. |
| 2021/0047333 A1 | 2/2021 | Ahmad et al. |

FOREIGN PATENT DOCUMENTS

| | | |
|---|---|---|
| CN | 101479255 | 7/2009 |
| CN | 101537007 | 9/2009 |
| CN | 101652354 | 2/2010 |
| CN | 101671336 | 3/2010 |
| CN | 103373996 | 10/2013 |
| EP | 313724 | 5/1989 |
| EP | 1217000 | 6/2002 |
| EP | 2157090 | 2/2010 |
| JP | 62270623 | 11/1987 |
| JP | S-62270623 | 11/1987 |
| JP | 63208520 | 8/1988 |
| JP | S-63208520 | 8/1988 |
| JP | H-0272370 | 3/1990 |
| JP | H-0272372 | 3/1990 |
| JP | H-0374370 | 3/1991 |
| JP | H-1077286 | 3/1998 |
| JP | 2001302666 | 10/2001 |
| JP | 2002072370 | 3/2002 |
| JP | 2002072372 | 3/2002 |
| JP | 2002518389 | 6/2002 |
| JP | 2003074370 | 3/2003 |
| JP | 2003516974 | 5/2003 |
| JP | 2005511531 | 4/2005 |
| JP | 2005530760 | 10/2005 |
| JP | 2006156445 | 6/2006 |
| JP | 2006516124 | 6/2006 |
| JP | 2006519232 | 8/2006 |
| JP | 2006519833 | 8/2006 |
| JP | 2006520794 | 9/2006 |
| JP | 2006521357 | 9/2006 |
| JP | 2006526031 | 11/2006 |
| JP | 2007524682 | 8/2007 |
| JP | 2008510790 | 4/2008 |
| JP | 2008510792 | 4/2008 |
| JP | 2008517945 | 5/2008 |
| JP | 2008525453 | 7/2008 |
| JP | 2008543754 | 12/2008 |
| JP | 2009503103 | 1/2009 |
| JP | 2009027904 | 2/2009 |
| JP | 2009530233 | 8/2009 |
| JP | 2009532356 | 9/2009 |
| JP | 2009533327 | 9/2009 |
| JP | 2009541247 | 11/2009 |
| JP | 2009541268 | 11/2009 |
| JP | 2010506934 | 3/2010 |
| JP | 2010509356 | 3/2010 |
| JP | 2010077286 | 4/2010 |
| JP | 2010513433 | 4/2010 |
| JP | 2010180180 | 8/2010 |
| JP | 2011500778 | 1/2011 |
| JP | 2011042639 | 3/2011 |
| JP | 2012508260 | 4/2012 |
| JP | 2012513398 | 6/2012 |
| JP | 2012533248 | 12/2012 |
| JP | 2013501720 | 1/2013 |
| JP | 2013505900 | 2/2013 |
| JP | 2013517264 | 5/2013 |
| JP | 2013525476 | 6/2013 |
| JP | 2014510072 | 4/2014 |
| JP | 2014518545 | 7/2014 |
| JP | 2014165380 | 9/2014 |
| NZ | 593316 | 6/2013 |
| NZ | 593969 | 11/2013 |
| RU | 2010129928 | 1/2012 |
| WO | WO-1996035690 | 11/1996 |
| WO | WO-1997043267 | 11/1997 |
| WO | WO-1998003510 | 1/1998 |
| WO | WO-1998033799 | 8/1998 |
| WO | WO-1998042701 | 10/1998 |
| WO | WO-1998054093 | 12/1998 |
| WO | WO-1999044609 | 9/1999 |
| WO | WO-2000004014 | 1/2000 |
| WO | WO-2000053605 | 9/2000 |
| WO | WO-2000076982 | 12/2000 |
| WO | WO-2001040231 | 6/2001 |
| WO | WO-2001044206 | 6/2001 |
| WO | WO-2001068612 | 9/2001 |
| WO | WO-2001092257 | 12/2001 |
| WO | WO-2002009648 | 2/2002 |
| WO | WO-2002040485 | 5/2002 |
| WO | WO-2002066481 | 8/2002 |
| WO | WO-2002080899 | 10/2002 |
| WO | WO-2003000187 | 1/2003 |
| WO | WO-2003004472 | 1/2003 |
| WO | WO-2003004475 | 1/2003 |
| WO | WO-2003032971 | 4/2003 |
| WO | WO-2003037900 | 5/2003 |
| WO | WO-2003045924 | 6/2003 |
| WO | WO-2003076422 | 9/2003 |
| WO | WO-2003080610 | 10/2003 |
| WO | WO-2003087057 | 10/2003 |
| WO | WO-2003091256 | 11/2003 |
| WO | WO-2003092686 | 11/2003 |
| WO | WO-2003093297 | 11/2003 |
| WO | WO-2003101968 | 12/2003 |
| WO | WO-2003101993 | 12/2003 |
| WO | WO-2004000318 | 12/2003 |
| WO | WO-2004000820 | 12/2003 |
| WO | WO-2004022559 | 3/2004 |
| WO | WO-2004022560 | 3/2004 |
| WO | WO-2004022561 | 3/2004 |
| WO | WO-2004026229 | 4/2004 |
| WO | WO-2004033431 | 4/2004 |
| WO | WO-2004052315 | 6/2004 |
| WO | WO-2004055005 | 7/2004 |
| WO | WO-2004055006 | 7/2004 |
| WO | WO-2004076412 | 9/2004 |
| WO | WO-2004076458 | 9/2004 |
| WO | WO-2004080982 | 9/2004 |
| WO | WO-2004084813 | 10/2004 |
| WO | WO-2004084824 | 10/2004 |
| WO | WO-2004085409 | 10/2004 |
| WO | WO-2004103279 | 12/2004 |
| WO | WO-2004103369 | 12/2004 |
| WO | WO-2004103991 | 12/2004 |
| WO | WO-2005028434 | 3/2005 |
| WO | WO-2005028475 | 3/2005 |
| WO | WO-2005051906 | 6/2005 |
| WO | WO-2005054246 | 6/2005 |
| WO | WO-2005058876 | 6/2005 |
| WO | WO-2005077954 | 8/2005 |
| WO | WO-2005079802 | 9/2005 |
| WO | WO-2005080396 | 9/2005 |
| WO | WO-2005117909 | 12/2005 |
| WO | WO-2005123672 | 12/2005 |
| WO | WO-2006015124 | 2/2006 |
| WO | WO-2006021886 | 3/2006 |
| WO | WO-2006047504 | 5/2006 |
| WO | WO-2006052913 | 5/2006 |
| WO | WO-2006053342 | 5/2006 |
| WO | WO-2006058074 | 6/2006 |
| WO | WO-2006067462 | 6/2006 |
| WO | WO-2006071548 | 7/2006 |
| WO | WO-2006071752 | 7/2006 |
| WO | WO-2006075152 | 7/2006 |
| WO | WO-2006087120 | 8/2006 |
| WO | WO-2006088837 | 8/2006 |
| WO | WO-2006114180 | 11/2006 |
| WO | WO-2006120573 | 11/2006 |
| WO | WO-2006124874 | 11/2006 |
| WO | WO-2006128184 | 11/2006 |
| WO | WO-2006135604 | 12/2006 |
| WO | WO-2007015632 | 2/2007 |
| WO | WO-2007016674 | 2/2007 |
| WO | WO-2007041712 | 4/2007 |
| WO | WO-2007044401 | 4/2007 |
| WO | WO-2007044407 | 4/2007 |
| WO | WO-2007044410 | 4/2007 |

(56) References Cited

FOREIGN PATENT DOCUMENTS

| | | |
|---|---|---|
| WO | WO-2007044420 | 4/2007 |
| WO | WO-2007044426 | 4/2007 |
| WO | WO-2007044441 | 4/2007 |
| WO | WO-2007044449 | 4/2007 |
| WO | WO-2007046548 | 4/2007 |
| WO | WO-2007048066 | 4/2007 |
| WO | WO-2007058850 | 5/2007 |
| WO | WO-2007063012 | 6/2007 |
| WO | WO-2007066805 | 6/2007 |
| WO | WO-2007076360 | 7/2007 |
| WO | WO-2007095588 | 8/2007 |
| WO | WO-2007096151 | 8/2007 |
| WO | WO-2007096764 | 8/2007 |
| WO | WO-2007096765 | 8/2007 |
| WO | WO-2007102770 | 9/2007 |
| WO | WO-2007111904 | 10/2007 |
| WO | WO-2007126841 | 11/2007 |
| WO | WO-2007126964 | 11/2007 |
| WO | WO-2007139732 | 12/2007 |
| WO | WO-2007139856 | 12/2007 |
| WO | WO-2007139860 | 12/2007 |
| WO | WO-2007147746 | 12/2007 |
| WO | WO-2007147874 | 12/2007 |
| WO | WO-2008004698 | 1/2008 |
| WO | WO-2008008539 | 1/2008 |
| WO | WO-2008025820 | 3/2008 |
| WO | WO-2008037477 | 4/2008 |
| WO | WO-2008038010 | 4/2008 |
| WO | WO-2008040651 | 4/2008 |
| WO | WO-2008045266 | 4/2008 |
| WO | WO-2008045268 | 4/2008 |
| WO | WO-2008051493 | 5/2008 |
| WO | WO-2008060907 | 5/2008 |
| WO | WO-2008063671 | 5/2008 |
| WO | WO-2008071456 | 6/2008 |
| WO | WO-2008074997 | 6/2008 |
| WO | WO-2008079291 | 7/2008 |
| WO | WO-2008079903 | 7/2008 |
| WO | WO-2008079906 | 7/2008 |
| WO | WO-2008103277 | 8/2008 |
| WO | WO-2008106692 | 9/2008 |
| WO | WO-2008122375 | 10/2008 |
| WO | WO-2008124850 | 10/2008 |
| WO | WO-2008130569 | 10/2008 |
| WO | WO-2008130570 | 10/2008 |
| WO | WO-2008141065 | 11/2008 |
| WO | WO-2008144463 | 11/2008 |
| WO | WO-2008144464 | 11/2008 |
| WO | WO-2008151735 | 12/2008 |
| WO | WO-2008156174 | 12/2008 |
| WO | WO-2008157191 | 12/2008 |
| WO | WO-2009005638 | 1/2009 |
| WO | WO-2009006580 | 1/2009 |
| WO | WO-2009007390 | 1/2009 |
| WO | WO-2009012482 | 1/2009 |
| WO | WO-2009014637 | 1/2009 |
| WO | WO-2010002483 | 1/2009 |
| WO | WO-2010006086 | 1/2009 |
| WO | WO-2009016460 | 2/2009 |
| WO | WO-2009017954 | 2/2009 |
| WO | WO-2009024825 | 2/2009 |
| WO | WO-2009037247 | 3/2009 |
| WO | WO-2009053737 | 4/2009 |
| WO | WO-2009070567 | 6/2009 |
| WO | WO-2009075790 | 6/2009 |
| WO | WO-2009088986 | 7/2009 |
| WO | WO-2009091374 | 7/2009 |
| WO | WO-2009095254 | 8/2009 |
| WO | WO-2009099982 | 8/2009 |
| WO | WO-2009106885 | 9/2009 |
| WO | WO-2009111280 | 9/2009 |
| WO | WO-2009115517 | 9/2009 |
| WO | WO-2009117157 | 9/2009 |
| WO | WO-2010015803 | 2/2010 |
| WO | WO-2010016005 | 2/2010 |
| WO | WO-2010017047 | 2/2010 |
| WO | WO-2010017055 | 2/2010 |
| WO | WO-2010034738 | 4/2010 |
| WO | WO-2010048131 | 4/2010 |
| WO | WO-2010051549 | 5/2010 |
| WO | WO-2010054398 | 5/2010 |
| WO | WO-2010059836 | 5/2010 |
| WO | WO-2010063634 | 6/2010 |
| WO | WO-2010068483 | 6/2010 |
| WO | WO-2010071837 | 6/2010 |
| WO | WO-2010073034 | 7/2010 |
| WO | WO-2010075200 | 7/2010 |
| WO | WO-2010086040 | 8/2010 |
| WO | WO-2010091409 | 8/2010 |
| WO | 2011006074 A1 | 1/2011 |
| WO | WO-2011003065 | 1/2011 |
| WO | WO-2011006074 | 1/2011 |
| WO | WO-2011008830 | 1/2011 |
| WO | WO-2011017513 | 2/2011 |
| WO | WO-2011022439 | 2/2011 |
| WO | WO-2011025706 | 3/2011 |
| WO | WO-2011035855 | 3/2011 |
| WO | WO-2011044157 | 4/2011 |
| WO | WO-2011068667 | 6/2011 |
| WO | WO-2011121096 | 6/2011 |
| WO | WO-2011086531 | 7/2011 |
| WO | WO-2011113606 | 9/2011 |
| WO | WO-2011117145 | 9/2011 |
| WO | WO-2011124998 | 10/2011 |
| WO | WO-2011130689 | 10/2011 |
| WO | WO-2011138751 | 11/2011 |
| WO | WO-2011143399 | 11/2011 |
| WO | WO-2011143419 | 11/2011 |
| WO | WO-2011143422 | 11/2011 |
| WO | WO-2011143423 | 11/2011 |
| WO | WO-2011143425 | 11/2011 |
| WO | WO-2011143426 | 11/2011 |
| WO | WO-2011144584 | 11/2011 |
| WO | WO-2011144585 | 11/2011 |
| WO | WO-2011163518 | 12/2011 |
| WO | WO-2012007375 | 1/2012 |
| WO | WO-2012022045 | 2/2012 |
| WO | WO-2012027236 | 3/2012 |
| WO | WO-2012067822 | 5/2012 |
| WO | WO-2012074754 | 6/2012 |
| WO | WO-2012078855 | 6/2012 |
| WO | WO-2012100342 | 8/2012 |
| WO | 2012138938 A1 | 10/2012 |
| WO | WO-2012138938 | 10/2012 |
| WO | WO-2012143510 | 10/2012 |
| WO | WO-2012143796 | 10/2012 |
| WO | WO-2012158785 | 11/2012 |
| WO | WO-2012177997 | 12/2012 |
| WO | WO-2012178124 | 12/2012 |
| WO | WO-2013010136 | 1/2013 |
| WO | WO-2013049720 | 4/2013 |
| WO | WO-2013049722 | 4/2013 |
| WO | WO-2013049726 | 4/2013 |
| WO | WO-2013049859 | 4/2013 |
| WO | WO-2013052263 | 4/2013 |
| WO | WO-2013059587 | 4/2013 |
| WO | 2013152298 A1 | 10/2013 |
| WO | WO-2013138436 | 10/2013 |
| WO | WO-2013151930 | 10/2013 |
| WO | WO-2013151938 | 10/2013 |
| WO | WO-2013154878 | 10/2013 |
| WO | WO-2013171470 | 11/2013 |
| WO | WO-2013174930 | 11/2013 |
| WO | WO-2013174931 | 11/2013 |
| WO | WO-2014011911 | 1/2014 |
| WO | WO-2014015523 | 1/2014 |
| WO | WO-2014023691 | 2/2014 |
| WO | WO-2014025850 | 2/2014 |
| WO | WO-2014025852 | 2/2014 |
| WO | WO-2014025854 | 2/2014 |
| WO | WO-2014026984 | 2/2014 |
| WO | WO-2014029723 | 2/2014 |
| WO | WO-2014035140 | 3/2014 |
| WO | WO-2014039831 | 3/2014 |

(56) References Cited

FOREIGN PATENT DOCUMENTS

| WO | WO-2014042433 | 3/2014 |
|----|---------------|--------|
| WO | WO-2014044691 | 3/2014 |
| WO | WO-2014047648 | 3/2014 |
| WO | WO-2014066435 | 5/2014 |
| WO | WO-2014066552 | 5/2014 |
| WO | WO-2014089379 | 6/2014 |
| WO | 2015085132 A1 | 6/2015 |
| WO | 2015195740 A1 | 12/2015 |
| WO | WO-2015187451 | 12/2015 |
| WO | 2017059357 A1 | 4/2017 |

OTHER PUBLICATIONS

Reaper et al. Selective kiling of ATM- or p-53 defiicent cancer cells through inhibition of ATR. (Nature Chemical Biology, vol. 7, Jul. 2011).*

Abdel-Magid, "Inhibitors of ATR Kinase for Treatment of Cancer," Medicinal Chemistry Letters, vol. 4, No. 8, Jun. 2013 (pp. 688-689).

Adamczyk et al., "Synthesis of 3,7-dihydroimidazo[1,2a]pyrazine-3-ones and their chemiluminescent properties," Tetrahedron, vol. 59, No. 41, Oct. 2003 (pp. 8129-8142).

Ahmed et al., "Synthesis and anti-tumor activities of some new pyridines and pyrazolo[1,5-a]pyrimidines," European Journal of Medicinal Chemistry, vol. 44, No. 9, Sep. 2009 (pp. 3519-3523).

Ahmed et al., "Synthesis of some Pyrazolopyrimidines as Purine Analogues," Journal of Heterocyclic Chemistry, vol. 44, No. 4, Jul.-Aug. 2007 (pp. 803-810).

Albert et al., "Inhibition of Poly(ADP-Ribose) Polymerase Enhances Cell Death and Improves Tumor Growth Delay in Irradiated Lung Cancer Models," Clinical Cancer Research, vol. 13, No. 10, May 2007 (pp. 3033-3042).

American Brain Tumor Association (ABTA) http://www.abta.org/brain-tumor-information/types-of-tumors/glioma.html?print=t. Accessed Mar. 9, 2016 (3 pages).

Amiri-Kordestani et al., "Why Do Phase III Clinical Trials in Oncology Fail so Often?" Journal of National Cancer Institute, vol. 104, No. 8, Apr. 2012 (pp. 568-569).

Ammar et al., "3-Ethoxycarbonylmethylenequinoxalin-2-one in Heterocyclic Synthesis. Part 1: Synthesis of New Substituted and Condensed Quinoxalines," Afinidad, vol. 62, No. 516, Jan. 2005 (pp. 151-160).

Bartucci et al., "Therapeutic targeting of Chk1 in NSCLC stem cells during chemotherapy," Cell Death and Differentiation, vol. 19, No. 5, May 2012 (pp. 768-778).

Bastin et al., "Salt Selection and Optimisation Procedures for Pharmaceutical New Chemical Entities," Organic Process Research and Development, vol. 4, No. 5, Jul. 2000 (pp. 427-435).

Bergenske et al., "The selective ATR inhibitor VX-970 enhances the therapeutic effects of radiation and temozolomide in patient-derived xenografts (PDXs) of glioblastoma (GBM)," Mayo Clinic, Poster, No Month Listed 2016 (1 page)

Bhattacharya et al., "Thermoanalytical and Crystallographic Methods," Polymorphism in Pharmaceutical Solids, Brittain ed., Informal Healthcare, Chapter 9, No Month Listed 2009 (pp. 318-346).

Biss et al., "Selective tumor killing based on specific DNA-damage response deficiencies," Cancer Biology & Therapy, vol. 13, No. 3, Mar. 2012 (pp. 239-246).

Boylan et al., "Parenteral Products," Chapter 12, Modern Pharmaceutics, Fourth Edition, New York: M. Dekker, No Month Listed 1997 (34 pages).

Bracher et al., "Total Synthesis of the Indolizidinium Alkaloid Ficuseptine," European Journal of Organic Chemistry, vol. 2002, No. 14, Jul. 2002 (pp. 2288-2291).

Brittain, editor, "Polymorphism in pharmaceutical solids," CRC Press; No Month Listed 2009, Chapters 7 (pp. 233-281) and 12 (pp. 436-480).

Buscemi et al., "DNA damage-induced cell cycle regulation and function of novel Chk2 phosphoresidues," Molecular and Cellular Biology, vol. 26, No. 21, Nov. 2006 (pp. 7832-7845).

Byrn et al., "Pharmaceutical Solids: A Strategic Approach to Regulatory Considerations," Pharmaceutical Research, vol. 12, No. 7, Jul. 1995 (pp. 945-954).

Caira, "Crystalline Polymorphism of Organic Compounds," Topics in Current Chemistry, Design of Organic Solids, Feb. 1999 (pp. 163-208).

Campbell, T., "AbbVie's PARP Inhibitor Comes Up Empty," https://www.fool.com/investing/2017/04/20/abbvies-parp-inhibitor-comes-up-empty.aspx?source=isesitlnk0000001&mrr=1.00. Accessed Oct. 15, 2018 (2 pages).

Campone et al., "Phase I and pharmacokinetic trial of AP5346, a DACH-platinum-polymer conjugate, administered weekly for three out of every 4 weeks to advanced solid tumor patients," Cancer Chemotherapy & Pharmacology, vol. 60, No. 4, Sep. 2007 (pp. 523-533).

Cerami et al., "The cBio cancer genomics portal: an open platform for exploring multidimensional cancer genomics data," Cancer Discovery, vol. 2, No. 5, May 2012 (pp. 401-404).

Chabner et al., Goodman & Gillman's Pharmacological Basis of Therapeutics, Twelfth Edition, McGraw Hill, No Month Listed 2011, Chapters 60 and 61 (pp. 1677-1730).

Charrier et al, "Discovery of Potent and Selective Inhibitors of Ataxia Telangiesctasia Mutated and Rad3 Related (ATR) Protein Kinase as Potential Anticancer Agents," Journal of Medicinal Chemistry, vol. 54, No. 7, Mar. 2011 (pp. 2320-2330).

Charrier et al., "Discovery of Potent and Selective Inhibitors of ATR (Ataxia Telangiectasia Mutated and Rad3 Related) as Potential Anticancer Agents," Supporting Information, Apr. 14, 2011 (47 pages).

Charrier, "Discovery of potent and selective inhibitors of Ataxia Telangiectasia mutated and Rad3 related (ATR) protein kinase as potential anticancer agents," Presentation, ACS Denver 2011, Aug. 28, 2011 (21 pages).

Chawla et al., "Challenges in Polymorphism of Pharmaceuticals," CRIPS, vol. 5, No. 1 Jan.-Mar. 2004 (pp. 12-15).

Chen et al., "Development of biomarker of ATR activity in surrogate human tissues," Newcastle University, Poster, Nov. 2012 (1 page).

Chen et al., "Targeting the S and G2 checkpoint to treat cancer," Drug Discovery Today, vol. 17, No. 5-6, Mar. 2012 (pp. 194-202).

Cheung-Ong et al., "DNA-Damaging Agents in Cancer Chemotherapy: Serendipity and Chemical Biology," Chemistry and Biology, vol. 20, May 2013 (pp. 648-659).

Citrin, "Short-Term Screening Assays for the Identification of Therapeutics for Cancer," Cancer Research, vol. 76, No. 12, Jun. 2016 (pp. 3443-3445).

Clark et al., "Mass Spectrometry of Pyrrolo[2,3-b]pyrazines and Pyrazino[2,3-b]indole," Organic Mass Spectrometry, vol. 12, No. 7, Jul. 1977 (pp. 421-423).

Cliby et al., "Overexpression of a kinase-inactive ATR protein causes sensitivity to DNA-damaging agents and defects in cell cycle checkpoints," The EMBO Journal, vol. 17, No. 1, Jan. 1998 (pp. 159-169).

Cortez, "Caffeine inhibits checkpoint responses without inhibiting the ataxia-telangiectasia-mutated (ATM) and ATM- and Rad3-related (ATR) protein kinases," The Journal of Biological Chemistry, vol. 278, No. 39, Sep. 2003 (pp. 37139-37145).

Curtin, "Inhibiting the DNA damage response as a therapeutic manoeuvre in cancer," British Journal of Pharmacology, vol. 169, No. 8, Aug. 2013 (pp. 1745-1765).

Darabantu et al., "Synthesis of new polyaza heterocycles. Part 42: Diazines," Tetrahedron, vol. 61, No. 11, Mar. 2005 (pp. 2897-2905).

De Wergifosse et al., "Coelenterazine: a two-stage antioxidant in lipid micelles," Free Radical Biology and Medicines, vol. 36, No. 3, Feb. 2004 (pp. 278-287).

Dias et al., "Synthesis of 2,6-diphenylpyrazine derivatives and their DNA binding and cytotoxic properties," European Journal of Medicinal Chemistry, vol. 40, No. 12, Dec. 2005 (pp. 1206-1213).

El-Emary, "Synthesis and Biological Activity of Some New Pyrazolo[3,4-b]pyrazines," Journal of the Chinese Chemical Society, vol. 53, No. 2, Apr. 2006 (pp. 391-401).

Elnagdi et al., "Synthesis of Substituted Azaindenes: Synthesis of New Pyrazolo[1,5-a]pyrimidine Derivatives," Bulletin of the Chemical Society of Japan, vol. 63, No. 6, Jan. 1990 (pp. 1854-1856).

(56) References Cited

OTHER PUBLICATIONS

Erickson et al., "Structure-guided expansion of kinase fragment libraries driven by support vector machine models," Biochimica et Biophysica Acta, vol. 1804, No. 3, Mar. 2010 (pp. 642-652).

Faber et al., "A Plug-In Program to Perform Hanawalt or Fink Search-Indexing Using Organics Entries in the ICDD PDF-4/Organics 2003 Database," International Center for Diffraction Data, Advances in X-Ray Analysis, vol. 47, Mar. 2004 (pp. 166-173).

Feng Qi et al., "Chemi- and bio-luminescence of coelenterazine analogs with phenyl homologs at the C-2 position," Journal of the Chemical Society, Perkin Transactions 1: Organic and Bio-Organic Chemistry, vol. 13, No Month Listed 1992 (pp. 1607-1611).

Fernandes et al., "Synthesis and Biological Activity of Heterocyclic Derivatives derived from Ethyl-2-hydroxy-quinoxaline-3-carboxylate," Journal of the Indian Chemical Society, vol. 63, Apr. 1986 (pp. 427-429).

FierceBiotech, http://www.fiercebiotech.com/biotech/abbvie-parp-inhibitor-veliparib-flunks-two-phase-3-trials. Accessed Oct. 19, 2018 (1 page).

Finlay et al. "Modulation of DNA repair by pharmacological inhibitors of the PIKK protein kinase family," Bioorganic and Medicinal Chemistry Letters, vol. 22, Jul. 2012 (pp. 5352-5359).

Flynn et al., "Alternative lengthening of telorneres renders cancer cells hypersensitive to ATR inhibitors," Science, vol. 347, No. 6219, Jan. 2015 (pp. 273-277).

Fokas et al., "Targeting ATR in DNA damage response and cancer therapeutics," Cancer Treatment Reviews, vol. 40, No. 1, Feb. 2014 (pp. 109-117).

Fokas et al., "Targeting ATR in vivo using the novel inhibitor VE-822 results in selective sensitization of pancreatic tumors to radiation," Cell Death and Disease, vol. 3, No. 12, Dec. 2012 (pp. 1-10).

Foote et al., "Discovery of 4-{4-[(3R)-3-Methylmorpholin-4-yl]-6 41-(methylsulfonyecyclopropyl]pyrimidin-2-y11-lH-indole (AZ20): a potent and selective inhibitor of ATR protein kinase with monotherapy in vivo antitumor activity," Journal of Medicinal Chemistry, vol. 56, No. 5, Mar. 2013 (pp. 2125-2138).

Foote et al., "Drugging ATR: progress in the development of specific inhibitors for the treatment of cancer," Future Medicinal Chemistry, vol. 7, No. 7, Jun. 2015 (pp. 873-891).

Geng et al, "Checkpoint Signaling, Base Excision Repair, and PARP Promote Survival of Colon Cancer Cells Treated with S-Fluorodeoxyuridine but Not S-Fluorouracil," PLoS One, vol. 6, No. 12, Dec. 2011 (10 pages).

Gentili et al., "Alpha2-Adrenoreceptors Profile Modulation. 4. From Antagonist to Agonist Behavior," Journal of Medicinal Chemistry, vol. 51, No. 14, Jun. 2008 (pp. 4289-4299).

Golub T.R., "Molecular classification of cancer: class discovery and class prediction by gene expression monitoring," Science, vol. 286, No. 5439, Oct. 1999 (pp. 531-537).

Goto et al., "Squid bioluminescence I. Structure of watasenia oxyluciferin, a possible light-emitter in the bioluminescence of watasenia scintillans," Tetrahedron Letters, vol. 15, No. 26, May 1974 (pp. 2321-2324).

Guichard et al., "The pre-clinical in vitro and in vivo activity of AZD6738: A potent and selective inhibitor of ATR kinase [abstract]," In: Proceedings of the 104th Annual Meeting of the American Association for Cancer Research; Apr. 6-10, 2013; Washington, DC Philadelphia (PA): AACR; Cancer Research, vol. 73 (8 Supplement), Abstract No. 3343, Aug. 2013 (pp. 3343-3343).

Gupta et al., "Angiogenesis: a curse or cure?" Postgraduate Medical Journal, vol. 81, No. 954, Apr. 2005 (pp. 236-242).

Hackam et al., "Translation of research evidence from animals to humans," The Journal of the American Medical Association, vol. 296, No. 14, Oct. 2006 (pp. 1731-1732).

Hall et al., "Potentiation of tumor responses to DNA damaging therapy by the selective ATR inhibitor VX-970," Oncotarget, vol. 5, No. 14, Jul. 2014 (pp. 5674-5685).

Hall-Jackson et al., "ATR is a caffeine-sensitive, DNA-activated protein kinase with a substrate specificity distinct from DNA-PK," Oncogene, vol. 18, No. 48, Nov. 1999 (pp. 6707-6713).

Hanawalt et al., "Chemical Analysis by X-Ray Diffraction: Classification and Use of X-Ray Diffraction Patterns," Powder Diffractions, vol. 1, No. 2, Jun. 1986 (pp. 2-14).

Hancock et al., "Characteristics and significance of the amorphous state in pharmaceutical systems," Journal of Pharmaceutical Sciences, vol. 86, No. 1, Jan. 1997 (pp. 1-12).

Hart et al., "Renilla Reinformis Bioluminescence: Luciferase-Catalyzed Production of Nonradiating Excited States from Luciferin Analogues and Elucidation of the Excited State Species Involved in Energy Transfer to Renilla Green Fluorescent Protein," Biochemistry, vol. 18, No. 11, May 1979 (pp. 2204-2210).

Hickson et al., "Identification and Characterization of a Novel and Specific Inhibitor of the Ataxia-Telangiectasia Mutated Kinase ATM," Cancer Research vol. 64, No. 24, Dec. 2004 (pp. 9152-9159).

Hilfiker et al., "Relevance of Solid-state Properties for Pharmaceutical Products," Polymorphism—In the Pharmaceutical Industry, Wiley-VCH Verlag GmbH & Co KGaA, Jun. 2006 (pp. 1-19).

Hilton et al., "Identification and characterisation of 2-anlinopyridine inhibitors of checkpoint kinase 2," Bioorganic & Medicinal Chemistry, vol. 18, No. 2, Sep. 2009 (pp. 707-718).

Hirano et al., "Bioluminescent properties of fluorinated semisynthetic aequorins," Tetrahedron Letters, vol. 39, No. 31, Jul. 1998 (pp. 5541-5544).

Ho, "Studies on the Synthesis of New 3-(3,5-Diamino-1-substituted-pyrazol-4-yl)azo-thieno[2,3-b]pyridines and 3-(2Amino-5,7-disubstituted-pyrazolo[1,5-a]pyrin1idine-3-yl)azo-thieno[2,3-b]pyridines," Journal of the Chinese Chemical Society, vol. 46, No. 6, Dec. 1999 (pp. 955-962).

Hocke et al., "A synthetic lethal screen identifies ATR-inhibition as a novel therapeutic approach for POLD1-deficient cancers," Oncotarget, vol. 7, No. 6, Feb. 2016 (pp. 7080-7095).

Hopps et al. "A Review of PARP Inhibitors in Clinical Development," Journal of Hematology Oncology Pharmacy, vol. 2, No. 1, Mar. 2012 (pp. 18-28).

Hubackova et al., "Regulation of the PML tumor suppressor in drug-induced senescence of human normal and cancer cells by JAK/STAT-mediated signaling," Cell Cycle, vol. 9, No. 15, Aug. 2010 (pp. 3085-3099)

Huntoon et al., "ATR inhibition broadly sensitizes ovarian cancer cells to chemotherapy independent of BRCA status," Cancer Research, vol. 73, No. 12, Jun. 2013 (pp. 3683-3691).

Hussein, "Novel synthesis of some new pyrimido[1,6-a]pyrimidine and pyrazolo[1,5-a]pyrirnidine derivatives," Journal of Heterocyclic Chemistry, vol. 49, No. 2, Mar. 2012 (pp. 446-451)

International Search Report and Written Opinion issued by the European Patent Office as International Searching Authority for International Application No. PCT/US2005/040344, dated Mar. 20, 2006 (11 pages).

International Search Report and Written Opinion issued by the European Patent Office as International Searching Authority for International Application No. PCT/US2009/063922, dated Mar. 15, 2010 (10 pages).

International Search Report and Written Opinion issued by the European Patent Office as International Searching Authority for International Application No. PCT/US2009/068827, dated Mar. 4, 2010 (9 pages).

International Search Report and Written Opinion issued by the European Patent Office as International Searching Authority for International Application No. PCT/US2011/036214, dated Jun. 17, 2011 (9 pages).

International Search Report and Written Opinion issued by the European Patent Office as International Searching Authority for International Application No. PCT/US2011/036239, dated Oct. 12, 2011 (11 pages).

International Search Report and Written Opinion issued by the European Patent Office as International Searching Authority for International Application No. PCT/US2011/036242, dated Jun. 28, 2011 (8 pages).

(56) References Cited

OTHER PUBLICATIONS

International Search Report and Written Opinion issued by the European Patent Office as International Searching Authority for International Application No. PCT/US2011/036243, dated Jan. 11, 2012 (13 pages).
International Search Report and Written Opinion issued by the European Patent Office as International Searching Authority for International Application No. PCT/US2011/036245, dated Dec. 28, 2011 (12 pages).
International Search Report and Written Opinion issued by the European Patent Office as International Searching Authority for International Application No. PCT/US2011/036246, dated Jul. 19, 2011 (10 pages).
International Search Report and Written Opinion issued by the European Patent Office as International Searching Authority for International Application No. PCT/US2011/041705, dated Aug. 23, 2011 (11 pages).
International Search Report and Written Opinion issued by the European Patent Office as International Searching Authority for International Application No. PCT/US2012/032438, dated Aug. 10, 2012 (7 pages).
International Search Report and Written Opinion issued by the European Patent Office as International Searching Authority for International Application No. PCT/US2012/043895, dated Aug. 28, 2012 (9 pages).
International Search Report and Written Opinion issued by the European Patent Office as International Searching Authority for International Application No. PCT/US2012/043896, dated Oct. 9, 2012 (11 pages).
International Search Report and Written Opinion issued by the European Patent Office as International Searching Authority for International Application No. PCT/US2012/043897, dated Jul. 20, 2012 (9 pages).
International Search Report and Written Opinion issued by the European Patent Office as International Searching Authority for International Application No. PCT/US2012/058117, dated Jan. 30, 2013 (13 pages).
International Search Report and Written Opinion issued by the European Patent Office as International Searching Authority for International Application No. PCT/US2012/058119, dated Nov. 12, 2012 (8 pages).
International Search Report and Written Opinion issued by the European Patent Office as International Searching Authority for International Application No. PCT/US2012/058121, dated Nov. 12, 2012 (8 pages).
International Search Report and Written Opinion issued by the European Patent Office as International Searching Authority for International Application No. PCT/U82012/058127, dated Apr. 23, 2013 (15 pages).
International Search Report and Written Opinion issued by the European Patent Office as International Searching Authority for International Application No. PCT/US2012/058374, dated Jan. 8, 2013 (13 pages).
International Search Report and Written Opinion issued by the European Patent Office as International Searching Authority for International Application No. PCT/US2012/064421, dated Feb. 15, 2013 (9 pages).
International Search Report and Written Opinion issued by the European Patent Office as International Searching Authority for International Application No. PCT/US2012/064426, dated Feb. 1, 2013 (9 pages).
International Search Report and Written Opinion issued by the European Patent Office as International Searching Authority for International Application No. PCT/US2012/064430, dated Feb. 1, 2013 (10 pages).
International Search Report and Written Opinion issued by the European Patent Office as International Searching Authority for International Application No. PCT/US2012/064433, dated Feb. 26, 2013 (9 pages).
International Search Report and Written Opinion issued by the European Patent Office as International Searching Authority for International Application No. PCT/US2012/064435, dated Jan. 30, 2013 (8 pages).
International Search Report and Written Opinion issued by the European Patent Office as International Searching Authority for International Application No. PCT/US2013/035466, dated Aug. 23, 2013 (13 pages).
International Search Report and Written Opinion issued by the European Patent Office as International Searching Authority for International Application No. PCT/US2013/063254, dated Dec. 20, 2013 (9 pages).
International Search Report and Written Opinion issued by the European Patent Office as International Searching Authority for International Application No. PCT/US2013/064920, dated Feb. 27, 2014 (8 pages).
International Search Report and Written Opinion issued by the European Patent Office as International Searching Authority for International Application No. PCT/US2013/073457, dated Jan. 29, 2014 (7 pages).
International Search Report and Written Opinion issued by the European Patent Office as International Searching Authority for International Application No. PCT/US2013/073468, dated Apr. 1, 2014 (11 pages).
International Search Report and Written Opinion issued by the European Patent Office as International Searching Authority for International Application No. PCT/US2013/073471, dated Feb. 17, 2014 (7 pages).
International Search Report and Written Opinion issued by the European Patent Office as International Searching Authority for International Application No. PCT/US2013/073477, dated Jan. 30, 2014 (9 pages).
International Search Report and Written Opinion issued by the European Patent Office as International Searching Authority for International Application No. PCT/US2013/073482, dated Feb. 6, 2014 (8 pages).
International Search Report and Written Opinion issued by the European Patent Office as International Searching Authority for International Application No. PCT/US2014/068713, dated Jan. 29, 2015 (9 pages).
International Search Report and Written Opinion issued by the European Patent Office as International Searching Authority for International Application No. PCT/US2015/032879, dated Oct. 1, 2015 (10 pages).
International Search Report and Written Opinion issued by the European Patent Office as International Searching Authority for International Application No. PCT/US2015/036137, dated Sep. 24, 2015 (8 pages).
International Search Report and Written Opinion issued by the United States Patent and Trademark Office as International Searching Authority for International Application No. PCT/US2016/054996, dated Jan. 19, 2017 (12 pages).
Jia et al., "A Facile Preparation of 2,6-Diarylpyrazines," Heteroatom Chemistry, vol. 9, No. 3, Dec. 1998 (pp. 231-354).
Jiang et al., "Synthesis and cytotoxicity evaluation of novel indolylpyrimidiens and indolylpyrazines as potential antitummor agents," Bioorganic & Medicinal Chemistry, vol. 9, No. 8, May 2001 (pp. 1149-1154).
Johnson et al., "Relationships between drug activity and NCI preclinical in vitro and in vivo models and early clinical trials," British Journal of Cancer, vol. 84, No. 10, Feb. 2001, (pp. 1424-1431).
Jones et al., "Discovery of AZD6738, a potent and selective inhibitor with the potential to test the clinical efficacy of ATR kinase inhibition in cancer patients [abstract]," In: Proceedings of the 104th Annual Meeting of the American Association for Cancer Research; Washington, DC. Philadelphia (PA): AACR, Cancer Research, vol. 73, 8 Supplement: Abstract No. 2348, Apr. 6-10, 2013 (4 pages).
Jones et al., "A Suzuki Coupling Approach to Pyrazines Related to Coelenterazine," Synlett, vol. 6, Jun. 1996 (pp. 509-510).
Jordan et al., "Tamoxifen: a most unlikely pioneering medicine," Nature Review Drug Discovery, vol. 2, No. 3, Mar. 2003 (pp. 205-213).

(56) References Cited

OTHER PUBLICATIONS

Josse et al., "ATR inhibitors VE-821 and VX-970 sensitize cancer cells to topoisomerase 1 inhibitors by disabling DNA replication initiation and fork elongation responses," Cancer Research, vol. 74, No. 23, Dec. 2014 (pp. 6968-6979).
Kao et al., "Inhibition of y-H2AX after ionizing radiation as a biological surrogate of impaired upstream DNA damage signaling and radiosensitivity," Journal Cancer Molecules, vol. 5, No. 2, Jan. 2010 (pp. 49-54).
Katritzky et al., "Efficient synthesis of 3,5-functionalized isoxazoles and isoxazolines via 1,3-dipolar cycloaddition reactions of 1-propargyl- and 1-allylbenzotriazoles," Journal Heterocyclic Chemistly, vol. 37, No. 6, Nov./Dec. 2000 (pp. 1505-1510).
Kedar et al., "Interaction between PARP-1 and ATR in mouse fibroblasts is blocked by PARP inhibition," DNA Repair (Amst), vol. 7, No. 11, Nov. 2008 (pp. 1787-1798).
Kholodov et al., "Clinical Pharmcokinetics Part M: Medicine," No Month Listed 1985 (pp. 83-98, 134-138, 160, 378-80).
Kim et al. "Substrate Specificities and Identification of Putative Substrates of ATM Kinase Family Members," Journal of Biological Chemistry, vol. 274, No. 53, Dec. 1999 (pp. 37538-37543).
Kitagawa et al., "The ATM-dependent DNA Damage Signaling Pathway," Cold Spring Harbor Symposia on Quantitative Biology, vol. 70, No Month Listed 2005 (pp. 99-109).
Klicnar et al., "Studien in der Chinoxalinreihe III. Synthèses, Reaktionen and ir-spektren einiger 3-hydroxy-2-carboxymethylch inoxalin-derivative," Collection Czechoslovak Chemical Communications, vol. 30, Jul. 1964 (pp. 3092-3101).
Knight et al., "A pharmacological map of the P13-K family defines a role for p110alpha in insulin signaling," Cell, vol. 125, No. 4, May 2006 (pp. 733-747).
Krajewska et al., "ATR inhibition preferentially targets homologous recombination-deficient tumor cells," Oncogene, vol. 34, No. 26, Jun. 2015 (pp. 3474-3481).
Kumar et al., "Salt selection in drug development," Pharmaceutical Technology, vol. 32, No. 3, Mar. 2008 (pp. 128-146).
Kumpaty et al., "Synthesis of N-Methyl Secondary Amines," Synthetic Communications, vol. 33, No. 8, No Month Listed 2003 (pp. 1411-1416).
Kurasawa et al., "Revised Structure for the Product from the Reaction of 3-Hydrazinocarbonylmethylene-2-oxo-1,2,3,4-tetrahydroquinoxaline with Nitrous Acid," Chemical and Pharmaceutical Bulletin, vol. 32, No. 10, Oct. 1984 (pp. 4140-4143).
Kwok et al., "ATR inhibition induces synthetic lethality and overcomes chemoresistance in TP53-or ATM-defective chronic lymphocytic leukemia cells," Blood, vol. 127, No. 5, Feb. 2016 (pp. 582-595).
Lala et al., "Role of nitric oxide in tumor progression: lessons from experimental tumors," Cancer Metatasis Review, vol. 17, No. 1, Mar. 1998 (pp. 91-106).
Lau et al., "Pre-clinical efficacy of the ATR inhibitor AZD6738 in combination with the PARP inhibitor olaparibi [abstract]," In: Proceedings of the AACR-NCI-EORTC International Conference: Molecular Targets and Cancer Therapeutics; Boston, MA. Philadelphia (PA): AACR, Molecular Cancer Therapeutics, vol. 14, 12 Suppl 2, Abstract No. C60, Nov. 5-9, 2015 (4 pages).
Ledford, "Drug candidates derailed in case of mistaken identity," Nature, vol. 483, Mar. 2012 (1 page).
Leszczynska et al., "Preclinical testing of an ATR inhibitor demonstrates improved response to standard therapies for esophageal cancer," Radiotherapy and Oncology, vol. 121, No. 2, Nov. 2016 (pp. 232-238).
Lima et al., "Bioisosterism: a useful strategy for molecular modification and drug design," Current Medicinal Chemistry, vol. 12, No. 1, No Month Listed 2005 (pp. 23-49).
Ling et al., "Mechanism of Cell Cycle G2/M Arrest in Human Gastric Cancer BGC823 Cells Induced by Diallyl Disulfide," Chinese Journal of Clinical Oncology, vol. 28, No. 3, Feb. 2010 (pp. 121-125).
Liu et al., "Chemical Biology Foundation," Science Press, vol. 30, Sep. 2010 (pp. 213-218).
Loser et al., "Sensitization to Radiation and Alkylating Agents by Inhibitors of Poly(ADP-ribose) Polymerase Is Enhanced in Cells Deficient in DNA Double-Strand Break Repair," Molecular Cancer Therapeutics, vol. 9, No. 6, Jun. 2010 (pp. 1775-1787).
Luo et al., "Molecular dynamics-based self-organizing molecular field analysis on 3-amino-6-arypyrazines as the ataxia telangiectasia mutated and Rad3 related (ATR) protein kinase inhibitors," Medicinal Chemistry Research, vol. 23, No. 2, Jun. 2013 (pp. 1-12).
Maciag et al., "The Nitric Oxide Prodrug JS-K Is Effective against Non-Small-Cell Lung Cancer Cells In Vitro and In Vivo: Involvement of Reactive Oxygen Species," Journal of Pharmacology and Experimental Therapeutics, vol. 336, No. 2, Feb. 2011 (pp. 313-320).
McKenna et al., "Evaluation of the first potent and highly selective inhibitor of ATR inhibitor, VE-821: an approach to selectively sensitize cancer cells to ionizing radiation and hypoxia," Poster, Mar. 31, 2012 (1 page).
McKenna et al., "Evaluation of the first potent and highly selective inhibitor of ATR kinase: an approach to selectively sensitize cancer cells to ionizing radiation and hypoxia," Abstract, Mar. 31, 2012 (1 page).
McMahon, "VEGF Receptor Signaling in Tumor Angiogenesis," The Oncologist, vol. 5, supplement 1, No Month Listed 2000 (pp. 3-10).
Menezes et al., "A synthetic lethal screen reveals enhanced sensitivity to ATR inhibitor treatment in mantle cell lymphoma with ATM loss-of-function," Molecular Cancer Research, vol. 13, No. 1, Jan. 2015 (pp. 120-129).
Middleton et al., "Chemosensitisation By, and Single Agent Activity of, ATR Inhibitor VE-821 in Human Breast Cancer Cells," European Journal of Cancer, vol. 1, Nov. 2012 (pp. 85-86).
Middleton et al., "ATR as a Therapeutic Target Cancer Drug Discovery and Development," Author's Proof, No Month Listed 2013 (20 pages).
Mohni et al., "A Synthetic Lethal Screen Identifies DNA Repair Pathways that Sensitize Cancer Cells to Combined ATR Inhibition and Cisplatin Treatments," PLoS One, vol. 10, No. 5, May 2015 (22 pages).
Montano et al., "Sensitization of human cancer cells to gemcitabine by the Chk1 inhibitor MK-8776: cell cycle perturbation and impact of administration schedule in vitro and in vivo," BMC Cancer, vol. 13, No. 604, Dec. 2013 (14 pages).
Morgan et al., "Mechanism of radiosensitization by the Chk1/2 inhibitor AZD7762 involves abrogation of the G2 checkpoint and inhibition of homologous recombinational DNA repair," Cancer Research, vol. 70, No. 12, Jun. 2010 (pp. 4972-4981).
Muslimovic et al., "An optimized method for measurement of gamma-H2AX in blood mononuclear and cultured cells," Nature Protocol, vol. 3, No. 7, Jun. 2008 (pp. 1187-1193).
Mutter et al., "Long-Term Outcomes of Breast Conservation Therapy in Unifocal versus Multifocal Early Stage Breast Cancer Patients," International Journal of Radiation Oncology, vol. 99, No. 2, Suppl 1:E611, Abstract No. 3455, Oct. 1, 2017 (pp. E24-E25).
Nakamura et al., "Bimodal chemiluminescence of 8-chlorostyryl-6-phenylethynylimidazopyrazinone: Large bathochronlic shift caused by a styryl group at 8-position," Tetrahedron Letters, vol. 39, No. 3-4, Jan. 1998 (pp. 301-304).
Nghiem et al., "ATR is not required for p53 activation but synergizes with p53 in the replication checkpoint," Journal of Biological Chemistry, vol. 277, No. 6, Feb. 2002 (pp. 4428-4434).
No Author Listed, "Guidance for Industry: Estimating the Maximum Safe Starting Dose in Initial Clinical Trials for Therapeutics in Adult Healthy Volunteers. U.S. Department of Health and Human Services," Food and Drug Admimstration, Center for Drug Evaluation and Research, Jul. 2005 (29 pages).
No Author Listed, "Phase III EMBRACA Trial Meets Primary Endpoint," American Association for Cancer Research https://www.aacr.org/Newsroom/Pages/News-Release-Detail.aspx?ItemID=1134. Accessed Oct. 15, 2018 (3 pages).
Non-Final Office Action dated Aug. 8, 2013 in U.S. Appl. No. 13/631,727.
Non-Final Office Action dated Aug. 8, 2013 in U.S. Appl. No. 13/631,732.

(56) References Cited

OTHER PUBLICATIONS

Non-Final Office Action dated Jun. 27, 2014 in U.S. Appl. No. 14/098,640.
Non-Final Office Action dated Jun. 27, 2014 in U.S. Appl. No. 14/098,655.
Nowotnik et al., "ProLindac (AP5346): a review of the development of an HPMA DACH platinum Polymer Therapeutic," Advanced Drug Delivery Reviews, vol. 61, No. 13, Nov. 2009 (pp. 1214-1219).
Otero et al., "Syntheses of Acyclo-C-nucleoside Analogs from 2,3:4,5-Di-Oisopropylidene-Di-O-isopropylidene-D-xylose," Journal of Carbohydrate Chemistry, vol. 24, Nov. 2005 (pp. 809-829).
Otero et al., "Synthesis of Iso-C-nucleoside Analogues from 1-(Methyl 2-0-benzyl]-4,6-0-benzylidene-3-deoxy-a-D-altropyranosid-3-yl)but-3-yn-2-ones", Zeitschrift für Naturforschung, vol. 60, No. 11, Nov. 2005 (pp. 1175-1185).
Patani et al, "Bioisosterism: A Rational Approach in Drug Design," Chemical Reviews, vol. 96, No. 8, Dec. 1996 (pp. 3147-3176).
Peasland et al., "Identification and evaluation of a potent novel ATR inhibitor, NU6027, in breast and ovarian cancer cell lines," British Journal of Cancer, vol. 105, No. 3, Jul. 2011 (pp. 372-381).
Pinedo et al., "Translational Research: The Role of VEGF in Tumor Angiogenesis," The Oncologist, vol. 5, supplement 1, No Month Listed 2000 (pp. 1-2).
Pires et al., "Targeting radiation-resistant hypoxic tumour cells through ATR inhibition," British Journal of Cancer, vol. 107, No. 2, Jul. 2012 (pp. 291-299).
Pollard et al., "Defining optimal dose schedules for ATR inhibitors in combination with DNA damaging drugs: Informing clinical studies of VX-970, the first-in-class ATR inhibitor," Proceedings: AACR Annual Meeting, Apr. 16-20, 2016 (4 pages).
Pollard, "Inhibition of the DNA Damage Response Kinase, ATR, as a Promising Anti-Cancer Approach," Presentation, Mar. 8, 2012 (28 pages).
Prescribing Information for Nariparib (19 pages).
Prescribing Information for Olaparib (11 pages).
Prescribing Information for Rucaparib (13 pages).
Prevo et al., "The novel ATR inhibitor VE-821 increases sensitivity of pancreatic cancer cells to radiation and chemotherapy," Cancer Biology and Therapy, vol. 13, No. 11, Sep. 2012 (pp. 1072-1081).
PubChem Opein Chemistry Database, Compound Summaries for AZD7762, LY2603618, SCH-900776, CHIR-124 and PF-477736.
PubChem Opein Chemistry Database, Compound Summaries for Olaparib, Veliparib, Rucaparib, BNIN673, MK-4827, AZD2461, E7016, INO-1001 and CEP-8983.
Ram et al., "Synthesis of bioisosteric pyrazolo[1,5-a]pyrinlidines as leishmanicides," Indian Journal of Chemistry, vol. 34B, Jun. 1995 (pp. 514-520).
Reaper et al., "Selective killing of ATM- or p53-deficient cancer cells through inhibition of ATR," Nature Chemical Biology, vol. 7, No. 7, Apr. 2011 (pp. 428-430).
Reaper et al., "Selective Killing of ATM- or p53-deficient cancer cells through inhibition of ATR," Presentation, Nov. 29, 2011 (31 pages).
Reaper et al., "Selective killing of ATM- or p53-deficient cancer cells through inhibition of ATR," Supplementary Information, Nature Chemical Biology, vol. 7, No. 7, Apr. 2011 (pp. 428-430).
Reaper, et al., "Evaluation of a Potent and Highly Selective Inhibitor of ATR Kinase: An Approach to Selectively Sensitize Cancer Cells to Genotoxic Drugs," Poster, Mar. 31, 2012 (1 page).
Reaper, et al., "Selective Killing of ATM- or p53-deficient cancer cells through inhibition of ATR," Presentation, Nov. 21, 2011 (25 pages).
Redon et al., y-H2AX as a biomarker of DNA damage induced by ionizing radiation in human peripheral blood lymphocytes and artificial skin, Advances in Space Research, vol. 43, No. 8, No Month Listed 2009 (pp. 1171-1178).
Registry (STN), 2004, RN 726138-31-4.

Richards et al., "An Autoinhibitory Tyrosine Motif in the Cell-Cycle-Regulated Nek7 Kinase Is Released through Binding of Nek9," Molecular Cell, vol. 36, No. 4, Nov. 2009 (pp. 560-570).
Ried, "Synthese neuer Heterocyclen ausgehend von Aminopyrazolen," Chemiker-Zeitung, 113, Jahrgang (1989) Nr. 5 (3 pages).
Rosell et al., "Premetrexed combination therapy in the treatment of non-small cell lung cancer," Seminars in Oncology, vol. 29, No. 2, Supplement 5, Apr. 2002 (pp. 23-29).
Saito et al., "Synthesis and in vitro evaluation of botryllazine B analogues as a new class of inhibitor against human aldose reductase," Tetrahedron, vol. 65, No. 15, Apr. 2009 (pp. 3019-3026).
Sanjiv et al., "Cancer-Specific Synthetic Lethality between ATR and CHK1 Kinase Activities," Cell Reports, vol. 14, No. 2, Jan. 2016 (pp. 298-309).
Sarkaria et al., "Inhibition of ATM and ATR Kinase Activities by the Radiosensitizing Agent, Caffeine," Cancer Research, vol. 59, No. 17, Sep. 1999 (pp. 4375-4382).
Schoppy et al., "Oncogenic stress sensitizes murine cancers to hypomorphic suppression of ATR," The Journal of Clinical Investigation, vol. 122, No. 1, Jan. 2012 (pp. 241-252).
Schultheiss et al., "Facile Synthesis of Diarylpyrazines Using Suzuki Coupling of Dichloropyrazines with Aryl Boronic Acids," Heterocycles, vol. 60, No. 8, Jun. 2003 (pp. 1779-1786).
Serajuddin, "Salt formation to improve drug solubility," Advanced Drug Delivery Reviews, vol. 59, No. 7, Jul. 2007 (pp. 603-616).
Sergeev, Brief course of Molecular Pharmacology, Moscow Medical Institute, No Month Listed 1975 (4 pages).
Sevilla et al., "Microwave-assisted synthesis of 1,3-dihydro-[1,2,5]thiadiazolo[3,4-b]pyrazine-2,2-dioxides," Tetrahedron Letters, vol. 47, No. 48, Nov. 2006 (pp. 8603-8606).
Shibamoto et al., "Radiosensitivity of Human Pancreatic Cancer Cells In Vitro and In Vivo, and the Effect of a New Hypoxic Cell Sensitizer, Doranidazole," Radiotherapy Oncology, vol. 56, No. 2, Aug. 2000 (pp. 265-270).
Shimomura et al., "Semi-synthetic aequorins with improved sensitivity to Ca2+ ions," Biochemical Journal, vol. 261, No. 3, Aug. 1989 (pp. 913-920).
Sinha, "Downfall of Iniparib: A PARP Inhibitor That Doesn't Inhibit PARP After All," Journal of the National Cancer Institute, vol. 106, No. 1, Jan. 2014 (2 pages).
Smith et al., "Addition to Carbon—Hetero Multiple Bonds," Chapter 16, In: March's Advanced Organic Chemistry: Reactions, Mechanisms, and Structure, Sixth Edition, John Wiley & Sons, Inc., No Month Listed 2007 (26 pages).
So et al., "Phosphorylation of SMC1 by ATR is required for desferrioxamine (DFO)-induced apoptosis," Cell Death and Disease, vol. 2, No. 3, Mar. 2011 (pp. 1-8).
Sugimoto et al., "Imidazopteridines. I. Synthesis of Imidazo[1,2-c]pteridine and Its Alkyl Derivatives," Bulletin of the Chemical Society of Japan, vol. 50, No. 10, Mar. 1977 (pp. 2744-2747).
Teng et al., "Pharmacologic inhibition of ATR and ATM offers clinically important distinctions to enhancing platinum or radiation response in ovarian, endometrial, and cervical cancer cells," Gynecologic Oncology, vol. 136, No. 3, Mar. 2015 (pp. 554-561).
Teranishi et al., "Synthesis and Chemiluminescence of Coelenterazine (Oplophorus Luciferin) Analogues," Bulletin of the Chemical Society of Japan, vol. 63, No. 11, No Month Listed 1990 (pp. 3132-3140).
Thangadurai et al., "X-Ray Powder Diffraction Patterns for Certain β-Lactam, Tetracycline and Macrolide Antibiotic Drugs," Analytical Sciences, vol. 21, Jul. 2005 (pp. 833-838).
Toledo et al., "A cell-based screen identifies ATR inhibitors with synthetic lethal properties for cancer-associated mutations," Nature Structural Molecular Biology, vol. 18, No. 6, Jun. 2011 (pp. 721-727).
Tutin, "CCLVII. Syntheses in the epinephrine series. Part II. The formation and properties of some 2 : 5- and 2 : 6-substituted pyrazines and their conversion into amino-ketones and imino-diketones," Jouranl of the Chemical Society, Transactions, vol. 97, No Month Listed 1910 (pp. 2495-2524).
U.S. Appl. No. 15/608,630 of Charrier et al., filed May 30, 2017.
U.S. Appl. No. 15/633,477 of Ahmad et al., filed Jun. 26, 2018.
U.S. Appl. No. 15/693,521 of Falcon et al., filed Sep. 1, 2017.

(56) References Cited

OTHER PUBLICATIONS

U.S. Appl. No. 15/763,366 of Pollard et al., filed Mar. 26, 2018.
U.S. Appl. No. 15/849,241 of Charrier et al., filed Dec. 20, 2017.
U.S. Appl. No. 15/967,110 of Charrier et al., filed Apr. 30, 2018.
Underhill et al., "A review of PARP inhibitors: from bench to bedside," Annals of Oncology, vol. 22, No. 2, Feb. 2011 (pp. 268-279).
Vavrova et al., "Inhibition of ATR kinase with the selective inhibitor VE-021 results in radiosensitization of cells of promyeloctic leukaemia (HL-60)," Radiation and Environmental Biophysics, vol. 52, No. 4, Nov. 2013 (pp. 471-479).
Vendetti et al., "The orally active and bioavailable ATR kinase inhibitor AZD6738 potentiates the anti-tumor effects of cisplatin to resolve ATM-deficient non-small cell lung cancer in vivo," Oncotarget, vol. 6, No. 42, Dec. 2015 (pp. 44289-44305).
Vicent, "Polymer Anticancer Drug Conjugates: Use as Single Agents and as Combination Therapy," 2007 AACR Annual Meeting Apr. 14-18, 2007 (pp. 56-62)
Vippagunta et al., "Crystalline solids," Advanced Drug Delivery Review, vol. 48, No. 1, May 2001 (pp. 3-26).
Voskoglou-Nomikos et al., "Clinical Predictive Value of the in Vitro Cell Line, Human Xenograft, and Mouse Allograft Preclinical Cancer Models," Clinical Cancer Research, vol. 9, No. 11, Sep. 2003 (pp. 4227-4239).
Wang et al., "Chk1-Mediated Phosphorylation of FANCE Is Required for the Fanconi Anemia/BRCA Pathway," Molecular and Cellular Biology, vol. 27, No. 8, Apr. 2007 (pp. 3098-3108).
Wang et al., "DNA Polymerase β Mutations in Human Colorectal Cancer," Cancer Research, vol. 52, Sep. 1992 (pp. 4824-4827).
Ward et al., "Histone H2AX Is Phosphorylated in an ATR-dependent Manner in Response to Replicational Stress," Journal of Biological Chemistry, vol. 276, No. 51, Dec. 2001 (pp. 47759-47762).
Weston et al., "The PARP inhibitor olaparib induces significant killing of ATM-deficient lymphoid tumor cells in vitro and in vivo," Blood, vol. 116, No. 22, Nov. 2010 (pp. 4578-4587).
Wilsker et al., "Loss of ataxia telangiectasia mutated- and Rad3-related function potentiates the effects of chemotherapeutic drugs on cancer cell survival," Molecular Cancer Therapeutics, vol. 6, No. 4, Apr. 2007 (pp. 1406-1413).
Wolff, Burger's Medicinal Chemistry and Drug Discovery, Fifth Edition, vol. I: Principles and Practice, No Month Listed 1995 (pp. 975-977).
Wu et al., "Chemi- and bioluminescence of coelenterazine analogues with a conjugated group at the C-8 position," Tetrahedron Letters, vol. 42, No. 16, Apr. 2001 (pp. 2997-3000).
Wuts, Greene's Protective Groups in Organic Synthesis, 4th Edition, 2006, John Wiley and Sons, Chapter 4.
Wuts, Greene's Protective Groups in Organic Synthesis, 4th Edition, 2006, John Wiley and Sons, Chapter 7.
Xiao et al., "Chk1 Mediates S and G2 Arrests through Cdc25A Degradation in Response to DNA-damaging Agents," The Journal of Biological Chemistry, vol. 27 8, No. 4, Jun. 2003 (pp. 21767-21773).
Yardley, "Iniparib: The Fairy Tale Dream Comes to an End," Feb. 25, 2015 http://www.ascopost.com/issues/february-15-2015/iniparib-the-fairy-tale-dream-comes-to-an-end/. Accessed Oct. 19, 2018 (4 pages).
Yokoi et al., "Hypoxia Increases Resistance of Human Pancreatic Cancer Cells to Apoptosis Induced by Gemcitabine," Clinical Cancer Research, vol. 10, No. 7 , Apr. 2004 (pp. 2299-2306).
Zabludoff et al., "AZD7762, a novel checkpoint kinase inhibitor, drives checkpoint abrogation and potentiates DNA-targeted therapies," Molecular Cancer Therapeutics, vol. 7, No. 9, Sep. 2008 (pp. 2955-2966).
Karnitz et al., "Molecular Pathways: Targeting ATR in Cancer Therapy", Clin. Cancer Res: 21(21) Nov. 1, 2015, pp. 4780-4785.
Pabla et al., "hMSH2 Recruits ATR to DNA Damage Sites for Activation during DNA Damage-induced Apostsis", The Journal of Biological Chemistry, vol. 286, No. 12, Mar. 2011, pp. 10411-10418.
Shapiro et al., "Abstract CT012: Phase 1 trial of first-in-class ATR inhibitor VX-970 in combination with cisplatin (Cis) in patients (pts) with advanced solid tumors (NCT02157792)", Cancer Res. vol. 76, Issue 14 Suppl. Jul. 2016.
Supplementary European Search Report for Application No. 16852781.0, dated Apr. 17, 2019.
Pabla et al.: "hMSH2 Recruits ATR to DNA Damage Sites for Activation during DNA Damage-induced Apoptosis" The journal of biological chemistry, Mar. 25, 2011, vol. 286, No. 12, pp. 10411-10418.
Shapiro G. et al.: "Abstract CT012: Phase 1 trial of first-in-class ATR inhibitor VX-970 in combination with cisplatin (Cis) in patients (pts) with advanced solid tumors (NCT02157792)" Cancer research, Jan. 7, 2016, pp. 1-5.
Moore et al., "Genetic profile of 22 pancreatic carcinoma cell lines." Vichows Arch. 2001; 439: 798-802.
U.S. Appl. No. 17/184,813 of Charrier et al., filed Feb. 25, 2021.
U.S. Appl. No. 17/444,318 of Pollard et al., filed Aug. 3, 2021.
U.S. Appl. No. 17/448,147 of Helleday et al., filed Sep. 20, 2021.
Response to Communication Pursuant to Article 94(3) EPC from EP 16852781.0, filed Nov. 8, 2021.

* cited by examiner

Optimization of Compound A-2 Dose Schedule In Vitro

Optimization of Intravenous Compound A-2 Dose Schedule in Combination With Gemcitabine In Vivo -○- Vehicle (5% Captisol/3% mannitol IV 2x weekly)
-◆- Compound A-2 (20 mg/kg IV 2x weekly)
-□- Cisplatin (3 mg/kg IV 2x weekly)
-△- Cisplatin (3 mg/kg IV q7d) + Compound A-2 (10 mg/kg IV (+14 h) 2x weekly)
-▽- Cisplatin (3 mg/kg IV q7d) + Compound A-2 (10 mg/kg IV (+24 h) 2x weekly)
-◇- Cisplatin (3 mg/kg IV q7d) + Compound A-2 (10 mg/kg IV (+48 h) 2x weekly)

Optimization of Intravenous Compound A-2 Dose Schedule in Combination With Cisplatin In Vivo

Duration of Progression-Free Survival From Start of Treatment

METHOD FOR TREATING CANCER USING A COMBINATION OF DNA DAMAGING AGENTS AND ATR INHIBITORS

BACKGROUND OF THE INVENTION

Cancers as a group account for approximately 13% of all deaths each year with the most common being: lung cancer (1.4 million deaths), stomach cancer (740,000 deaths), liver cancer (700,000 deaths), colorectal cancer (610,000 deaths), and breast cancer (460,000 deaths). The three most common childhood cancers are leukemia (34%), brain tumors (23%), and lymphomas (12%). Rates of childhood cancer have increased by 0.6% per year between 1975 to 2002 in the United States and by 1.1% per year between 1978 and 1997 in Europe. This makes invasive cancer the leading cause of death in the developed world and the second leading cause of death in the developing world. Accordingly, there is a need to identify novel and efficacious therapeutic strategies that mitigate the limitations of current anti-cancer drugs.

SUMMARY OF THE INVENTION

The present disclosure is based, at least in part, on the unexpected discovery that ATR inhibitors administered about 12-48 hours after DNA damaging agents are particularly effective at treating proliferative diseases. Accordingly, aspects of the disclosure relate to a method of treating a proliferative disorder, such as cancer, in a subject, the method comprising administering to a subject in need thereof a DNA damaging agent and between about 12-48 hours later administering to the subject a compound that inhibits ATR protein kinase.

In some embodiments, said DNA-damaging agent is selected from the group consisting of chemotherapy and radiation treatment. In some embodiments, said DNA-damaging agent is independently selected from the group consisting of ionizing radiation, radiomimetic neocarzinostatin, a platinating agent, a Topo I inhibitor, a Topo II inhibitor, an antimetabolite, an alkylating agent (e.g., alkyl sulphonate), and an antibiotic.

In some embodiments, said DNA-damaging agent is a platinating agent selected from the group consisting of Cisplatin, Oxaliplatin, Carboplatin, Nedaplatin, Lobaplatin, Triplatin Tetranitrate, Picoplatin, Satraplatin, ProLindac, and Aroplatin.

In some embodiments, said DNA-damaging agent is a Topo I inhibitor selected from the group consisting of Camptothecin, Topotecan, Irinotecan/SN38, Rubitecan, and Belotecan. In some embodiments, said DNA-damaging agent is a Topo II inhibitor selected from the group consisting of Etoposide, Daunorubicin, Doxorubicin, Aclarubicin, Epirubicin, Idarubicin, Amrubicin, Pirarubicin, Valrubicin, Zorubicin, and Teniposide.

In some embodiments, said DNA-damaging agent is an antimetabolite selected from the group consisting of Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, 6-Mercaptopurine, 5-Fluorouracil, Azacitidine, and Hydroxyurea.

In some embodiments, said DNA-damaging agent is an alkylating agent selected from the group consisting of Mechlorethamine, Cyclophosphamide, Ifosfamide, Trofosfamide, Chlorambucil, Melphalan, Prednimustine, Bendamustine, Uramustine, Estramustine, Carmustine, Lomustine, Semustine, Fotemustine, Nimustine, Ranimustine, Streptozocin, Busulfan, Mannosulfan, Treosulfan, Carboquone, ThioTEPA, Triaziquone, Triethylenemelamine, Procarbazine, Dacarbazine, Temozolomide, Altretamine, Mitobronitol, Actinomycin, Bleomycin, Mitomycin, nitrogen mustards, nitrosoureas, triazenes, alkyl sulfonates, Procarbazine, aziridines, and Plicamycin.

In some embodiments, said DNA-damaging agent is an antibiotic selected from the group consisting of Hydroxyurea, Anthracyclines, Anthracenediones, and antibiotics from the *Streptomyces* family.

In some embodiments, the proliferative disorder may be cancer, such as a solid tumor cancer. In some such embodiments, said cancer is a solid tumor cancer selected from the group consisting of lung cancer, gastrointestinal cancer, genitourinary tract cancer, liver cancer, bone cancer, nervous system cancer, gynecological cancer, skin cancer, thyroid gland cancer, and adrenal gland cancer.

In some embodiments, said cancer is a solid tumor cancer selected from the following cancers: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal:esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; Adenoid cystic carcinoma; and Adrenal glands: neuroblastoma.

In some embodiments, said cancer is non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, or ovarian cancer.

In some embodiments, said cancer is selected from the group consisting of non-small cell lung cancer, small cell lung cancer, and triple negative breast cancer.

In some embodiments, the compound that inhibits ATR is a compound represented by Formula A-I:

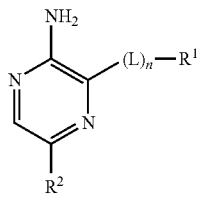

A-I or a pharmaceutically acceptable salt thereof,
wherein:
$R^1$ is a 5-6 membered monocyclic aryl or heteroaryl ring having 0-4 heteroatoms independently selected from the group consisting of nitrogen, oxygen, and sulfur, wherein said monocyclic aryl or heteroaryl ring is optionally fused to another ring to form an 8-10 membered bicyclic aryl or heteroaryl ring having 0-6 heteroatoms independently selected from the group consisting of nitrogen, oxygen, and sulfur; each $R^1$ is optionally substituted with 1-5 $J^1$ groups;
$R^2$ is a 5-6 membered monocyclic aryl or heteroaryl ring having 0-3 heteroatoms independently selected from the group consisting of nitrogen, oxygen, and sulfur, wherein said monocyclic aryl or heteroaryl ring is optionally fused to another ring to form an 8-10 membered bicyclic aryl or heteroaryl ring having 0-4 heteroatoms independently selected from the group consisting of nitrogen, oxygen, and sulfur; each $R^2$ is optionally substituted with 1-5 $J^2$ groups;
L is —C(O)NH— or —C(O)N($C_{1-6}$alkyl)-;
n is 0 or 1;
each $J^1$ and $J^2$ is independently halo, —CN, —$NO_2$, —$V^1$—R, or —$(V^2)_m$-Q;
$V^1$ is a $C_{1-10}$aliphatic chain, wherein 0-3 methylene units are optionally and independently replaced with O, NR", S, C(O), S(O), or $S(O)_2$; $V^1$ is optionally substituted with 1-6 occurrences of $J^{V1}$;
$V^2$ is a $C_{1-10}$aliphatic chain, wherein 0-3 methylene units are optionally and independently replaced with O, NR", S, C(O), S(O), or $S(O)_2$; $V^2$ is optionally substituted with 1-6 occurrences of $J^{V2}$;
m is 0 or 1;
Q is a 3-8 membered saturated or unsaturated monocyclic ring having 0-4 heteroatoms independently selected from the group consisting of nitrogen, oxygen, and sulfur, or a 9-10 membered saturated or unsaturated bicyclic ring having 0-6 heteroatoms independently selected from the group consisting of nitrogen, oxygen, and sulfur; each Q is optionally substituted with 0-5 $J^Q$;
each $J^{V1}$ or $J^{V2}$ is independently halogen, CN, $NH_2$, $NO_2$, $C_{1-4}$aliphatic, NH($C_{1-4}$aliphatic), N($C_{1-4}$aliphatic)$_2$, OH, O($C_{1-4}$aliphatic), $CO_2$H, $CO_2$($C_{1-4}$aliphatic), C(O)$NH_2$, C(O)NH($C_{1-4}$aliphatic), C(O)N($C_{1-4}$aliphatic)$_2$, NHCO($C_{1-4}$aliphatic), N($C_{1-4}$aliphatic)CO($C_{1-4}$aliphatic), $SO_2$($C_{1-4}$aliphatic), $NHSO_2$($C_{1-4}$aliphatic), or N($C_{1-4}$aliphatic)$SO_2$($C_{1-4}$aliphatic), wherein said $C_{1-4}$aliphatic is optionally substituted with halo;
R is H or $C_{1-6}$aliphatic, wherein said $C_{1-6}$aliphatic is optionally substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2$H, $CO_2$($C_{1-4}$aliphatic), CO($C_{1-4}$aliphatic), O(halo$C_{1-4}$aliphatic), or halo$C_{1-4}$aliphatic;
each $J^Q$ is independently halo, oxo, CN, $NO_2$, X—R, or —$(X)_p$-$Q^4$;
p is 0 or 1;
X is $C_{1-10}$aliphatic, wherein 1-3 methylene units of said $C_{1-6}$aliphatic are optionally replaced with —NR, —O—, —S—, C(O), $S(O)_2$, or S(O); wherein X is optionally and independently substituted with 1-4 occurrences of $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, CO($C_{1-4}$aliphatic), $CO_2$H, $CO_2$($C_{1-4}$aliphatic), C(O)$NH_2$, C(O)NH($C_{1-4}$aliphatic), C(O)N($C_{1-4}$aliphatic)$_2$, SO($C_{1-4}$aliphatic), $SO_2$($C_{1-4}$aliphatic), $SO_2$NH($C_{1-4}$aliphatic), $SO_2$N($C_{1-4}$aliphatic)$_2$, NHC(O)($C_{1-4}$aliphatic), N($C_{1-4}$aliphatic)C(O)($C_{1-4}$aliphatic), wherein said $C_{1-4}$aliphatic is optionally substituted with 1-3 occurrences of halo;
$Q^4$ is a 3-8 membered saturated or unsaturated monocyclic ring having 0-4 heteroatoms independently selected from the group consisting of nitrogen, oxygen, and sulfur, or a 8-10 membered saturated or unsaturated bicyclic ring having 0-6 heteroatoms independently selected from the group consisting of nitrogen, oxygen, and sulfur; each $Q^4$ is optionally substituted with 1-5 $J^{Q4}$;
$J^{Q4}$ is halo, CN, or $C_{1-4}$alkyl, wherein up to 2 methylene units are optionally replaced with O, NR*, S, C(O), S(O), or $S(O)_2$;
R is H or $C_{1-4}$alkyl wherein said $C_{1-4}$alkyl is optionally substituted with 1-4 halo;
R" and R* are each independently H, $C_{1-4}$alkyl, or is absent, wherein said $C_{1-4}$alkyl is optionally substituted with 1-4 halo;
wherein the proliferative disorder has one or more defects in the ATM signaling pathway.

In some embodiments, the compound that inhibits ATR is a compound represented by Formula A-1:

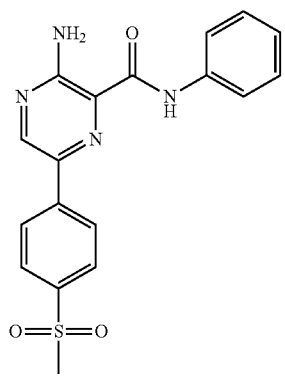

A-1 or a pharmaceutically acceptable salt thereof.

In some embodiments, the compound that inhibits ATR is a compound represented by Formula A-I-a:

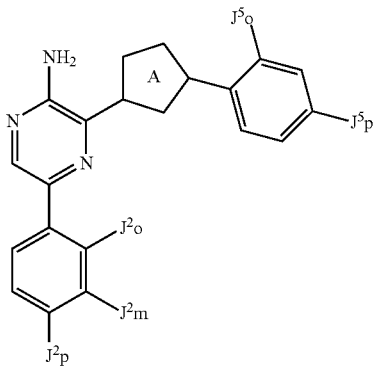

A-I-a or a pharmaceutically acceptable salt thereof, wherein:
Ring A is

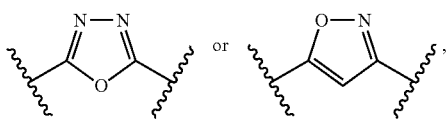 [SMILES: *c1nnc(*)o1 ; *c1cc(*)on1]

$J^5o$ is H, F, Cl, $C_{1-4}$aliphatic, $O(C_{1-3}$aliphatic), or OH;
$J^5p$ is

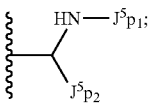

$J^5p1$ is H, $C_{1-4}$aliphatic, oxetanyl, tetrahydrofuranyl, tetrahydropyrany, wherein $J^5p1$ is optionally substituted with 1-2 occurrences of OH or halo;
$J^5p2$ is H, methyl, ethyl, $CH_2F$, $CF_3$, or $CH_2OH$;
$J^2o$ is H, CN, or $SO_2CH_3$;
$J^2m$ is H, F, Cl, or methyl;
$J^2p$ is $-SO_2(C_{1-6}$alkyl), $-SO_2(C_{3-6}$cycloalkyl), $-SO_2$(4-6 membered heterocyclyl), $-SO_2(C_{1-4}$alkyl)N$(C_{1-4}$alkyl)$_2$, or $-SO_2(C_{1-4}$alkyl)-(4-6 membered heterocyclyl), wherein said heterocyclyl contains 1 heteroatom selected from the group consisting of oxygen, nitrogen, and sulfur, and wherein said $J^2p$ is optionally substituted with 1-3 occurrences halo, OH, or $O(C_{1-4}$alkyl).
In some embodiments, Ring A is

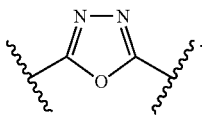 [SMILES: *c1nnc(*)o1]

In some embodiments, Ring A is

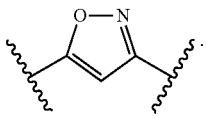 [SMILES: *c1cc(*)on1]

In some embodiments, the compound that inhibits ATR is a compound represented by Formula A-2:

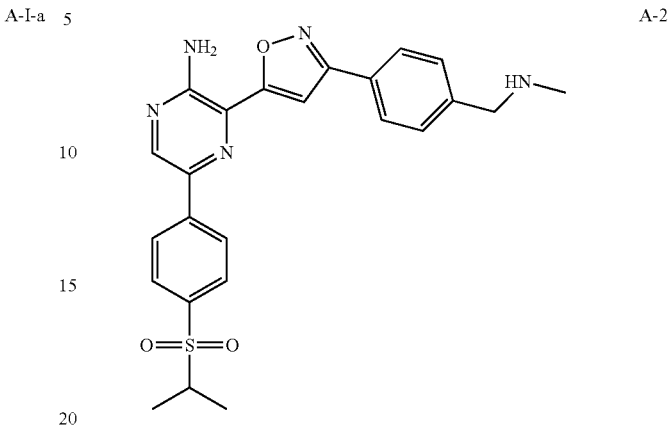

A-2 or a pharmaceutically acceptable salt thereof.
In some embodiments, the compound that inhibits ATR is a compound represented by Formula A-II:

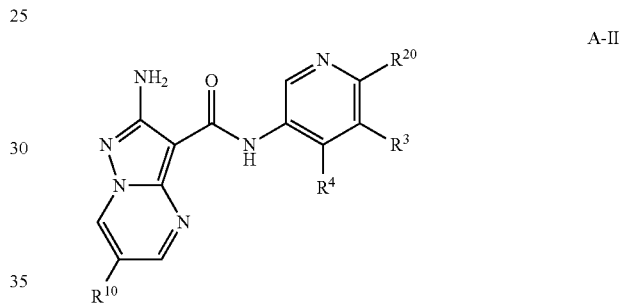

A-II or a pharmaceutically salt thereof,
wherein:
$R^{10}$ is fluoro, chloro, or $-C(J^{10})_2CN$;
$J^{10}$ is independently H or $C_{1-2}$alkyl; or
two occurrences of $J^{10}$, together with the carbon atom to which they are attached, form a 3-4 membered optionally substituted carbocyclic ring;
$R^{20}$ is H, halo, $-CN$, $NH_2$, a $C_{1-2}$alkyl optionally substituted with 0-3 occurrences of fluoro, or a $C_{1-3}$aliphatic chain, wherein up to two methylene units of the aliphatic chain are optionally replaced with $-O-$, $-NR^a-$, $-C(O)-$, or $-S(O)_z$;
$R^3$ is H, halo, $C_{1-4}$alkyl optionally substituted with 1-3 occurrences of halo, $C_{3-4}$cycloalkyl, $-CN$, or a $C_{1-3}$aliphatic chain, wherein up to two methylene units of the aliphatic chain are optionally replaced with $-O-$, $-NR^a-$, $-C(O)-$, or $-S(O)_z$;
$R^4$ is $Q^1$ or a $C_{1-10}$aliphatic chain, wherein up to four methylene units of the aliphatic chain are optionally replaced with $-O-$, $-NR^a-$, $-C(O)-$, or $-S(O)_z-$; each $R^4$ is optionally substituted with 0-5 occurrences of $J^{Q1}$; or
$R^3$ and $R^4$, taken together with the atoms to which they are bound, form a 5-6 membered aromatic or non-aromatic ring having 0-2 heteroatoms selected from the group consisting of oxygen, nitrogen, and sulfur; the ring formed by $R^3$ and $R^4$ is optionally substituted with 0-3 occurrences of $J^Z$;
$Q^1$ is a 3-7 membered fully saturated, partially unsaturated, or aromatic monocyclic ring, the 3-7 membered ring having 0-3 heteroatoms selected from the group consisting of oxygen, nitrogen, and sulfur; or an 7-12 membered fully saturated, partially unsaturated, or aromatic bicyclic ring having 0-5 heteroatoms selected from the group consisting of oxygen, nitrogen, and sulfur;

$J^Z$ is independently $C_{1-6}$aliphatic, =O, halo, or →O;

$J^{Q1}$ is independently -CN; halo; =O; $Q^2$; or a $C_{1-8}$aliphatic chain, wherein up to three methylene units of the aliphatic chain are optionally replaced with —O—, —$NR^a$—, —C(O)—, or —S(O)$_z$—; each occurrence of $J^{Q1}$ is optionally substituted by 0-3 occurrences of $J^R$; or two occurrences of $J^{Q1}$ on the same atom, taken together with the atom to which they are joined, form a 3-6 membered ring having 0-2 heteroatoms selected from the group consisting of oxygen, nitrogen, and sulfur; wherein the ring formed by two occurrences of $J^{Q1}$ is optionally substituted with 0-3 occurrences of $J^X$; or two occurrences of $J^{Q1}$, together with $Q^1$, form a 6-10 membered saturated or partially unsaturated bridged ring system;

$Q^2$ is independently a 3-7 membered fully saturated, partially unsaturated, or aromatic monocyclic ring having 0-3 heteroatoms selected from the group consisting of oxygen, nitrogen, a sulfur; or an 7-12 membered fully saturated, partially unsaturated, or aromatic bicyclic ring having 0-5 heteroatoms selected from the group consisting of oxygen, nitrogen, and sulfur;

$J^R$ is independently —CN; halo; =O; →O; $Q^3$; or a $C_{1-6}$aliphatic chain, wherein up to three methylene units of the aliphatic chain are optionally replaced with —O—, —$NR^a$—, —C(O)—, or —S(O)$_z$—; each $J^R$ is optionally substituted with 0-3 occurrences of $J^T$; or two occurrences of $J^R$ on the same atom, together with the atom to which they are joined, form a 3-6 membered ring having 0-2 heteroatoms selected from the group consisting of oxygen, nitrogen, and sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from the group consisting of oxygen, nitrogen, and sulfur; or an 7-12 membered fully saturated, partially unsaturated, or aromatic bicyclic ring having 0-5 heteroatoms selected from the group consisting of oxygen, nitrogen, and sulfur;

$J^X$ is independently —CN; =O; halo; or a $C_{1-4}$aliphatic chain, wherein up to two methylene units of the aliphatic chain are optionally replaced with —O—, —$NR^a$—, —C(O)—, or —S(O)$_z$—;

$J^T$ is independently halo, —CN; →O; =O; —OH; a $C_{1-6}$aliphatic chain, wherein up to two methylene units of the aliphatic chain are optionally replaced with —O—, —$NR^a$—, —C(O)—, or —S(O)$_z$—; or a 3-6 membered non-aromatic ring having 0-2 heteroatoms selected from the group consisting of oxygen, nitrogen, and sulfur; each occurrence of $J^T$ is optionally substituted with 0-3 occurrences of $J^M$; or two occurrences of $J^T$ on the same atom, together with the atom to which they are joined, form a 3-6 membered ring having 0-2 heteroatoms selected from the group consisting of oxygen, nitrogen, and sulfur; or two occurrences of $J^T$, together with $Q^3$, form a 6-10 membered saturated or partially unsaturated bridged ring system;

$J^M$ is independently halo or $C_{1-6}$aliphatic;

z is 0, 1 or 2; and $R^a$ is independently H or $C_{1-4}$aliphatic.

In some embodiments, $R^1$ and $R^3$ are fluoro. In some embodiments, $R^4$ is $Q^1$. In some embodiments, $Q^1$ is independently piperidinyl and imidazolyl.

In some embodiments, the compound that inhibits ATR is a compound represented by Formula A-3:

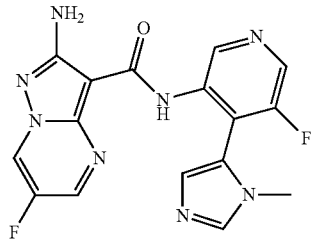

A-3 or a pharmaceutically acceptable salt thereof.

In some embodiments, the compound that inhibits ATR is a compound represented by Formula A-II-a:

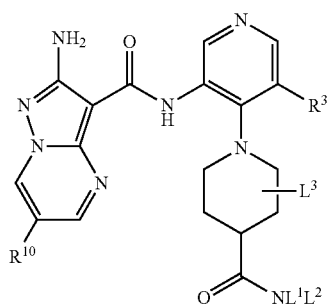

A-II-a or a pharmaceutically acceptable salt thereof, wherein:

$R^{10}$ is fluoro, chloro, or —C($J^{10}$)$_2$CN;

$J^{10}$ is independently H or $C_{1-2}$alkyl; or two occurrences of $J^1$, together with the carbon atom to which they are attached, form an optionally substituted 3-4 membered carbocyclic ring;

$R^3$ is independently H, chloro, fluoro, $C_{1-4}$alkyl optionally substituted with 1-3 occurrences of halo, $C_{3-4}$cycloalkyl, —CN, or a $C_{1-3}$aliphatic chain, wherein up to two methylene units of the aliphatic chain are optionally replaced with —O—, —$NR^a$—, —C(O)—, or —S(O)$_z$;

$L^1$ is H; a 3-7 membered aromatic or non-aromatic ring having 0-2 heteroatoms selected from selected from the group consisting of oxygen, nitrogen, and sulfur; or a $C_{1-6}$aliphatic chain, wherein up to two methylene units of the aliphatic chain are optionally replaced with —O—, —$NR^a$—, —C(O)—, or —S(O)$_z$; each $L^1$ is optionally substituted with $C_{1-4}$aliphatic, —CN, halo, —OH, or a 3-6 membered non-aromatic ring having 0-2 heteroatoms selected from the group consisting oxygen, nitrogen, and sulfur;

$L^2$ is H; a 3-7 membered aromatic or non-aromatic ring having 0-2 heteroatoms selected from the group consisting oxygen, nitrogen, and sulfur; or a $C_{1-6}$aliphatic chain, wherein up to two methylene units of the aliphatic chain are optionally replaced with —O—, —$NR^a$—, —C(O)—, or —S(O)$_z$; each $L^2$ is optionally substituted with $C_{1-4}$aliphatic, —CN, halo, —OH, or a 3-6 membered non-aromatic ring having 0-2 heteroatoms selected from the group consisting oxygen, nitrogen, and sulfur; or $L^1$ and $L^2$, together with the nitrogen to which they are attached, form a Ring D; Ring D is optionally substituted with 0-5 occurrences of $J^G$;

$L^3$ is H, $C_{1-3}$aliphatic, or CN;

Ring D is independently a 3-7 membered heterocyclyl ring having 1-2 heteroatoms selected from the group consisting oxygen, nitrogen, and sulfur; or an 7-12 membered fully saturated or partially unsaturated bicyclic ring having 1-5 heteroatoms selected from the group consisting oxygen, nitrogen, and sulfur;

$J^G$ is independently halo, —CN, —N(R$^o$)$_2$; →O; a 3-6 membered carbocycyl, a 3-6 membered heterocyclyl having 1-2 heteroatoms selected from the group consisting oxygen nitrogen, and sulfur, or a C$_{1-4}$alkyl chain, wherein up to two methylene units of the alkyl chain are optionally replaced with —O—, —NR$^a$—, —C(O)—, or —S(O)$_z$; each $J^G$ is optionally substituted with 0-2 occurrences of $J^K$.

two occurrences of $J^G$ on the same atom, together with the atom to which they are joined, form a 3-6 membered ring having 0-2 heteroatoms selected from the group consisting of oxygen, nitrogen, and sulfur; or two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from the group consisting of oxygen, nitrogen, and sulfur;

z is 0, 1, or 2; and

R$^a$ and R$^o$ independently are H or C$_{1-4}$alkyl.

In some embodiments, R$^1$ and R$^3$ are fluoro.

In some embodiments, the compound that inhibits ATR is a compound represented by Formula A-4:

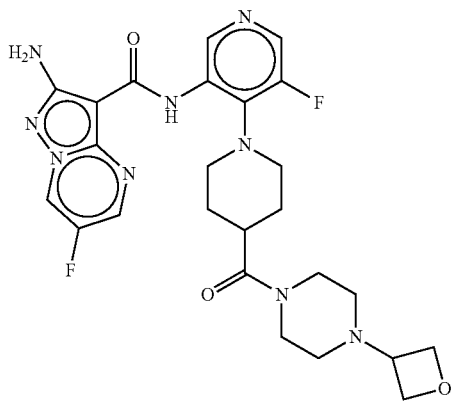

A-4 or a pharmaceutically acceptable salt thereof.

In some embodiments, the compound that inhibits ATR is:

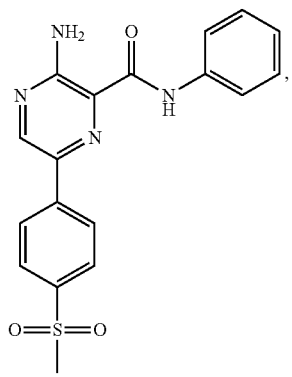

A-1

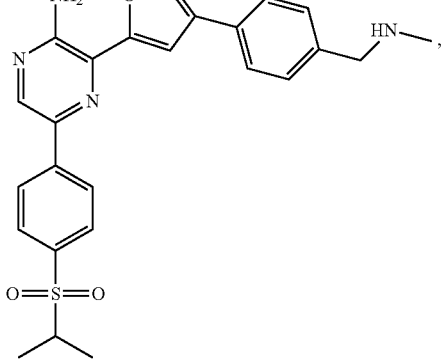

A-2

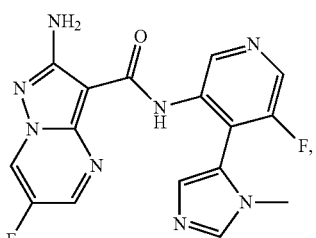

A-3

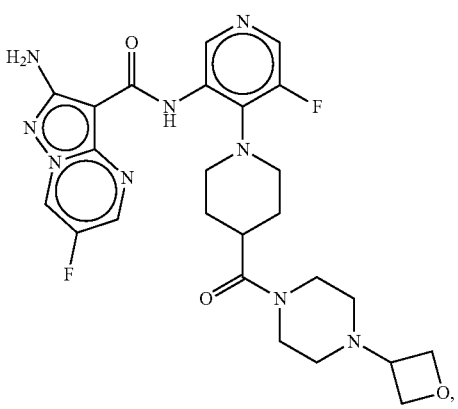

A-4 or a pharmaceutically acceptable salt thereof.

In some embodiments, a method of treating a proliferative disorder (e.g., cancer) in a subject comprises administering to the subject in need thereof a first dose of an antimetabolite and between about 12-48 hours later administering to the subject a compound that inhibits ATR protein kinase; and administering to the subject in need thereof a second dose of the antimetabolite and between about 12-48 hours later administering to the subject the compound that inhibits ATR protein kinase, wherein the second dose of the antimetabolite is administered between about 6-9 days after the first dose. In some such embodiments, the antimetabolite is selected from the group consisting of Aminopterin, Methotrexate, Pemetrexed, Raltitrexed, Pentostatin, Cladribine, Clofarabine, Fludarabine, Thioguanine, Mercaptopurine, Fluorouracil, Capecitabine, Tegafur, Carmofur, Floxuridine, Cytarabine, Gemcitabine, 6-Mercaptopurine, 5-Fluorouracil, Azacitidine and Hydroxyurea. For example, the antimetabolite may be Gemcitabine.

In some embodiments, a method of treating a proliferative disorder in a subject comprises administering to the subject in need thereof carboplatin and between about 12-24 hours later administering to the subject a compound that inhibits ATR protein kinase.

In some embodiments, a method for achieving complete response in a subject having colorectal cancer comprises administering to the subject in need thereof a compound that inhibits ATR protein kinase as a monotherapy, wherein the colorectal cancer comprises cells having a defect in ATM.

In some embodiments, a method of treating a proliferative disorder in a subject comprises administering to the subject in need thereof carboplatin and between about 12-48 hours later administering to the subject a compound represented by Formula A-2:

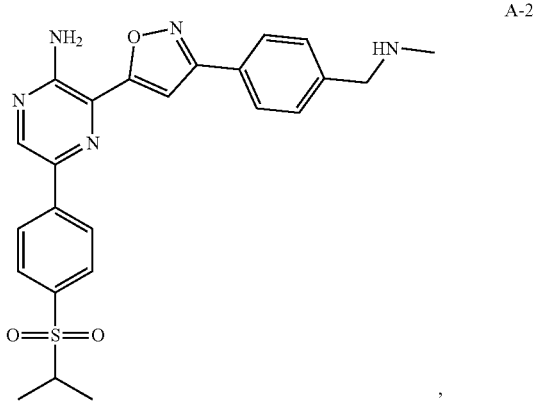 [SMILES: CNCc1ccc(-c2cc(-c3nc(-c4ccc(S(=O)(=O)C(C)C)cc4)cnc3N)on2)cc1]

A-2 or a pharmaceutically acceptable salt thereof, wherein the target AUC of carboplatin is 4 mg/mL·min or 5 mg/mL·min and wherein the dosage of a compound of Formula A-2 is 120 mg/m$^2$.

In some embodiments, a method of treating a proliferative disorder in a subject comprises administering to the subject in need thereof carboplatin and between about 12-48 hours later administering to the subject a compound represented by Formula A-2:

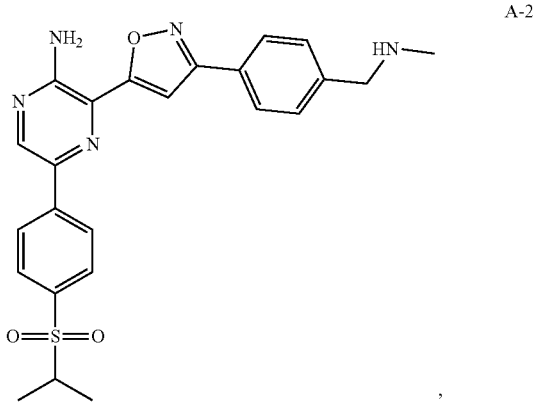 [SMILES: CNCc1ccc(-c2cc(-c3nc(-c4ccc(S(=O)(=O)C(C)C)cc4)cnc3N)on2)cc1]

A-2 or a pharmaceutically acceptable salt thereof, wherein the target AUC of carboplatin is 5 mg/mL·min and wherein the dosage of a compound of Formula A-2 is 90 mg/m$^2$.

In some embodiments, a method of treating a proliferative disorder in a subject comprises administering to the subject in need thereof a platinating agent on day 1 and between about 12-48 hours later administering to the subject a first dose of a compound that inhibits ATR protein kinase; and administering to the subject in need thereof a second dose of the compound that inhibits ATR protein kinase on day 9.

In some embodiments, a method of treating a proliferative disorder in a subject comprises administering to the subject in need thereof a DNA damaging agent and between about 12-24 hours later administering to the subject a first dose of a compound that inhibits ATR protein kinase; and administering to the subject in need thereof a second dose of the compound that inhibits ATR protein kinase between about 6 to about 9 days after administering the first dose of the compound.

In some embodiments, a method of treating a proliferative disorder in a subject comprises administering to the subject in need thereof a platinating agent and between about 12-48 hours later administering to the subject a compound that inhibits ATR protein kinase, wherein the subject is refractory to a treatment with the platinating agent.

In some embodiments, a method of treating a proliferative disorder in a subject comprises administering to the subject in need thereof a platinating agent and between about 12-48 hours later administering to the subject a compound that inhibits ATR protein kinase, wherein the subject is resistant to a treatment with the platinating agent.

In some embodiments, a method of treating a proliferative disorder in a subject comprises administering to the subject in need thereof carboplatin and a compound of Formula A-2, wherein the target AUC of carboplatin is between about 3 mg/mL·min and about 6 mg/mL·min and wherein the dosage of a compound of Formula A-2 is between about 60 mg/m$^2$ and about 240 mg/m$^2$.

In some embodiments, a method of treating a proliferative disorder in a subject comprises administering to the subject in need thereof a compound of Formula A-2, wherein the dosage of a compound of Formula A-2 is between about 120 mg/m$^2$ and about 480 mg/m$^2$.

In some embodiments, the compound that inhibits ATR is administered about 18-42 hours after administration of the DNA damaging agent. In some embodiments, the compound that inhibits ATR is administered about 20-40 hours after administration of the DNA damaging agent. In some embodiments, the compound that inhibits ATR is administered about 12-36 hours after administration of the DNA damaging agent. In some embodiments, the compound that inhibits ATR is administered about 18-36 hours after administration of the DNA damaging agent. In some embodiments, the compound that inhibits ATR is administered about 20-28 hours after administration of the DNA damaging agent. In some embodiments, the compound that inhibits ATR is administered about 24 hours after administration of the DNA damaging agent.

DETAILED DESCRIPTION OF THE INVENTION

Figure 1:
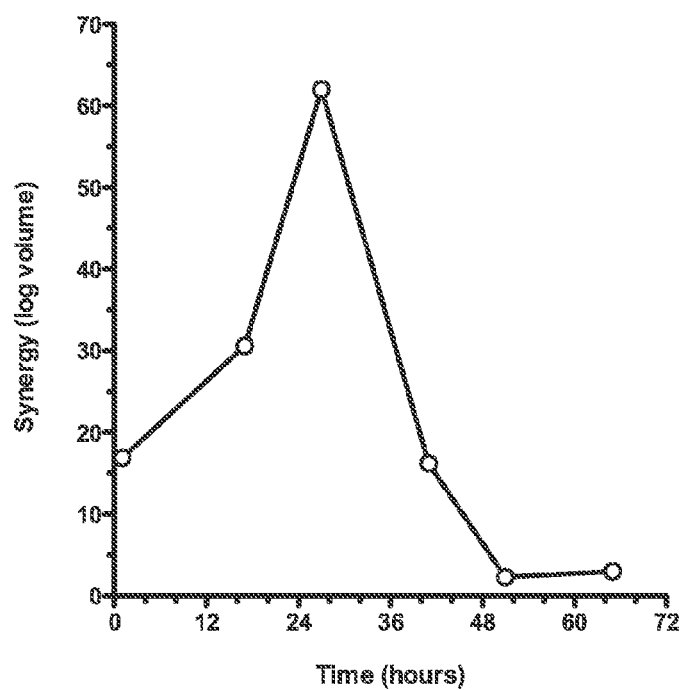
FIG. 1 shows the optimization of Compound A-2 dose schedule in vitro. PSN1 cancer cells were treated with gemcitabine for 24 hours starting at 0 hours and with Compound A-2 for 2 hours starting at 1, 17, 27, 41, 51 and 65° hours. Cell viability was measured by MTS assay at 96 hours and the data subjected to a statistical Bliss analysis using MacSynergy II software to quantitate synergy as a log volume.

The present disclosure is based, at least in part, on the unexpected discovery that ATR inhibitors administered about 12-48 hours after DNA damaging agents are particularly effective at treating proliferative diseases, such as cancer. As demonstrated in the Examples described below, it has been found that a compound of Formula A-2 (Compound A-2), an ATR inhibitor, synergized with gemcitabine and this synergistic effect markedly increased as Compound A-2 was administered progressively later through the 24 hour gemcitabine dosing period. Synergy was maximal when Compound A-2 was administered about 24 hours after starting gemcitabine treatment; later administration of Compound A-2 was less effective. No synergy was seen when Compound A-2 was administered 48 hours or later, after gemcitabine treatment was started. The strong schedule dependence is attributed to an accumulation of cells in S phase, and concomitant increase in ATR activity that occurs in response to gemcitabine treatment alone. Thus, maximal impact of Compound A-2 is expected at a time when most cells are in S phase as a result of gemcitabine treatment. Extended intervals (>48 hours) between gemcitabine therapy and Compound A-2 exposure allows DNA damage to be repaired, permitting cells to exit S phase and dramatically reducing the impact of ATR inhibition.

Without being bound by theory, it is believed that exposure of cancer cells to certain DNA-damaging agent results in sufficient DNA damage to trigger the DNA damage response and temporary S phase arrest to allow for DNA repair. The DNA damage response is believed to be regulated by two homologous protein kinases, ataxia telangiectasia (ATM) and ataxia telangiectasia Rad3-related (ATR). ATR signals to regulate DNA replication, cell cycle transitions, and DNA repair through the phosphorylation of hundreds of substrates, including checkpoint kinase 1 (Chk1). ATR inhibition during the S phase can thus block effectively the DNA damage repair in cancer cells. It is believed that offsetting treatment with a DNA damaging agent and an ATR inhibitor allows for accumulation of cells in the S phase and the concomitant increase in ATR activity due to the DNA damage response. However, a relatively long offset allows for DNA damage repair, limiting the efficacy of the ATR inhibitor. Accordingly, it is believed that effective treatment of certain cancers may be achieved by administering an ATR inhibitor between about 12 hours and about 48 hours (e.g., between about 12 hours and about 36 hours, between about 20 hours and about 28 hours, about 24 hours, or 24 hours±2 hours) after administration of a DNA-damaging agent. Moreover, administering the ATR inhibitor within the window of highest efficacy can allow efficacy and possible toxicity to be efficiently balanced.

Accordingly, aspects of the disclosure provide a method of treating a proliferative disorder in a subject, the method comprising administering to a subject in need thereof a DNA damaging agent and between about 12-48 hours later administering to the subject a compound that inhibits ATR protein kinase. In some embodiments, the compound that inhibits ATR is administered about 18-42 hours after administration of the DNA damaging agent. In some embodiments, the compound that inhibits ATR is administered about 20-40 hours after administration of the DNA damaging agent. In some embodiments, the compound that inhibits ATR is administered about 12-36 hours after administration of the DNA damaging agent. In some embodiments, the compound that inhibits ATR is administered about 18-36 hours after administration of the DNA damaging agent. In some embodiments, the compound that inhibits ATR is administered about 20-28 hours after administration of the DNA damaging agent. In some embodiments, the compound that inhibits ATR is administered about 24 hours, or 24 hours±2 hours, after administration of the DNA damaging agent. In some embodiments, said DNA-damaging agent is chemotherapy or radiation treatment.

In some embodiments in which the DNA damaging agent is given once per treatment cycle (e.g., 3 week treatment cycle, 4 week treatment cycle), the ATR inhibitor may be administered at least about 12 hours (e.g., at least about 24 hours) after the DNA damaging agent, and optionally a second dose of the ATR inhibitor may be administered at least about 5 days (e.g., at least about 6 days) after a prior (e.g., the immediately prior) administration of the ATR inhibitor. In certain embodiments in which the DNA damaging agent is given once per treatment cycle (e.g., 3 week treatment cycle, 4 week treatment cycle), the ATR inhibitor may be administered between about 12 hours and about 48 hours (e.g., between about 12 hours and about 36 hours, between about 20 hours and about 28 hours) after the DNA damaging agent, and optionally a second dose of the ATR inhibitor may be administered between about 5 days to about 9 days after a prior (e.g., the immediately prior) administration of the ATR inhibitor. For instance, in some embodiments, a DNA-damaging agent (e.g., platinating agent) may be administered on day 1 and an ATR inhibitor (e.g., a compound of Formula A-2) may be administered between about 12 hours and about 48 hours (e.g., between about 12 hours and about 36 hours, between about 20 hours and about 28 hours) later. In some such embodiments, a second dose of the ATR inhibitor (e.g., a compound of Formula A-2) may be administered between about 5 days to about 9 days after a prior (e.g., the immediately prior) administration of the ATR inhibitor.

For instance, the second dose of the ATR inhibitor may be administered after about between about 5 days and about 9 days, between about 5 days and about 8 days, between about 5 days and about 7 days, between about 6 days and about 9 days, between about 6 days and about 8 days, or between about 6 days and about 7 days. In some instances, the second dose of the ATR inhibitor may be administered after between about 6 days and about 8 days or after about 7 days. In one example, a method of treating a proliferative disorder may comprise administering a platinating agent (e.g., carboplatin, cisplatin) on day 1, a first dose of an ATR inhibitor on day 2 (e.g., a compound of Formula A-2) between about 20 hours and about 28 hours (e.g., 24 hours or 24 hours±2 hours) after administration of the platinating agent, and a second dose of the ATR inhibitor about 6 days and about 8 days (e.g., on day 9) after administration of the ATR inhibitor. The method may be part of a 3 week or 4 week treatment cycle. In some such embodiments, a DNA-damaging agent or ATR inhibitor may not be administered after the second dose of the ATR inhibitor for the remaining portion of the treatment cycle. For instance, a method of treating a proliferative disorder using a three week treatment cycle may comprise administering a platinating agent (e.g., carboplatin, cisplatin) on day 1, a first dose of an ATR inhibitor (e.g., a compound of Formula A-2) on day 2 (e.g., about 24 hours, or 24 hours±2 hours, after administration of the platinating agent) and a second dose of the ATR inhibitor on day 9. In some such embodiments, a DNA-damaging agent or ATR inhibitor may not be administered after the second dose of the ATR inhibitor for the remaining portion of the treatment cycle. In certain embodiments, a method of treating a proliferative disorder using a four week treatment cycle may comprise administering a platinating agent (e.g., carboplatin, cisplatin) on day 1, a first dose of an ATR inhibitor (e.g., a compound of Formula A-2) on day 2 (e.g., about 24 hours, or 24 hours±2 hours, after administration of the platinating agent) and a second dose of the ATR inhibitor on day 9. In some such embodiments, a DNA-damaging agent or ATR inhibitor may not be administered after the second dose of the ATR inhibitor for the remaining portion of the treatment cycle.

In some embodiments in which the DNA damaging agent is given twice per treatment cycle (e.g., 3 week treatment cycle, 4 week treatment cycle), the ATR inhibitor may be administered between about 12 hours and about 48 hours (e.g., between about 12 hours and about 36 hours, between about 20 hours and about 28 hours) after one administration of the DNA damaging agent or after each administration. In certain embodiments, a first dose of a DNA-damaging agent (e.g., antimetabolite) may be administered on day 1 and an ATR inhibitor (e.g., a compound of Formula A-2) may be administered between about 12 hours and about 48 hours (e.g., between about 12 hours and about 36 hours, between about 20 hours and about 28 hours) later. In some such embodiments, a second dose of the DNA-damaging agent (e.g., antimetabolite) may be administered between about 5 days to about 9 days after a prior (e.g., immediately prior) administration of the DNA damaging agent. For example, the second dose of the DNA-damaging agent (e.g., antimetabolite) may be administered about between about 5 days and about 9 days, between about 5 days and about 8 days, between about 5 days and about 7 days, between about 6 days and about 9 days, between about 6 days and about 8 days, or between about 6 days and about 7 days after the first dose of the DNA damaging agent. In some instances, the second dose of the DNA-damaging agent may be administered after between about 6 days and about 8 days or after about 7 days. In some embodiments, a second dose of an ATR inhibitor may be administered between about 12 hours and about 48 hours (e.g., between about 12 hours and about 36 hours, between about 20 hours and about 28 hours) after the second dose of the DNA damaging agent.

In one example, a method of treating a proliferative disorder may comprise administering a first dose of an antimetabolite (e.g., gemcitabine) on day 1, a first dose of an ATR inhibitor (e.g., a compound of Formula A-2) on day 2 between about 20 hours and about 28 hours (e.g., 24 hours or 24 hours±2 hours) after administration of the antimetabolite, and a second dose of the antimetabolite between about 6 days and about 8 days (e.g., on day 8) after the first dose of the antimetabolite. The method, in some instances, further comprises administering a second dose of an ATR inhibitor (e.g., a compound of Formula A-2) between about 20 hours and about 28 hours (e.g., 24 hours or 24 hours±2 hours) after administration of the second dose of the antimetabolite. The method may be part of a 3 week or 4 week treatment cycle. In some such embodiments, a DNA-damaging agent or ATR inhibitor may not be administered after the second dose of the antimetabolite or, when present, the second dose of the ATR inhibitor for the remaining portion of the treatment cycle. For instance, a method of treating a proliferative disorder using a 3 week treatment cycle may comprise administering a first dose of an antimetabolite (e.g., gemcitabine) on day 1, a first dose of an ATR inhibitor on day 2 (e.g., about 24 hours, or 24 hours±2 hours, after administration of the antimetabolite on day 1), and a second dose of the antimetabolite on day 8. The method, in some instances, further comprises administering a second dose of an ATR inhibitor (e.g., a compound of Formula A-2) on day 9 (e.g., about 24 hours, or 24 hours±2 hours, after administration of the second dose of the antimetabolite). In some such embodiments, a DNA-damaging agent or ATR inhibitor may not be administered after the second dose of the antimetabolite or, when present, the second dose of the ATR inhibitor for the remaining portion of the treatment cycle. In certain embodiments, a method of treating a proliferative disorder using a 4 week treatment cycle may comprise administering a first dose of an antimetabolite (e.g., gemcitabine) on day 1, a first dose of an ATR inhibitor on day 2 (e.g., about 24 hours, or 24 hours±2 hours, after administration of the antimetabolite on day 1), and a second dose of the antimetabolite on day 8. The method, in some instances, further comprises administering a second dose of an ATR inhibitor (e.g., a compound of Formula A-2) on day 9 (e.g., about 24 hours, or 24 hours±2 hours, after administration of the second dose of the antimetabolite). In some such embodiments, a DNA-damaging agent or ATR inhibitor may not be administered after the second dose of the antimetabolite or, when present, the second dose of the ATR inhibitor for the remaining portion of the treatment cycle.

In some embodiments in which the DNA damaging agent (e.g., Topo I inhibitor, Topo II inhibitor) is administered three or more times per treatment cycle (e.g., 3-5 administrations), the ATR inhibitor may be administered between about 12 hours and about 48 hours (e.g., between about 12 hours and about 36 hours, between about 20 hours and about 28 hours) after at least one administration of the DNA damaging agent (e.g., after one administration, after each of two administrations, after each of three administrations) or after each administration.

In some embodiments, two or more different DNA damaging agents may be administered within a treatment cycle (e.g., 3 week treatment cycle, 4 week treatment cycle). The DNA damaging agents may differ in mechanism of action and/or administration frequency. For instance, a first DNA-damaging agent (e.g., antimetabolite) administered twice per treatment cycle and a second DNA damaging agent (e.g., platinating agent) administered once per treatment cycle may be used. In some such embodiments, the first DNA-damaging agent and a second DNA damaging agent may be administered as described above with respect to the administration of a single DNA-damaging agent. The ATR inhibitor may be administered between about 12 hours and about 48 hours (e.g., between about 12 hours and about 36 hours, between about 20 hours and about 28 hours) after at least one DNA damaging agent (e.g., two DNA damaging agents, after each of two administrations of a DNA damaging agent.

In one example, a platinating agent and an antimetabolite (e.g., carboplatin and gemcitabine, cisplatin and gemcitabine) may be administered on day 1 and a first dose of an ATR inhibitor (e.g., a compound of Formula A-2) may be administered between about 12 hours and about 48 hours (e.g., between about 12 hours and about 36 hours, between about 20 hours and about 28 hours) after the platinating agent and the antimetabolite. In some such embodiments, a second dose of the antimetabolite may be administered between about 6 days and about 8 days (e.g., on day 8) after the first dose of the antimetabolite. The method, in some instances, further comprises administering a second dose of an ATR inhibitor (e.g., a compound of Formula A-2) between about 20 hours and about 28 hours (e.g., 24 hours or 24 hours±2 hours) after administration of the second dose of the antimetabolite. The method may be part of a 3 week or 4 week treatment cycle. In some such embodiments, a DNA-damaging agent or ATR inhibitor may not be administered after the second dose of the antimetabolite or, when present, the second dose of the ATR inhibitor for the remaining portion of the treatment cycle. In other embodiments, a third dose of the ATR inhibitor may be administered between about 6 and about 8 days after the second dose of the ATR inhibitor.

In some embodiments, a DNA damaging agent, ATR inhibitor, and an additional therapeutic agent may be administered within a treatment cycle (e.g., 3 week treatment cycle, 4 week treatment cycle). In some embodiments, the additional therapeutic agent is a chemotherapeutic agent, such as a taxane (e.g., taxol, docetaxol, cabazitaxel). For instance, a platinating agent (e.g., carboplatin, cisplatin), ATR inhibitor (e.g., a compound of Formula A-2), and taxol may be administered within a single treatment cycle (e.g., 3 week treatment cycle, 4 week treatment cycle). In some such embodiments, the DNA-damaging agent and ATR inhibitor may be administered as described herein. For instance, the ATR inhibitor may be administered between about 12 hours and about 48 hours (e.g., between about 12 hours and about 36 hours, between about 20 hours and about 28 hours) after a DNA damaging agent.

As used herein, the term "treatment cycle" has its ordinary meaning in the art and may refer to a course of treatment that is repeated on a regular schedule, including periods of rest. For example, a treatment cycle of four weeks may include administration of agents during week one followed by three weeks of rest (e.g., no treatment). In general, an ATR inhibitor may be administered at least once per treatment cycle and between about 12 hours and about 48 hours (e.g., between about 12 hours and about 36 hours, between about 20 hours and about 28 hours) after a DNA damaging agent. In some embodiments, the methods, described herein, may be part of a 3 week or 4 week treatment cycle.

In some embodiments, treatment of a proliferative disorder using the methods described herein may result in a RECIST stable disease, a RECIST partial response, or a RECIST complete response. For instance, treatment may result in a RECIST partial or a RECIST complete response. As used herein, the term "RECIST partial response" has its ordinary meaning in the art and may refer to a 30% decrease in the sum of the longest diameter of target lesions as determined according to the RECIST (i.e., Response Evaluation Criteria in Solid Tumors) guidelines version 1.1 (see Eisenhauer et. al., Eur. J. Cancer. 45 (2009) 228-247). As used herein, the term "RECIST complete response" has its ordinary meaning in the art and may refer to the disappearance of all target lesions as determined according to the RECIST guidelines version 1.1. As used herein, the term "RECIST progressive disease" has its ordinary meaning in the art and may refer to a 20% increase in the sum of the longest diameter of target lesions as determined according to the RECIST guidelines version 1.1. As used herein, the term "RECIST stable disease" has its ordinary meaning in the art and may refer to small changes that do not meet above criteria as determined according to the RECIST guidelines version 1.1.

In general, treatment of a proliferative disorder (e.g., cancer) with the methods described herein may reverse, alleviate, delaying the onset of, or inhibit the progress of the proliferative disorder. In some embodiments, the methods described herein may decrease the sum of the longest diameter of target lesions, decrease the sum of the longest diameter of non-target lesions, and/or decrease tumor burden by at least about 10%, at least about 20%, at least about 30%, at least about 40%, at least about 50%, or at least about 60%. In certain embodiments, the methods described herein may decrease the sum of the longest diameter of target lesions, decrease the sum of the longest diameter of non-target lesions, and/or decrease tumor burden by between about 20% and about 60% or between about 40% and about 60%.

In some embodiments, the methods described herein may be particularly advantageous for the treatment of proliferative disorders in subjects that are refractory, resistant, or sensitive to one or more DNA damaging. In certain embodiments, the methods described herein may be used to treat a proliferative disorder (e.g., ovarian cancer, lung cancer, colorectal cancer, breast cancer) in a subject that is refractory to a platinating agent (e.g., cisplatin, carboplatin). In certain embodiments, the methods described herein may be used to treat a proliferative disorder (e.g., ovarian cancer, lung cancer, breast cancer) in a subject that is refractory to an antimetabolite (e.g., gemcitabine). For example, as described in more detail in the Examples, it was surprisingly found that treatment of a human subject having metastatic high grade serous ovarian cancer having gBRCA1 and TP53 mutations with peritoneal, liver and nodal disease that was refractory to carboplatin and gemcitabine had a RECIST partial response after treatment with carboplatin and a compound of Formula A-2 as described herein.

In certain embodiments, the methods described herein may be used to treat a proliferative disorder (e.g., ovarian cancer, lung cancer, colorectal cancer, breast cancer) in a subject that is resistant to a platinating agent (e.g., cisplatin, carboplatin). In certain embodiments, the methods described herein may be used to treat a proliferative disorder (e.g., ovarian cancer, lung cancer) in a subject that is resistant to an antimetabolite (e.g., gemcitabine). In certain embodiments, the methods described herein may be used to treat a proliferative disorder (e.g., ovarian cancer, lung cancer, breast cancer, colorectal cancer) in a subject that is sensitive to a platinating agent (e.g., cisplatin, carboplatin). In certain embodiments, the methods described herein may be used to treat a proliferative disorder (e.g., ovarian cancer, lung cancer breast cancer, colorectal cancer) in a subject that is sensitive to an antimetabolite (e.g., gemcitabine). For example, as described in more detail in the Examples, it was surprisingly found that treatment of a human subject, who was a BRCA2 W2626Q (8106 C>G) carrier, having CA 125 positive ovarian cancer that was resistant to carboplatin had a RECIST partial response after treatment with cisplatin and a compound of Formula A-2 as described herein.

As used herein, the terms "refractory" has its ordinary meaning in the art and may refer to a proliferative disorder that progresses during treatment with an agent (e.g., DNA damaging agent) (first line treatment). As used herein, the terms "resistant" has its ordinary meaning in the art and may refer to a proliferative disorder that recurs within a certain period of time after completing treatment with an agent (e.g., DNA damaging agent). As used herein, the terms "sensitive" has its ordinary meaning in the art and may refer to a proliferative disorder that recurs after a certain period of time from completing treatment with an agent (e.g., DNA damaging agent). In general, recurrence occurs after a longer period of time for a sensitive cancer than for a resistant cancer. The periods of time to classify a proliferative disorder as resistance or sensitive would be known to those of ordinary skill in the art and may depend on certain factors, such as the type of cancer, the treatment used, and the stage of cancer, amongst others. For instance, resistant ovarian cancer may refer to ovarian cancer that recurs within 6 months from completing treatment. Sensitive ovarian cancer may refer to ovarian cancer that recurs after greater than 6 months from completing treatment. For instance, resistant small cell lung cancer (SCLC) may refer to SCLC that recurs within 3 months from completing treatment. Sensitive SCLC may refer to SCLC that recurs after greater than 3 months from completing treatment.

In some embodiments, the methods described herein may be particularly advantageous for the treatment of proliferative disorders having a defect in the ATM signaling cascade. In some embodiments, the defect is altered expression or activity of one or more of the following: ATM and p53. In certain embodiments, the proliferative disorder may have a mutation (e.g., somatic) in p53. For example, treatment of a proliferative disorder (e.g., ovarian cancer) having a somatic mutation in the TP53 gene by administering a platinating agent (e.g., carboplatin, cisplatin) on day 1, a first dose of an ATR inhibitor (e.g., a compound of Formula A-2) between about 20 hours and about 28 hours (e.g., 24 hours or 24 hours±2 hours) after administration of the platinating agent on day 1, and a second dose of the ATR inhibitor between about 6 days and about 8 days (e.g., on day 9) after the first dose, as part of a three or four week treatment cycle including a rest period after the second dose of the ATR inhibitor, may result in at least a RECIST partial response. In some such embodiments, the methods described herein may decrease the sum of the longest diameter of target lesions, decrease the sum of the longest diameter of non-target lesions, and/or decrease tumor burden by between about 20% and about 60% or between about 40% and about 60%.

In some embodiments, the proliferative disorder may have a complete loss of ATM signaling. For example, treatment of a proliferative disorder (e.g., colorectal cancer) having a complete loss of ATM signaling with a monotherapy (e.g., at a dosage of about 60 mg/m², between about 60 mg/m² and about 480 mg/m², about 120 mg/m², about 240 mg/m², about 480 mg/m²) or a combination therapy with a DNA damaging agent, as described herein may result in a decrease in the sum of the longest diameter of target lesions, decrease in the sum of the longest diameter of non-target lesions, and/or decrease in tumor burden by at least about 80% or RECIST complete response.

Compounds

In some aspects of the present disclosure, the compound that inhibits ATR protein kinase is a compound represented by Formula A-I:

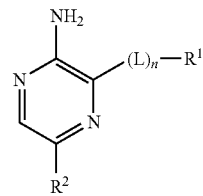

or a pharmaceutically acceptable salt thereof,
wherein:
$R^1$ is a 5-6 membered monocyclic aryl or heteroaryl ring having 0-4 heteroatoms independently selected from the group consisting of nitrogen, oxygen, and sulfur, wherein said monocyclic aryl or heteroaryl ring is optionally fused to another ring to form an 8-10 membered bicyclic aryl or heteroaryl ring having 0-6 heteroatoms independently selected from the group consisting of nitrogen, oxygen, and sulfur; each $R^1$ is optionally substituted with 1-5 $J^1$ groups;

$R^2$ is a 5-6 membered monocyclic aryl or heteroaryl ring having 0-3 heteroatoms independently selected from the group consisting of nitrogen, oxygen, and sulfur, wherein said monocyclic aryl or heteroaryl ring is optionally fused to another ring to form an 8-10 membered bicyclic aryl or heteroaryl ring having 0-4 heteroatoms independently selected from the group consisting of nitrogen, oxygen, and sulfur; each $R^2$ is optionally substituted with 1-5 $J^2$ groups;

L is —C(O)NH— or —C(O)N($C_{1-6}$alkyl)-;
n is 0 or 1;
each $J^1$ and $J^2$ is independently halo, —CN, —NO$_2$, —V$^1$—R, or —(V$^2$)$_m$-Q;
$V^1$ is a $C_{1-10}$aliphatic chain, wherein 0-3 methylene units are optionally and independently replaced with O, NR", S, C(O), S(O), or S(O)$_2$; $V^1$ is optionally substituted with 1-6 occurrences of $J^{V1}$;
$V^2$ is a $C_{1-10}$aliphatic chain, wherein 0-3 methylene units are optionally and independently replaced with O, NR", S, C(O), S(O), or S(O)$_2$; $V^2$ is optionally substituted with 1-6 occurrences of $J^{V2}$;
m is 0 or 1;
Q is a 3-8 membered saturated or unsaturated monocyclic ring having 0-4 heteroatoms independently selected from the group consisting of nitrogen, oxygen, and sulfur, or a 9-10 membered saturated or unsaturated bicyclic ring having 0-6 heteroatoms independently selected from the group consisting of nitrogen, oxygen, and sulfur; each Q is optionally substituted with 0-5 $J^Q$;
each $J^{V1}$ or $J^{V2}$ is independently halogen, CN, NH$_2$, NO$_2$, $C_{1-4}$aliphatic, NH($C_{1-4}$aliphatic), N($C_{1-4}$aliphatic)$_2$, OH, O($C_{1-4}$aliphatic), CO$_2$H, CO$_2$($C_{1-4}$aliphatic), C(O)NH$_2$, C(O)NH($C_{1-4}$aliphatic), C(O)N($C_{1-4}$aliphatic)$_2$, NHCO($C_{1-4}$aliphatic), N($C_{1-4}$aliphatic)CO($C_{1-4}$aliphatic), SO$_2$($C_{1-4}$aliphatic), NHSO$_2$($C_{1-4}$aliphatic), or N($C_{1-4}$aliphatic)SO$_2$($C_{1-4}$aliphatic), wherein said $C_{1-4}$aliphatic is optionally substituted with halo;
R is H or $C_{1-6}$aliphatic, wherein said $C_{1-6}$aliphatic is optionally substituted with 1-4 occurrences of NH$_2$, NH($C_{1-4}$aliphatic), N($C_{1-4}$aliphatic)$_2$, halogen, $C_{1-4}$aliphatic, OH, O($C_{1-4}$aliphatic), NO$_2$, CN, CO$_2$H, CO$_2$($C_{1-4}$aliphatic), CO($C_{1-4}$aliphatic), O(halo$C_{1-4}$aliphatic), or halo$C_{1-4}$aliphatic;
each $J^Q$ is independently halo, oxo, CN, NO$_2$, X—R, or —(X)$_p$-Q$^4$;

p is 0 or 1;

X is $C_{1-10}$aliphatic, wherein 1-3 methylene units of said $C_{1-6}$aliphatic are optionally replaced with —NR, —O—, —S—, C(O), S(O)$_2$, or S(O); wherein X is optionally and independently substituted with 1-4 occurrences of NH$_2$, NH($C_{1-4}$aliphatic), N($C_{1-4}$aliphatic)$_2$, halogen, $C_{1-4}$aliphatic, OH, O($C_{1-4}$aliphatic), NO$_2$, CN, CO($C_{1-4}$aliphatic), CO$_2$H, CO$_2$($C_{1-4}$aliphatic), C(O)NH$_2$, C(O)NH($C_{1-4}$aliphatic), C(O)N($C_{1-4}$aliphatic)$_2$, SO($C_{1-4}$aliphatic), SO$_2$($C_{1-4}$aliphatic), SO$_2$NH($C_{1-4}$aliphatic), SO$_2$N($C_{1-4}$aliphatic)$_2$, NHC(O)($C_{1-4}$aliphatic), N($C_{1-4}$aliphatic)C(O)($C_{1-4}$aliphatic), wherein said $C_{1-4}$aliphatic is optionally substituted with 1-3 occurrences of halo;

$Q^4$ is a 3-8 membered saturated or unsaturated monocyclic ring having 0-4 heteroatoms independently selected from the group consisting of nitrogen, oxygen, and sulfur, or a 8-10 membered saturated or unsaturated bicyclic ring having 0-6 heteroatoms independently selected from the group consisting of nitrogen, oxygen, and sulfur; each $Q^4$ is optionally substituted with 1-5 $J^{Q4}$;

$J^{Q4}$ is halo, CN, or $C_{1-4}$alkyl, wherein up to 2 methylene units are optionally replaced with O, NR*, S, C(O), S(O), or S(O)$_2$;

R is H or $C_{1-4}$alkyl, wherein said $C_{1-4}$alkyl is optionally substituted with 1-4 halo;

R" and R* are each independently H, $C_{1-4}$alkyl, or is absent; wherein said $C_{1-4}$alkyl is optionally substituted with 1-4 halo.

In some embodiments, L is —C(O)NH—; and $R^1$ and $R^2$ are phenyl.

In another embodiment the compound that inhibits ATR kinase is a compound represented by Formula A-I-a:

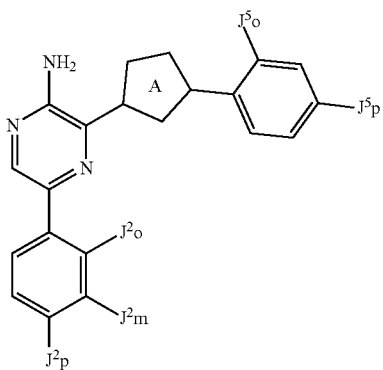

A-I-a or a pharmaceutically salt thereof,
wherein:
Ring A is

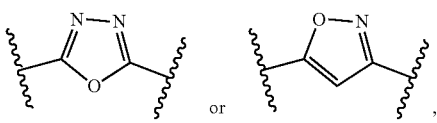 [SMILES: *c1nnc(*)o1 ; *c1cc(*)on1]

$J^5$o is H, F, Cl, $C_{1-4}$aliphatic, O($C_{1-3}$aliphatic), or OH;
$J^5$p is

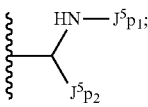

$J^5p_1$ is H, $C_{1-4}$aliphatic, oxetanyl, tetrahydrofuranyl, tetrahydropyranyl; wherein $J^5p_1$ is optionally substituted with 1-2 occurrences of OH or halo;

$J^5p_2$ is H, methyl, ethyl, CH$_2$F, CF$_3$, or CH$_2$OH;

$J^2$o is H, CN, or SO$_2$CH$_3$;

$J^2$m is H, F, Cl, or methyl;

$J^2$p is —SO$_2$($C_{1-6}$alkyl), —SO$_2$($C_{3-6}$cycloalkyl), —SO$_2$(4-6 membered heterocyclyl), —SO$_2$($C_{1-4}$alkyl)N($C_{1-4}$alkyl)$_2$, or —SO$_2$($C_{1-4}$alkyl)-(4-6 membered heterocyclyl), wherein said heterocyclyl contains 1 heteroatom selected from the group consisting of oxygen, nitrogen, and sulfur; and wherein said $J^2$p is optionally substituted with 1-3 occurences halo, OH, or O($C_{1-4}$alkyl).

In some embodiments, Ring A is

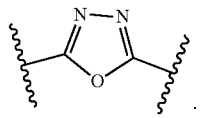 [SMILES: *c1nnc(*)o1]

In other embodiments, Ring A is

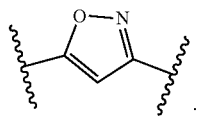 [SMILES: *c1cc(*)on1]

In some embodiments, the compound that inhibits ATR kinase is a compound represented by Formula A-1:

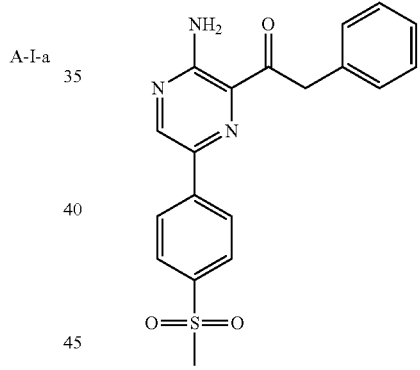

A-1 or a pharmaceutically acceptable salt thereof, or a compound represented by Formula A-2:

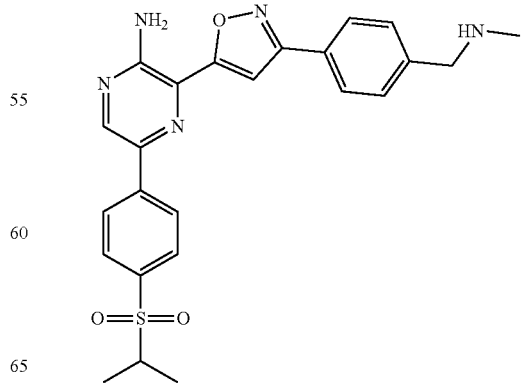

A-2 or a pharmaceutically acceptable salt thereof.

In certain embodiments, the compound that inhibits ATR kinase is a compound represented by Formula A-1:

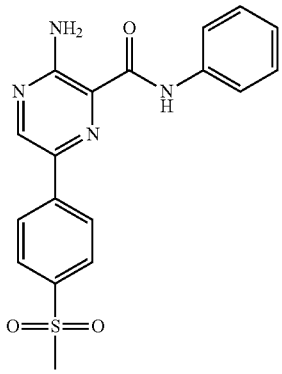

A-1 or a pharmaceutically acceptable salt thereof.

In another embodiment, the compound that inhibits ATR kinase is a compound represented by Formula A-2:

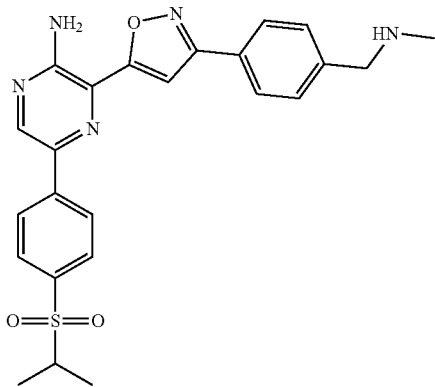

A-2 or a pharmaceutically acceptable salt thereof.

In another aspect of the present disclosure, the compound that inhibits ATR protein kinase is represented by Formula A-II:

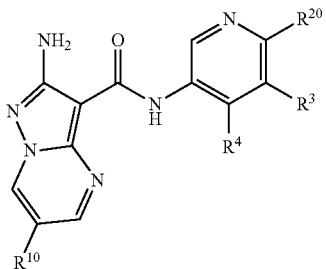

A-II or a pharmaceutically salt or derivative thereof, wherein:
$R^{10}$ is selected from fluoro, chloro, or —C($J^{10}$)$_2$CN;
$J^{10}$ is independently H or $C_{1-2}$alkyl; or
two occurrences of $J^{10}$, together with the carbon atom to which they are attached, form a 3-4 membered optionally substituted carbocyclic ring;

$R^{20}$ is H, halo, —CN, NH$_2$, a $C_{1-2}$alkyl optionally substituted with 0-3 occurrences of fluoro; or a $C_{1-3}$aliphatic chain, wherein up to two methylene units of the aliphatic chain are optionally replaced with —O—, —NR$^a$—, —C(O)—, or —S(O)$_z$;

$R^3$ is H, halo, $C_{1-4}$alkyl optionally substituted with 1-3 occurrences of halo, $C_{3-4}$cycloalkyl, —CN, or a $C_{1-3}$aliphatic chain, wherein up to two methylene units of the aliphatic chain are optionally replaced with —O—, —NR$^a$—, —C(O)—, or —S(O)$_z$;

$R^4$ is $Q^1$ or a $C_{1-10}$aliphatic chain, wherein up to four methylene units of the aliphatic chain are optionally replaced with —O—, —NR$^a$—, —C(O)—, or —S(O)$_z$—; each $R^4$ is optionally substituted with 0-5 occurrences of $J^{Q1}$; or $R^3$ and $R^4$, taken together with the atoms to which they are bound, form a 5-6 membered aromatic or non-aromatic ring having 0-2 heteroatoms selected from the group consisting of oxygen, nitrogen, and sulfur; the ring formed by $R^3$ and $R^4$ is optionally substituted with 0-3 occurrences of $J^Z$;

$Q^1$ is a 3-7 membered fully saturated, partially unsaturated, or aromatic monocyclic ring, the 3-7 membered ring having 0-3 heteroatoms selected from the group consisting of oxygen, nitrogen, and sulfur; or an 7-12 membered fully saturated, partially unsaturated, or aromatic bicyclic ring having 0-5 heteroatoms selected from the group consisting of oxygen, nitrogen, and sulfur;

$J^Z$ is independently $C_{1-6}$aliphatic, =O, halo, or →O;

$J^{Q1}$ is independently -CN, halo, =O, $Q^2$, or a $C_{1-8}$aliphatic chain, wherein up to three methylene units of the aliphatic chain are optionally replaced with —O—, —NR$^a$—, —C(O)—, or —S(O)$_z$—; each occurrence of $J^{Q1}$ is optionally substituted by 0-3 occurrences of $J^R$; or two occurrences of $J^{Q1}$ on the same atom, taken together with the atom to which they are joined, form a 3-6 membered ring having 0-2 heteroatoms selected from the group consisting of oxygen, nitrogen, and sulfur; wherein the ring formed by two occurrences of $J^{Q1}$ is optionally substituted with 0-3 occurrences of $J^X$; or two occurrences of $J^{Q1}$, together with $Q^1$, form a 6-10 membered saturated or partially unsaturated bridged ring system;

$Q^2$ is independently selected from a 3-7 membered fully saturated, partially unsaturated, or aromatic monocyclic ring having 0-3 heteroatoms selected from oxygen, nitrogen, or sulfur; or an 7-12 membered fully saturated, partially unsaturated, or aromatic bicyclic ring having 0-5 heteroatoms selected from oxygen, nitrogen, or sulfur;

$J^R$ is independently —CN, halo, =O, →O; $Q^3$, or a $C_{1-6}$aliphatic chain, wherein up to three methylene units of the aliphatic chain are optionally replaced with —O—, —NR$^a$—, —C(O)—, or —S(O)$_z$—; each $J^R$ is optionally substituted with 0-3 occurrences of $J^T$; or two occurrences of $J^R$ on the same atom, together with the atom to which they are joined, form a 3-6 membered ring having 0-2 heteroatoms selected from oxygen, nitrogen, or sulfur; wherein the ring formed by two occurrences of $J^R$ is optionally substituted with 0-3 occurrences of $J^X$; or two occurrences of $J^R$, together with $Q^2$, form a 6-10 membered saturated or partially unsaturated bridged ring system;

$Q^3$ is a 3-7 membered fully saturated, partially unsaturated, or aromatic monocyclic ring having 0-3 heteroatoms selected from the group consisting of oxygen, nitrogen, and sulfur; or an 7-12 membered fully saturated, partially unsaturated, or aromatic bicyclic ring having 0-5 heteroatoms selected from the group consisting of oxygen, nitrogen, and sulfur;

$J^X$ is independently —CN, =O, halo, or a $C_{1-4}$aliphatic chain, wherein up to two methylene units of the aliphatic chain are optionally replaced with —O—, —NR$^a$—, —C(O)—, or —S(O)$_z$—;

$J^T$ is independently halo, —CN, →O; =O, —OH, a $C_{1-6}$aliphatic chain, wherein up to two methylene units of the aliphatic chain are optionally replaced with —O—, —NR$^a$—, —C(O)—, or —S(O)$_z$—; or a 3-6 membered non-aromatic ring having 0-2 heteroatoms selected from the group consisting of oxygen, nitrogen, and sulfur; each occurrence of $J^T$ is optionally substituted with 0-3 occurrences of $J^M$; or two occurrences of $J^T$ on the same atom, together with the atom to which they are joined, form a 3-6 membered ring having 0-2 heteroatoms selected from the group consisting of oxygen, nitrogen, and sulfur; or two occurrences of $J^T$, together with $Q^3$, form a 6-10 membered saturated or partially unsaturated bridged ring system;

$J^M$ is independently halo or $C_{1-6}$aliphatic;

z is 0, 1 or 2; and $R^a$ is independently H or $C_{1-4}$aliphatic.

In some embodiments, $R^{10}$ and $R^3$ are fluoro.

In other embodiments, $R^4$ is $Q^1$.

In still other embodiments, $Q^1$ is independently piperidinyl and imidazolyl.

In yet another embodiment, the compound that inhibits ATR is a compound represented by Formula A-3:

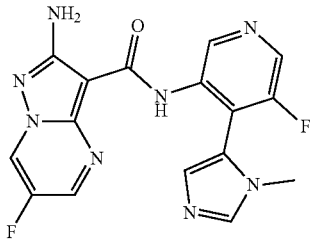

A-3 or a pharmaceutically acceptable salt thereof.

In another embodiment, the compound that inhibits ATR is represented by Formula A-II-a:

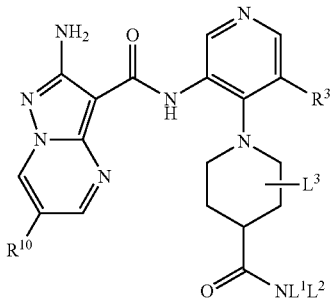

A-II-a or a pharmaceutically acceptable salt or prodrug thereof, wherein:

$R^{10}$ is fluoro, chloro, or —C(J$^{10}$)$_2$CN;

$J^{10}$ is independently H or $C_{1-2}$alkyl; or two occurrences of $J^1$, together with the carbon atom to which they are attached, form an optionally substituted 3-4 membered carbocyclic ring;

$R^3$ is H; chloro; fluoro; $C_{1-4}$alkyl optionally substituted with 1-3 occurrences of halo; $C_{3-4}$cycloalkyl; —CN; or a $C_{1-3}$aliphatic chain, wherein up to two methylene units of the aliphatic chain are optionally replaced with —O—, —NR$^a$—, —C(O)—, or —S(O)$_z$;

$L^1$ is H; a 3-7 membered aromatic or non-aromatic ring having 0-2 heteroatoms selected from the group consisting of oxygen, nitrogen, and sulfur; or a $C_{1-6}$aliphatic chain, wherein up to two methylene units of the aliphatic chain are optionally replaced with —O—, —NR$^a$—, —C(O)—, or —S(O)$_z$; each $L^1$ is optionally substituted with $C_{1-4}$aliphatic; —CN; halo; —OH; or a 3-6 membered non-aromatic ring having 0-2 heteroatoms selected from the group consisting of oxygen, nitrogen, and sulfur;

$L^2$ is H; a 3-7 membered aromatic or non-aromatic ring having 0-2 heteroatoms selected from the group consisting of oxygen, nitrogen, and sulfur; or a $C_{1-6}$aliphatic chain, wherein up to two methylene units of the aliphatic chain are optionally replaced with —O—, —NR$^a$—, —C(O)—, or —S(O)$_z$; each $L^2$ is optionally substituted with $C_{1-4}$aliphatic; —CN; halo; —OH; or a 3-6 membered non-aromatic ring having 0-2 heteroatoms selected from the group consisting of oxygen, nitrogen, and sulfur; or $L^1$ and $L^2$, together with the nitrogen to which they are attached, form a Ring D; Ring D is optionally substituted with 0-5 occurrences of $J^G$;

$L^3$ is H, $C_{1-3}$aliphatic, or CN;

Ring D is a 3-7 membered heterocyclyl ring having 1-2 heteroatoms selected from the group consisting of oxygen, nitrogen, and sulfur; or an 7-12 membered fully saturated or partially unsaturated bicyclic ring having 1-5 heteroatoms selected from the group consisting of oxygen, nitrogen, and sulfur;

$J^G$ is independently halo; —CN; —N(R$^o$)$_2$; →O; a 3-6 membered carbocycyl; a 3-6 membered heterocyclyl having 1-2 heteroatoms selected from the group consisting of oxygen, nitrogen, and sulfur; or a $C_{1-4}$alkyl chain, wherein up to two methylene units of the alkyl chain are optionally replaced with —O—, —NR$^a$—, —C(O)—, or —S(O)$_z$; each $J^G$ is optionally substituted with 0-2 occurrences of $J^K$.

two occurrences of $J^G$ on the same atom, together with the atom to which they are joined, form a 3-6 membered ring having 0-2 heteroatoms selected from the group consisting of oxygen, nitrogen, and sulfur; or two occurrences of $J^G$, together with Ring D, form a 6-10 membered saturated or partially unsaturated bridged ring system;

$J^K$ is a 3-7 membered aromatic or non-aromatic ring having 0-2 heteroatoms selected from the group consisting of oxygen, nitrogen, and sulfur;

z is 0, 1, or 2; and $R^a$ and $R^o$ are independently H or $C_{1-4}$alkyl.

In another embodiment, $R^1$ and $R^3$ are fluoro.

In still other embodiments, the compound that inhibits ATR is a compound represented by Formula A-4:

A-4

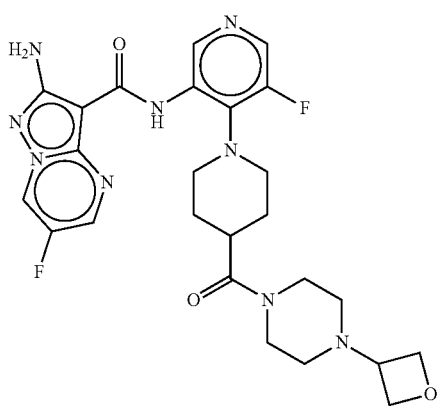

or a pharmaceutically acceptable salt thereof.

In yet another embodiment, the compound is an ATR inhibitor selected from a compound described in WO 2013/049726, WO 2013/152298, WO 2013/049859, US-2013-0089625, US-2013-0115312, US-2014-0107093, US-2013-0096139, WO 2011/143426, US-2013-0095193, WO 2014/055756, WO 2011/143419, WO 2011/143422, WO 2011/143425, US-2013-0115311, US-2013-0115312, US-2013-0115313, US-2013-0115314, WO 2011/163527, WO 2012/178123, WO 2012/178124, WO 2012/178125, US-2014-0113005, WO2013/049726, WO 2013/071085, WO 2010/071837, WO 2014/089379, WO 2014/143242, WO 2014/143241, WO 2015/084384, and/or WO 2014/143240. In certain embodiments, the ATR inhibitor is a compound of Formula (A-I) or (A-II). In certain embodiments, the ATR inhibitor is a compound of Formula A-1, A-2, A-3, or A-4.

In yet another embodiment, the compound is an ATR inhibitor selected from a compound described in WO 2015/187451, WO 2015/085132, WO 2014/062604; WO 2014/143240; WO 2013/071094; WO 2013/071093; WO 2013/071090; WO 2013/071088; WO 2013/049859; WO 2013/049719; WO 2013/049720; WO 2013/049722; WO 2012/138,938; WO 2011/163527; WO 2011/143,423; WO 2011/143,426; WO 2011/143,399; and/or WO 2010/054398.

In certain embodiments, the compound that inhibits ATR is selected from a compound described in WO 2013/014448. In certain embodiments, the compound that inhibits ATR is AZD-6738.

For purposes of this application, it will be understood that the terms embodiment, example, and aspect are used interchangeably.

For example, for the purposes of this application, it will be understood that when two occurrences of $J^{Q1}$, together with $Q^1$, form a bridged ring system, the two occurrences of $J^{Q1}$ are attached to separate atoms of $Q^1$. Additionally, when two occurrences of $J^R$, together with $Q^2$, form a bridged ring system, the two occurrences of $J^R$ are attached to separate atoms of $Q^2$. Moreover, when two occurrences of $J^T$, together with $Q^3$, form a bridged ring system, the two occurrence of $J^T$ are attached to separate atoms of $Q^3$. Finally, when two occurrences of $J^G$, together with Ring D, form a bridged ring system, the two occurrences of $J^G$ are attached to separate atoms of Ring D.

For purposes of this application, it will be understood that the terms ATR, ATR kinase, and ATR protein kinase, as well as an ATR inhibitor and a compound that inhibits ATR, are used interchangeably.

It will be understood by those skilled in the art that the arrow in →O represents a dative bond.

This application refers to various issued patent, published patent applications, journal articles, and other publications, all of which are incorporated herein by reference.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

Unless otherwise indicated, a substituent connected by a bond drawn from the center of a ring means that the substituent can be bonded to any position in the ring. In example i below, for instance, $J^1$ can be bonded to any position on the pyridyl ring. For bicyclic rings, a bond drawn through both rings indicates that the substituent can be bonded from any position of the bicyclic ring. In example ii below, for instance, $J^1$ can be bonded to the 5-membered ring (on the nitrogen atom, for instance), and to the 6-membered ring.

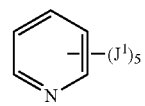

i

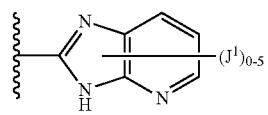

ii

The term "stable", as used herein, refers to compounds that are not substantially altered when patiented to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "dative bond", as used herein, is defined as the coordination bond formed upon interaction between molecular species, one of which serves as a donor and the other as an acceptor of the electron pair to be shared in the complex formed.

The term "aliphatic" or "aliphatic group", as used herein, means a straight-chain (i.e., unbranched), branched, or cyclic, substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl. Aliphatic groups may also be cyclic, or have a combination of linear or branched and cyclic groups. Examples of such types of aliphatic groups include, but are not limited to cyclopropyl, cyclobutyl, cyclopentyl, cyclohexyl, cyclohexenyl, —$CH_2$-cyclopropyl, $CH_2CH_2CH(CH_3)$-cyclohexyl.

The term "cycloaliphatic" (or "carbocycle" or "carbocyclyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —$CF_3$ and —$CF_2CF_3$.

The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

It shall be understood that the term "heteroaryl" includes certain types of heteroaryl rings that exist in equilibrium between two different forms. More specifically, for example, species such hydropyridine and pyridinone (and likewise hydroxypyrimidine and pyrimidinone) are meant to be encompassed within the definition of "heteroaryl."

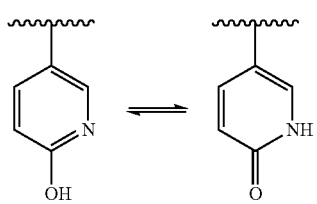 [SMILES: *c1ccc(O)nc1 ; *c1ccc(=O)[nH]c1]

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, a methylene unit of an alkyl or aliphatic chain is optionally replaced with another atom or group. Examples of such atoms or groups include, but are not limited to, nitrogen, oxygen, sulfur, —C(O)—, —C(=N—CN)—, —C(=NR)—, —C(=NOR)—, —SO—, and —SO$_2$—. These atoms or groups can be combined to form larger groups. Examples of such larger groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is, for example, H or C$_{1-6}$aliphatic. It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

Unless otherwise indicated, the optional replacements form a chemically stable compound. Optional replacements can occur both within the chain and/or at either end of the chain; i.e. both at the point of attachment and/or also at the terminal end. Two optional replacements can also be adjacent to each other within a chain so long as it results in a chemically stable compound. For example, a C$_3$ aliphatic can be optionally replaced by 2 nitrogen atoms to form —C—N=N. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to a hydrogen atom on the terminal end. For example, if a methylene unit of —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

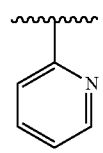

also represents

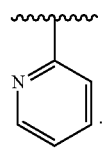

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The compounds disclosed herein can be prepared by any suitable methods known in the art, for example, WO 2015/187451, WO 2015/085132, WO 2014/062604; WO 2014/143240; WO 2013/071094; WO 2013/071093; WO 2013/071090; WO 2013/071088; WO 2013/049859; WO 2013/049719; WO 2013/049720; WO 2013/049722; WO 2012/138,938; WO 2011/163527; WO 2011/143,423; WO 2011/143,426; WO 2011/143,399; WO 2010/054398; WO 2013/049726, WO 2013/152298, WO 2013/049859, US-2013-0089625, US-2013-0115312, US-2014-0107093, US-2013-0096139, WO 2011/143426, US-2013-0095193, WO 2014/055756, WO 2011/143419, WO 2011/143422, WO 2011/143425, US-2013-0115311, US-2013-0115312, US-2013-0115313, US-2013-0115314, WO 2011/163527, WO 2012/178123, WO 2012/178124, WO 2012/178125, US-2014-0113005, WO2013/049726, WO 2013/071085, WO 2010/071837, WO 2014/089379, WO 2014/143242, WO 2014/143241, WO 2015/084384, and/or WO 2014/143240.

DNA Damaging Agents

In some aspects of the present disclosure, the DNA damaging agent is radiation therapy. In certain embodiments, the DNA-damaging agent comprises chemotherapy. In certain embodiments, the ATR inhibitor is a compound of Formula A-1, a compound of Formula A-2, a compound of Formula A-3, a compound of Formula A-4, or AZD-6738, and the DNA-damaging agent is radiation or chemotherapy.

In certain embodiments, the DNA damaging agent comprises radiation therapy. Examples of radiation therapy include, but are not limited to, ionizing radiation, gamma-radiation, neutron beam radiotherapy, electron beam radiotherapy, proton therapy, brachytherapy, systemic radioactive isotopes and radiosensitizers. Radiosensitizers work in various different ways, including, but not limited to, making cancer cells more sensitive to radiation, working in synergy with radiation to provide an improved synergistic effect, acting additively with radiation, or protecting surrounding healthy cells from damage caused by radiation.

In certain embodiments, the DNA-damaging agent comprises chemotherapy. Examples of chemotherapy include, but are not limited to, platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; topo I inhibitors, such as Camptothecin, Topotecan, irinotecan/SN38, rubitecan, Belotecan, and other derivatives; topo II inhibitors, such as Etoposide (VP-16), Daunorubicin, Doxorubicin, Mitoxantrone, Aclarubicin, Epirubicin, Idarubicin, Amrubicin, Amsacrine, Pirarubicin, Valrubicin, Zorubicin, Teniposide and other derivatives; antimetabolites, such as Folic family (Methotrexate, Pemetrexed, Raltitrexed, Aminopterin, and relatives); Purine antagonists (Thioguanine, Fludarabine, Cladribine, 6-Mercaptopurine, Pentostatin, clofarabine and relatives) and Pyrimidine antagonists (Cytarabine, Floxuridine, Azacitidine, Tegafur, Carmofur, Capacitabine, Gemcitabine, hydroxyurea, 5-Fluorouracil(5FU), and relatives); alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives); nitrosoureas (e.g., Carmustine, Lomustine, Semustine, Fotemustine, Nimustine, Ranimustine, Streptozocin, and relatives); Triazenes (e.g., Dacarbazine, Altretamine, Temozolomide, and relatives); Alkyl sulphonates (e.g., Busulfan, Mannosulfan, Treosulfan, and relatives); Procarbazine; Mitobronitol, and Aziridines (e.g., Carboquone, Triaziquone, ThioTEPA, triethylenemalamine, and relatives); antibiotics, such as Hydroxyurea, Anthracyclines (e.g., doxorubicin, daunorubicin, epirubicin and other derivatives); Anthracenediones (e.g, Mitoxantrone and relatives); antibiotics from the *Streptomyces* family (e.g., Bleomycin, Mitomycin C, Actinomycin, Plicamycin); and ultraviolet light.

In certain embodiments, the ATR inhibitor is a compound of Formula A-1, compound of Formula A-2, compound of Formula A-3, compound of Formula A-4, or AZD-6738, and the DNA damaging agent comprises chemotherapy. In certain embodiments, the ATR inhibitor is a compound of Formula A-1, a compound of Formula A-2, a compound of Formula A-3, a compound of Formula A-4, or AZD-6738 and the DNA damaging agent comprises a platinating agent (e.g., cisplatin, carboplatin). In certain embodiments, the ATR inhibitor is a compound of Formula A-1, a compound of Formula A-2, a compound of Formula A-3, a compound of Formula A-4, or AZD-6738 and the DNA damaging agent comprises a antimetabolite (e.g., gemcitabine). In certain embodiments, the ATR inhibitor is a compound of Formula A-2 and the DNA damaging agent is cisplatin or gemcitabine.

In certain embodiments, the ATR inhibitor is a compound of Formula A-1 and the DNA damaging agent is cisplatin or gemcitabine. In certain embodiments, the ATR inhibitor is a compound of Formula A-2 and the DNA damaging agent is cisplatin or gemcitabine. In certain embodiments, the ATR inhibitor is a compound of Formula A-3 and the DNA damaging agent is cisplatin or gemcitabine. In certain embodiments, the ATR inhibitor is a compound of Formula A-4 and the DNA damaging agent is cisplatin or gemcitabine. In certain embodiments, the ATR inhibitor is AZD-6738 and the DNA damaging agent is cisplatin or gemcitabine.

In certain embodiments, the ATR inhibitor is a compound of Formula A-1 and the DNA damaging agent is carboplatin or gemcitabine. In certain embodiments, the ATR inhibitor is a compound of Formula A-2 and the DNA damaging agent is carboplatin or gemcitabine. In certain embodiments, the ATR inhibitor is a compound of Formula A-3 and the DNA damaging agent is carboplatin or gemcitabine. In certain embodiments, the ATR inhibitor is a compound of Formula A-4 and the DNA damaging agent is carboplatin or gemcitabine. In certain embodiments, the ATR inhibitor is AZD-6738 and the DNA damaging agent is carboplatin or gemcitabine.

Dosages of DNA Damaging Agent and ATR Inhibitor

In general, any effective dose of an ATR inhibitor and DNA damaging agent may be administered. In some embodiments, an ATR inhibitor (e.g., a compound of Formula A-2) when used in a combination therapy with a DNA-damaging agent, as described herein, may be administered at a dosage of between about 50 mg/m$^2$ and about 300 mg/m$^2$, between about 50 mg/m$^2$ and about 240 mg/m$^2$, between about 60 mg/m$^2$ and about 240 mg/m$^2$, between about 60 mg/m$^2$ and about 180 mg/m$^2$, between about 60 mg/m$^2$ and about 120 mg/m$^2$, between about 80 mg/m$^2$ and about 120 mg/m$^2$, between about 90 mg/m$^2$ and about 120 mg/m$^2$, or between about 80 mg/m$^2$ and about 100 mg/m$^2$. In certain embodiments, an ATR inhibitor may be administered at a dosage between about 50 mg/m$^2$ and about 300 mg/m$^2$ (e.g., about 240 mg/m$^2$). In some instances, an ATR inhibitor may be administered at a dosage between about 60 mg/m$^2$ and about 180 mg/m$^2$ (e.g., 120 mg/m$^2$). In certain cases, an ATR inhibitor may be administered at a dosage between about 80 mg/m$^2$ and about 100 mg/m$^2$ (e.g., about 90 mg/m$^2$). In some embodiments, ATR inhibitor (e.g., a compound of Formula A-2) may be administered at a dosage of about 90 mg/m² or about 120 mg/m².

In some embodiments, a platinating agent (e.g., carboplatin) when used in a combination therapy with an ATR inhibitor (e.g., a compound of Formula A-2), as described herein, may be administered at a target AUC of between about 3 mg/mL·min and about 6 mg/mL·min, between about 3.5 mg/mL·min and about 6 mg/mL·min, between about 4 mg/mL·min and about 6 mg/mL·min, between about 4 mg/mL·min and about 5.5 mg/mL·min, or between about 4 mg/mL·min and about 5 mg/mL·min. In some embodiments, a platinating agent (e.g., carboplatin) may be administered at a target AUC of between about 3 mg/mL·min and about 6 mg/mL·min. In certain embodiments, a platinating agent (e.g., carboplatin) may be administered with at a target AUC of between about 4 mg/mL·min and about 5 mg/mL·min. As used herein, the term "target AUC" refers the target area under the plasma concentration versus time curve. The term "AUC" refers the area under the plasma concentration versus time curve. The dosage of certain DNA damaging agents, such as carboplatin, may be determined from the drug label information. For example, the dosage in mg of carboplatin may be determined from the target AUC based on mathematical formula, which is based on a patient's pre-existing renal function or renal function and desired platelet nadir. The Calvert formula, shown below, is used to calculate dosage in milligrams, based upon a patient's glomerular filtration rate (GFR in mL/min) and carboplatin target area under the concentration versus time curve (AUC in mg/mL·min). GFR may be measured using $^{51}$Cr-EDTA clearance or may be estimated using methods known to ordinary skill in the art.

Total Dose (mg)=(target AUC)×(GFR+25)

It should be understood that all combinations of the above-referenced ranges for dosage of ATR inhibitor and dosage of a DNA damaging agent for use in a combination therapy, as described herein, may be possible. For instance, in some embodiments, a platinating agent (e.g., carboplatin) may be administered with at a target AUC of between about 3 mg/mL·min and about 6 mg/mL·min (e.g., between about 4 mg/mL·min and about 6 mg/mL·min, between about 4 mg/mL·min and about 5 mg/mL·min) and an ATR inhibitor (e.g., a compound of Formula A-2) may be administered with at a dosage between about 50 mg/m² and about 300 mg/m² (e.g., between about 60 mg/m² and about 180 mg/m², between about 80 mg/m² and about 100 mg/m²).

In certain embodiments, a platinating agent (e.g., carboplatin) may be administered with at a target AUC of between about 3 mg/mL·min and about 6 mg/mL·min (e.g., between about 4 mg/mL·min and about 6 mg/mL·min) and an ATR inhibitor (e.g., a compound of Formula A-2) may be administered with at a dosage between about 60 mg/m² and about 180 mg/m² (e.g., about 90 mg/m², about 120 mg/m²). In one example, a method of treating a proliferative disorder (e.g., ovarian, lung, colorectal) may comprise administering a platinating agent (e.g., carboplatin) at a target AUC of between about 4 mg/mL·min and about 5 mg/mL·min on day 1, a dose of between about 90 mg/m² and about 120 mg/m² of a first dose of ATR inhibitor (e.g., a compound of Formula A-2) on day 2 between about 20 hours and about 28 hours (e.g., about 24 hours or 24 hours±2 hours) after administration of the platinating agent, and a second dose of the ATR inhibitor between about 6 days and about 8 days (e.g., on day 9) after the first dose. Such a treatment method may lead to at least a RECIST partial response and/or may decrease the sum of the longest diameter of target lesions, decrease the sum of the longest diameter of non-target lesions, and/or decrease tumor burden by between about 20% and about 60%, or between about 40% and about 60%. In some such embodiments, the proliferative disorder (e.g., ovarian cancer, lung cancer, colorectal cancer, breast cancer) may have a defect in ATM signaling (e.g., mutation in p53, partial loss of ATM signaling, complete loss of ATM signaling).

In other embodiments in which the ATR inhibitor (e.g., a compound of Formula A-2) is administered as a monotherapy or a combination therapy with a DNA-damaging agent, as described herein, said ATR inhibitor (e.g., a compound of Formula A-2) may be administered at a dosage of between about 50 mg/m² and about 500 mg/m², between about 100 mg/m² and about 500 mg/m², between about 120 mg/m² and about 500 mg/m², between about 240 mg/m² and about 480 mg/m², between about 50 mg/m² and about 480 mg/m², between about 50 mg/m² and about 300 mg/m², between about 50 mg/m² and about 240 mg/m², or between about 50 mg/m² and about 120 mg/m². In some embodiments, said ATR inhibitor (e.g., a compound of Formula A-2) may be administered at a dosage of about 60 mg/m², about 120 mg/m², about 240 mg/m², or 480 mg/m². In some embodiments, said ATR inhibitor (e.g., a compound of Formula A-2) may be administered at a dosage of about 240 mg/m² or about 480 mg/m² as a monotherapy. In some embodiments, said ATR inhibitor is Compound A-2. In some embodiments, Compound A-2 is administered at a dosage of about 240 mg/m² as a monotherapy. In some embodiments, Compound A-2 is administered at a dosage of about 240 mg/m² as a monotherapy once weekly or twice weekly.

In some embodiments, cisplatin is used in a combination therapy with a compound of Formula A-2, wherein the dosage of cisplatin is at between about 30 and about 90 mg/m², between about 40 and about 75 mg/m², or between about 60 and about 90 mg/m², and wherein the dosage of the compound of Formula A-2 is between about 60 mg/m² and about 240 mg/m², between about 120 mg/m² and 160 mg/m², or between about 90 mg/m² and about 210 mg/m². In some specific embodiments, the dosage of cisplatin is at 40 mg/m², 60 mg/m², or 75 mg/m². In some specific embodiments, the dosage of a compound of Formula A-2 is about 90 mg/m², 140 mg/m², or 210 mg/m². In some specific embodiments, the dosage of cisplatin is at between about 30 and about 90 mg/m², and the dosage of the compound of Formula A-2 is between about 60 mg/m² and about 240 mg/m². In some specific embodiments, the dosage of cisplatin is at between about 40 and about 75 mg/m², and the dosage of a compound of Formula A-2 is between about 90 mg/m² and 210 mg/m². In some specific embodiments, the dosage of cisplatin is at between about 60 and about 90 mg/m², and the dosage of the compound of Formula A-2 is between about 120 mg/m² and 160 mg/m². In some specific embodiments, the dosage of cisplatin is at about 75 mg/m², and the dosage of the compound of Formula A-2 is about 140 mg/m².

In some embodiments, gemcitabine is used in a combination therapy with a compound of Formula A-2, wherein the dosage of gemcitabine is between about 300 and about 1200 mg/m², between about 875 mg/m² and 1125 mg/m², or between about 500 mg/m² and about 1000 mg/m², and wherein the dosage of the compound of Formula A-2 is between about 10 mg/m² and about 240 mg/m², between about 18 mg/m² and 210 mg/m², or between about 180 mg/m² and 240 mg/m². In some specific embodiments, gemcitabine may be administered at 500 mg/m², 750 mg/m², 875 mg/m², or 1000 mg/m². In some specific embodiments, the dosage of the compound of Formula A-2 is about 18 mg/m$^2$, 36 mg/m$^2$, 60 mg/m$^2$, 72 mg/m$^2$, 90 mg/m$^2$, 140 mg/m$^2$, or 210 mg/m$^2$. In some specific embodiments, the dosage of gemcitabine is between about 300 and about 1200 mg/m$^2$, and the dosage of a compound of Formula A-2 is between about 10 mg/m$^2$ and about 240 mg/m$^2$. In some specific embodiments, the dosage of gemcitabine is between about 500 and about 1000 mg/m$^2$, and the dosage of the compound of Formula A-2 is between about 18 mg/m$^2$ and about 210 mg/m$^2$. In some specific embodiments, the dosage of gemcitabine is between about 875 mg/m$^2$ and about 1125 mg/m$^2$, and the dosage of the compound of Formula A-2 is between about 180 mg/m$^2$ and about 240 mg/m$^2$. In some specific embodiments, the dosage of gemcitabine is about 1000 mg/m$^2$, and the dosage of the compound of Formula A-2 is about 210 mg/m$^2$.

In some embodiments, gemcitabine and cisplatin are used in a combination therapy with a compound of Formula A-2, wherein the dosage of gemcitabine is between about 300 and about 1200 mg/m$^2$, between about 500 mg/m$^2$ and 1,000 mg/m$^2$, or between about 700 mg/m$^2$ and about 1,000 mg/m$^2$, and wherein the dosage of the compound of Formula A-2 is between about 10 mg/m$^2$ and about 250 mg/m$^2$, between about 30 mg/m$^2$ and 250 mg/m$^2$, or between about 50 mg/m$^2$ and 200 mg/m$^2$, or between about 80 mg/m$^2$ and 200 mg/m$^2$, and wherein the dosage of cisplatin is between about 30 mg/m$^2$ and 90 mg/m$^2$, or between about 50 mg/m$^2$ and 90 mg/m$^2$. In some specific embodiments, gemcitabine may be administered at 500 mg/m$^2$, 750 mg/m$^2$, 875 mg/m$^2$, or 1000 mg/m$^2$. In some specific embodiments, the dosage of the compound of Formula A-2 is about 18 mg/m$^2$, 36 mg/m$^2$, 60 mg/m$^2$, 72 mg/m$^2$, 90 mg/m$^2$, 140 mg/m$^2$, or 210 mg/m$^2$. In some specific embodiments, the dosage of cisplatin is about 40 mg/m$^2$, 60 mg/m$^2$, 75 mg/m$^2$, 90 mg/m$^2$, 140 mg/m$^2$, or 210 mg/m$^2$. In some specific embodiments, the dosage of gemcitabine is between about 500 and about 1000 mg/m$^2$; the dosage of the compound of Formula A-2 is between about 60 mg/m$^2$ and about 210 mg/m$^2$; and the dosage of cisplatin is between about 50 mg/m$^2$ and about 90 mg/m$^2$. In some specific embodiments, the dosage of gemcitabine is about 875 mg/m$^2$; the dosage of the compound of Formula A-2 is about 90 mg/m$^2$; and the dosage of cisplatin is about 60 mg/m$^2$.

Biomarkers

In some embodiments, one or more biomarkers may be used to monitor or determine the efficacy of the treatment. In certain embodiments, the percentage of phosphorylated Chk1 (i.e., pChk1) in paired samples may be used as a biomarker; pChk1 is believed to correlate with the level of ATR activity. For instance, in some embodiments, the amount of pChk1 in the nuclei of cancer cells/mm$^2$ of a tumor biopsy may be used to determine the efficacy of monotherapy with an ATR inhibitor or combination therapy including an ATR inhibitor in a subject. In some such embodiments, a first tumor biopsy may be taken between about one to about three hours (e.g., two hours) before administration of the ATR inhibitor and a second tumor biopsy may be taken between about one to about three hours (e.g., two hours) after administration of the ATR inhibitor. The amount of pChk1 in the nuclei of cancer cells/mm$^2$ tumor in the first biopsy is set to be 100%, such that the amount of pChk1 in the nuclei of cancer cells/mm$^2$ tumor in the second biopsy is normalized by the amount in the first biopsy.

In some embodiments, a method of treating a proliferative disorder comprising administering a platinating agent (e.g., carboplatin) at a target AUC of between about 4 mg/mL·min and about 5 mg/mL·min on day 1, a dose of between about 90 mg/m$^2$ and about 120 mg/m$^2$ of a first dose of a ATR inhibitor (e.g., a compound of Formula A-2) between about 20 hours and about 28 hours (e.g., about 24 hours or 24 hours±2 hours) after administration of the platinating agent on day 1, and a second dose of the ATR inhibitor between about 6 days and about 8 days (e.g., on day 9) after the first dose, may substantially reduce the percentage of pChk1 in the nuclei of cancer cells/mm$^2$. In some such embodiments, the percentage of pChk1 in the nuclei of cancer cells/mm$^2$ may be less than about 40%, less than about 30%, less than about 20%, or less than about 10% between about one to about three hours (e.g., two hours) after administration of the ATR inhibitor.

In some embodiments, certain cancer specific biomarkers may be used to monitor or determine the efficacy of the treatment. For instance, CA125 ovarian cancer tumor burden marker may be used to assess treatment of ovarian cancer with monotherapy or with combination therapy including an ATR inhibitor and a DNA damaging agent.

In some embodiments, certain treatment related adverse events in a subject may be used as biomarkers to monitor or determine the efficacy of the treatment. In certain embodiments, an adverse event may be indicative of the mechanism of action of the ATR inhibitor in a combination therapy. For example, the presence of neutropenia and thrombocytopenia may be used as biomarkers.

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases, which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N, N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like are examples of suitable base addition salts.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester, or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed).

Therapeutic Uses

The present disclosure provides a method of treating diseases, disorders, and conditions characterized by excessive or abnormal cell proliferation, including proliferative or hyperproliferative diseases, in a subject. A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, hematological malignancies. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM). Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor, neuroendocrine prostate); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; adenoid cystic carcinoma; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis *nodosa*), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis *nodosa*, systemic lupus erythematosis, rheumatoid arthritis, psoriatic arthritis, systemic lupus erythematosus, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

In some embodiments, the term "cancer" includes, but is not limited to the following types of cancers: oral, lung, gastrointestinal, genitourinary tract, liver, bone, nervous system, gynecological, skin, thyroid gland, or adrenal gland. More specifically, "cancer" includes, but is not limited to the following cancers: oral cancers, such as buccal cavity cancer, lip cancer tongue cancer, mouth cancer, and pharynx cancer; cardiac cancers: sarcoma (e.g., angiosarcoma, fibrosarcoma, rhabdomyosarcoma, liposarcoma), myxoma, rhabdomyoma, fibroma, lipoma, and teratoma; lung cancers, such as bronchogenic carcinoma (e.g., squamous cell or epidermoid, undifferentiated small cell, undifferentiated large cell, adenocarcinoma), alveolar (e.g., bronchiolar) carcinoma, bronchial adenoma, sarcoma, lymphoma, chondromatous, hamartoma, and mesothelioma; gastrointestinal cancers, such as esophageal cancer (e.g., squamous cell carcinoma, larynx, adenocarcinoma, leiomyosarcoma, lymphoma), stomach cancer (e.g., carcinoma, lymphoma, leiomyosarcoma), pancreatic cancer (e.g., ductal adenocarcinoma, insulinoma, glucagonoma, gastrinoma, carcinoid tumors, vipoma), small bowel or small intestinal cancer (e.g., adenocarcinoma, lymphoma, carcinoid tumors, Karposi's sarcoma, leiomyoma, hemangioma, lipoma, neurofibroma, fibroma), large bowel or large intestinal cancer (e.g., adenocarcinoma, tubular adenoma, villous adenoma, hamartoma, leiomyoma), colon cancer, colon-rectum cancer, colorectal cancer, and rectum cancer, genitourinary tract cancers, such as kidney cancer (e.g., adenocarcinoma, Wilm's tumor [nephroblastoma], lymphoma, leukemia), bladder cancer, urethral cancer (e.g., squamous cell carcinoma, transitional cell carcinoma, adenocarcinoma), prostate cancer (e.g., adenocarcinoma, sarcoma), and testicular cancer (e.g., seminoma, teratoma, embryonal carcinoma, teratocarcinoma, choriocarcinoma, sarcoma, interstitial cell carcinoma, fibroma, fibroadenoma, adenomatoid tumors, lipoma); liver cancers, such as hepatoma (e.g., hepatocellular carcinoma), cholangiocarcinoma, hepatoblastoma, angiosarcoma, hepatocellular adenoma, hemangioma, and biliary passages; bone cancers, such as osteogenic sarcoma (e.g., osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (e.g., osteocartilaginous exostoses), benign chondroma, chondroblastoma, chondromyxofibroma, and osteoid osteoma and giant cell tumors; Nervous system cancers, such as: skull cancer (e.g., osteoma, hemangioma, granuloma, xanthoma, osteitis deformans), meningeal cancer (e.g., meningioma, meningiosarcoma, gliomatosis), brain cancer (e.g., astrocytoma, medulloblastoma, glioma, ependymoma, germinoma [pinealoma], glioblastoma multiform, oligodendroglioma, schwannoma, retinoblastoma, congenital tumors), and spinal cord cancer (e.g., neurofibroma, meningioma, glioma, sarcoma); gynecological cancers: uterine cancer (e.g., endometrial carcinoma), cervical cancer (e.g., cervical carcinoma, pre-tumor cervical dysplasia), ovarian cancer (e.g., ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulvar cancer (e.g., squamous cell carcinoma, intraepithelial carcinoma, adenocarcinoma, fibrosarcoma, melanoma), vaginal cancer (e.g., clear cell carcinoma, squamous cell carcinoma, botryoid sarcoma (embryonal rhabdomyosarcoma), fallopian tube cancer (e.g., carcinoma), an breast cancer; hematologic cancers, such as blood cancer (e.g., myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell, and lymphoid disorders; skin cancers, such as malignant melanoma, basal cell carcinoma, squamous cell carcinoma, Karposi's sarcoma, keratoacanthoma, moles dysplastic nevi, lipoma, angioma, dermatofibroma, keloids, psoriasis; thyroid gland cancers, such as papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma, and Adenoid cystic carcinoma; and adrenal gland cancers, such as neuroblastoma.

In other embodiments, the cancer is lung cancer (e.g., non-small cell lung cancer, small cell lung cancer, mesothelioma), head and neck cancer (e.g., nasopharyngeal cancer), pancreatic cancer, breast cancer (e.g., triple negative breast cancer), gastric cancer, brain cancer, endometrial carcinoma, pancreatic cancer, biliary tract cancer, bladder cancer, colorectal cancer, glioblastoma, esophageal cancer, hepatocellular carcinoma, neuroendocrine cancer, or ovarian cancer. In certain embodiments, the cancer is lung cancer (e.g., mesothelioma), breast cancer (e.g., triple negative breast cancer), neuroendocrine cancer (e.g., neuroendocrine prostate cancer), or ovarian cancer (e.g., CA125 positive ovarian cancer). In certain embodiments, the cancer is nasopharyngeal cancer. In certain embodiments, the cancer is fallopian tube cancer, peritoneal cancer, urothelial carcinoma, esophageal cancer, or head and neck squamous cell carcinoma.

The method comprises administering to a subject in need thereof a DNA damaging agent, and between about 12-48 hours later administering to the subject a compound that inhibits ATR protein kinase. In some embodiments, the compound that inhibits ATR is administered about 18-42 hours after administration of the DNA damaging agent. In some embodiments, the compound that inhibits ATR is administered about 20-40 hours after administration of the DNA damaging agent. In some embodiments, the compound that inhibits ATR is administered about 12-36 hours after administration of the DNA damaging agent. In some embodiments, the compound that inhibits ATR is administered about 18-36 hours after administration of the DNA damaging agent. In some embodiments, the compound that inhibits ATR is administered about 20-28 hours after administration of the DNA damaging agent. In some embodiments, the compound that inhibits ATR is administered about 24 hours after administration of the DNA damaging agent. In some embodiments, the compound that inhibits ATR is administered 24 hours±2 hours after administration of the DNA damaging agent. In some embodiments, said DNA-damaging agent is chemotherapy or radiation treatment.

A "subject" to which administration is contemplated includes, but is not limited to, humans; commercially relevant mammals such as cattle, pigs, horses, sheep, goats, cats, and/or dogs) and birds (e.g., commercially relevant birds such as chickens, ducks, geese, and/or turkeys). A subject in need of treatment is a subject identified as having a proliferative disorder i.e., the subject has been diagnosed by a physician (e.g., using methods well known in the art) as having a proliferative disorder (e.g., a cancer). In some embodiments, the subject in need of treatment is a subject suspected of having or developing a proliferative disorder, such as a subject presenting one or more symptoms indicative of a proliferative disorder. The term "subject in need of treatment" further includes people who once had a proliferative disorder but whose symptoms have ameliorated. For cancer, the one or more symptoms or clinical features depend on the type and location of the tumor. For example, lung tumors may cause coughing, shortness of breath, or chest pain. Tumors of the colon can cause weight loss, diarrhea, constipation, iron deficiency anemia, and blood in the stool. The following symptoms occur with most tumors: chills, fatigue, fever, loss of appetite, malaise, night sweats, and weight loss.

The terms "administer," "administering," or "administration," as used herein refers to implanting, absorbing, ingesting, injecting, or inhaling the one or more therapeutic agents.

As used herein, the terms "treatment," "treat," and "treating" refer to reversing, alleviating, delaying the onset of, or inhibiting the progress of proliferative disorder. In some embodiments, treatment may be administered after one or more signs or symptoms have developed or have been observed. In other embodiments, treatment may be administered in the absence of signs or symptoms of the proliferative disorder. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "tumor burden" has its ordinary meaning in the art and may refer to the number of cancer cells, the size of a tumor, or the amount of cancer in the body.

As used herein, the terms "about" has its ordinary meaning in the art. In some embodiments with respect to time, about may be within 50 minutes, within 40 minutes, within 30 minutes, within 20 minutes, within 10 minutes, within 5 minutes, or within 1 minute of the specified time. In some embodiments with respect to dosage, about may be within 20%, within 15%, within 10%, within 5%, or within 1% of the specified dosage.

An "effective amount" refers to an amount sufficient to elicit the desired biological response, i.e., treating the proliferative disorder. As will be appreciated by those of ordinary skill in this art, the effective amount of the compounds described herein may vary depending on such factors as the desired biological endpoint, the pharmacokinetics of the compound, the condition being treated, the mode of administration, and the age and health of the subject. An effective amount includes, but is not limited to, that amount necessary to slow, reduce, inhibit, ameliorate or reverse one or more symptoms associated with neoplasia. For example, in the treatment of cancer, such terms may refer to a reduction in the size of the tumor.

An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

The compounds provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds provided herein may be administered at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Biological Samples

As inhibitors of the ATR pathway, the compounds and compositions of this invention are also useful in biological samples. One aspect of the invention relates to inducing DNA damage and inhibiting ATR in a biological sample, which method comprises contacting said biological sample with a DNA damaging agent followed by contacting the sample about 12-48 hours later with a compound that inhibits ATR kinase activity. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inducing DNA damage followed by inhibition of ATR activity in a biological sample is useful for a variety of purposes that are known to one of skill in the art. Examples of such purposes include, but are not limited to, blood transfusion, organ-transplantation, and biological specimen storage.

EXAMPLES

Example 1. Optimization of Dose Schedule In Vitro

The effect of altering a compound of Formula A-2 (Compound A-2) dosing schedule in combination with DNA damaging agents was assessed with gemcitabine in a pancreatic cancer cell line (PSN1) as shown in FIG. 1. Cells were treated with gemcitabine for 24 hours in combination with Compound A-2; Compound A-2 was added for 2 hour periods at various times both during and after gemcitabine treatment. Cell viability was measured by MTS assay (96 hours) and the data subjected to a statistical Bliss analysis. Compound A-2 synergized with gemcitabine when administered at the start of gemcitabine treatment. This synergistic effect markedly increased as Compound A-2 was administered progressively later through the 24 hour gemcitabine dosing period. Synergy was maximal when Compound A-2 was administered 24 hours after starting gemcitabine treatment as shown in FIG. 1; later administration of Compound A-2 was less effective. No synergy was seen when Compound A-2 was administered 48 hours or later, after gemcitabine treatment was started. The strong schedule dependence is attributed to an accumulation of cells in S phase, and concomitant increase in ATR activity (measured by P-Chk1) that occurs in response to gemcitabine treatment alone. Thus, maximal impact of Compound A-2 is expected at a time when most cells are in S phase as a result of gemcitabine treatment. Extended intervals (>48 hours) between gemcitabine therapy and Compound A-2 exposure allows DNA damage to be repaired, permitting cells to exit S phase and dramatically reducing the impact of ATR inhibition.

These data indicate that short exposures to Compound A-2 are sufficient to sensitize certain cancer cells to DNA damaging agents. Furthermore, the data suggest that administering Compound A-2 after treatment with a DNA damaging agent, to coincide with maximal S phase accumulation is optimal.

Example 2: Dose Schedule Optimization of a Compound of Formula A-2 in Combination with Gemcitabine or Cisplatin In vitro pharmacology studies have demonstrated that combinations of a compound of Formula A-2 (Compound A-2) and DNA damaging drugs are most effective when cells are treated with Compound A-2 after the DNA damaging drug, and when Compound A-2 addition is timed to coincide with peak accumulation of cells in S phase. The optimal in vivo dose schedule for Compound A-2 was assessed in combination with gemcitabine and cisplatin in 2 separate xenograft models.

Figure 2:
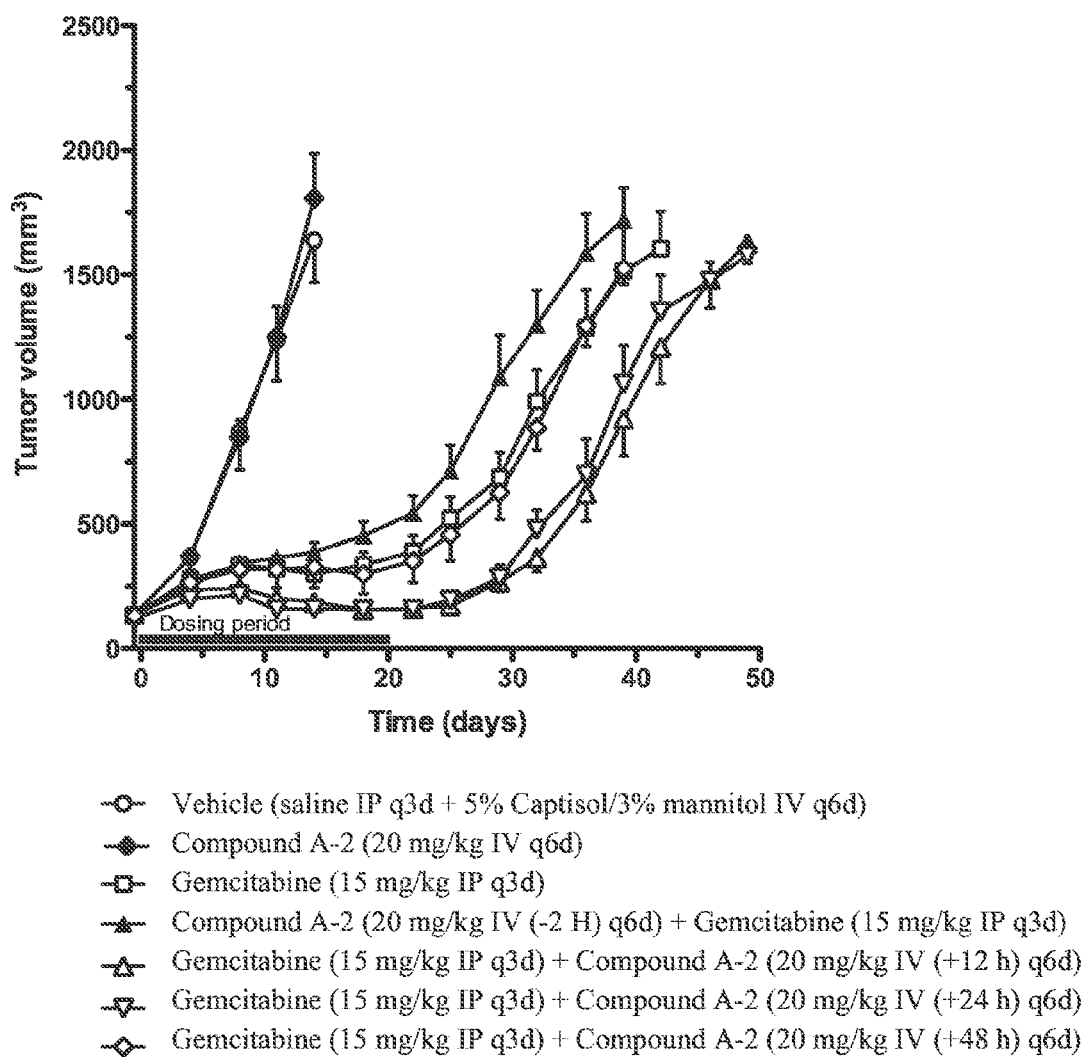
FIG. 2 shows the optimization of intravenous Compound A-2 dose schedule in combination with gemcitabine in vivo. Nude mice bearing PSN1 human pancreatic cancer xenografts were dosed with Compound A-2 or gemcitabine alone or in combination on different schedules, and tumor volumes were monitored for 49 days.

In a human pancreatic cancer xenograft model (PSN1), Compound A-2 (20 mg/kg, dosed every 6 days) was most effective when dosed 12 to 24 hours after administration of gemcitabine (15 mg/kg, dosed every 3 days) Dosing with Compound A-2 the within 12 hours of gemcitabine administration, or beyond 24 hours of gemcitabine administration, reduced efficacy. FIG. 2 shows the Compound A-2 dose schedule in combination with gemcitabine in vivo.

Dosing with Compound A-2 before gemcitabine, or 48 hours after gemcitabine, provided limited benefit over gemcitabine treatment. The addition of Compound A-2 to gemcitabine did not lead to increased body weight loss when compared with gemcitabine only treatment.

Figure 3:
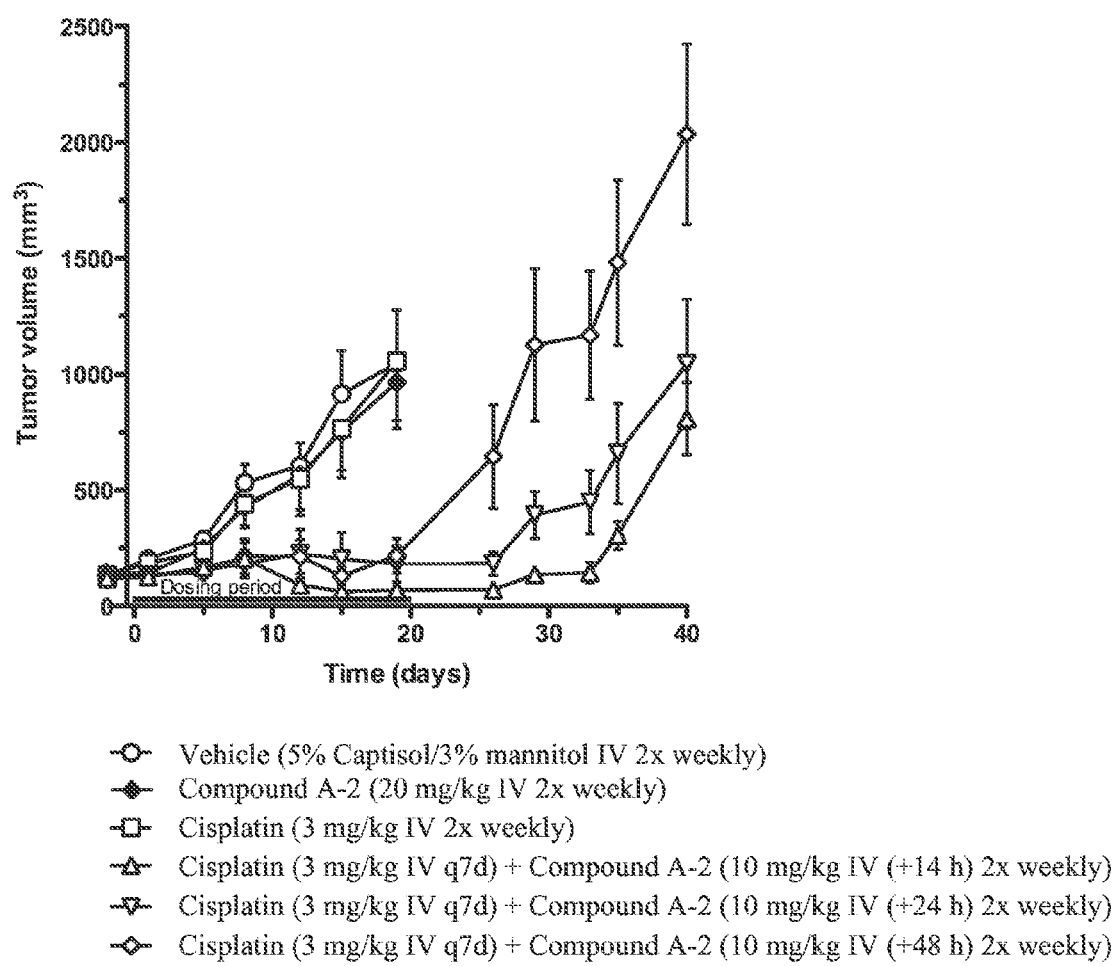
FIG. 3 shows the optimization of intravenous Compound A-2 dose schedule in combination with cisplatin in vivo. SCID mice bearing OD26749 primary human non-small cell lung cancer xenografts were dosed with Compound A-2 or cisplatin alone or in combination on different schedules, and tumor volumes were monitored for 40 days.

In a NSCLC xenograft model derived from primary human tumor tissue, in SCID mice, Compound A-2 the (10 mg/kg, dosed twice weekly) was most effective when dosed 14 hours after administration of cisplatin (3 mg/kg, dosed weekly) as shown in FIG. 3. Under these conditions, marked tumor regression (43%) and substantial growth delay was observed. This contrasts with the effects of either agent given alone, where neither Compound A-2 the nor cisplatin had any meaningful impact on tumor growth (≤10% tumor growth inhibition). This combination was well tolerated with <2% body weight loss at nadir, though animals did not gain weight as rapidly as cisplatin only treated animals.

These studies demonstrate strong schedule dependence for intravenously administered Compound A-2. For combinations with either gemcitabine or cisplatin, efficacy was maximal when Compound A-2 was dosed 12 to 24 hours after the DNA-damaging agent.

Example 3—Phase I Trial of First-in-Class Ataxia Telangiectasia-Mutated and Rad3-Related (ATR) Inhibitor a Compound of Formula A-2 as Monotherapy (Mono) or in Combination with Carboplatin (CP) in Advanced Cancer Patients (Pts) with Preliminary Evidence of Target Modulation and Antitumor Activity ATR mediates the homologous recombination DNA repair pathway and cellular response to replication stress. The compound of Formula A-2 (Compound A-2) is a potent and selective inhibitor of ATR ($K_i$<0.2 nM) that showed enhanced synergy of ATR inhibition with cytotoxic chemotherapy, and potential monotherapy ATR inhibitor activity in tumor cell lines with high levels of replication stress, such as defects in the DNA damage repair (DDR) pathway (e.g. ATM loss). A Phase I dose-escalation trial of Compound A-2 was undertaken to assess the safety and tolerability of an ATR inhibitor as a monotherapy and in combination with DNA-damaging chemotherapy, to show evidence of ATR inhibition in tumor tissue, and to explore antitumor activity.

Pts with advanced solid tumors enrolled in 2 sequential parts. In Part A, pts received IV Compound A-2 mono weekly in single-pt cohorts, with 3+3 cohorts initiated if grade (G) ≥2 Compound A-2 related adverse events (AEs) were observed. In Part B, pts received CP on day 1 and Compound A-2 on days 2 and 9 of a 21-day cycle in a 3+3 dose-escalation design (Compound A-2 on days 2 and 9 every 3 weeks and CP on day 1 every 3 weeks). Paired Compound A-2 tumor biopsies were obtained in selected CP treated pts pre- and post-Compound A-2, and pS345 Chk1 levels were assessed by immunohistochemistry (IHC).

Results: 25 pts were treated; M/F 10/15; median age 67 yr (range 49-76 yr); ECOG PS 0/1: 11/14. In Part A, 11 pts (colorectal [CRC; n=2]; mesothelioma [n=2]; other [n=7]; median prior lines of therapy=3) received Compound A-2 at 60 mg/m$^2$ (n=1), 120 mg/m$^2$ (n=2), 240 mg/m$^2$ (n=1) and 480 mg/m$^2$ (n=7). In Part B, 14 pts (CRC [n=6]; ovarian [n=2]; other [n=6]; median prior lines of therapy=3) received Compound A-2 240 mg/m$^2$+CP AUC 5 mg/mL·min (n=3; dose level 1 [DL1]), Compound A-2 120 mg/m$^2$+CP AUC 5 mg/mL·min (n=3; DL2), Compound A-2 120 mg/m$^2$+CP AUC 4 mg/mL·min (n=3; DL3) and Compound A-2 90 mg/m$^2$+CP AUC 5 mg/mL·min (n=5; DL4). In Part A, no dose-limiting toxicities (DLT) or drug-related G3-4 AEs were seen. In Part B, 2 pts had DLT: G4 neutropenia and fever (n=1; DL1) and G3 hypersensitivity (n=1; DL2). Non-DLT G3-4 AEs were neutropenia (n=4; DL1-2) and thrombocytopenia (n=1; DL2) requiring dose delays. No G3-4 AEs were seen at DL3-4. RP2D cohort expansion is ongoing at DL4. Compound A-2 displayed linear AUC and $C_{max}$ at all DLs; median half-life was 16 h with no accumulation. Based on preclinical models, efficacious exposures were achieved. When combined with CP, DL1 and DL2 showed similar Compound A-2 exposure, suggesting no apparent drug interactions. Decreased Chk1 phosphorylation was seen in 2/2 paired tumor biopsies (74% at DL4; 94% at DL2). An advanced CRC pt (serosal disease and abdominal lymphadenopathy; 3 prior lines of chemotherapy) with complete ATM loss by IHC achieved RECIST complete response to Compound A-2 mono at 60 mg/m$^2$ and remains on trial at 59+ wks. RECIST stable disease (SD) was seen with Compound A-2 mono in 4 pts (median duration of SD=11 wks [11-17.4 wks]) and Compound A-2+CP in 7 pts, who were still ongoing (duration of SD=5+ to 20+ wks), including several pts who had progressed on prior platinum therapy.

Example 4. Phase I Trial of First-in-Class Ataxia Telangiectasia-Mutated and Rad3-Related (ATR) Inhibitor a Compound of Formula A-2 as Monotherapy (Mono)

This example further describes the Phase I dose-escalation trial of a compound of Formula A-2 (Compound A-2) to assess the safety and tolerability of an ATR inhibitor as a monotherapy in Example 3.

The study included 17 patients. The subject demographic and baseline characteristics are shown in Table 1.

TABLE 1

Subject demographics and baseline characteristics.

| Baseline Characteristics | |
|---|---|
| Age, mean (SD), years | 63.4 (10.3) |
| Sex, n (%) | |
| Male | 7 (41.2) |
| Female | 10 (58.8) |
| Race, n (%) | |
| White | 16 (94.1) |
| Black or African American | 0 |
| Asian | 0 |
| Other | 1 (5.9) |
| ECOG PS at baseline, n (%) | |
| 0 | 4 (23.5) |
| 1 | 13 (76.5) |
| Primary malignancy, n (%) | |
| NSCLC | 0 |
| Breast cancer | 1 (5.9) |
| Ovarian cancer | 1 (5.9) |
| Colorectal cancer | 3 (17.6) |
| Other | 12 (70.6) |

Figure 12:
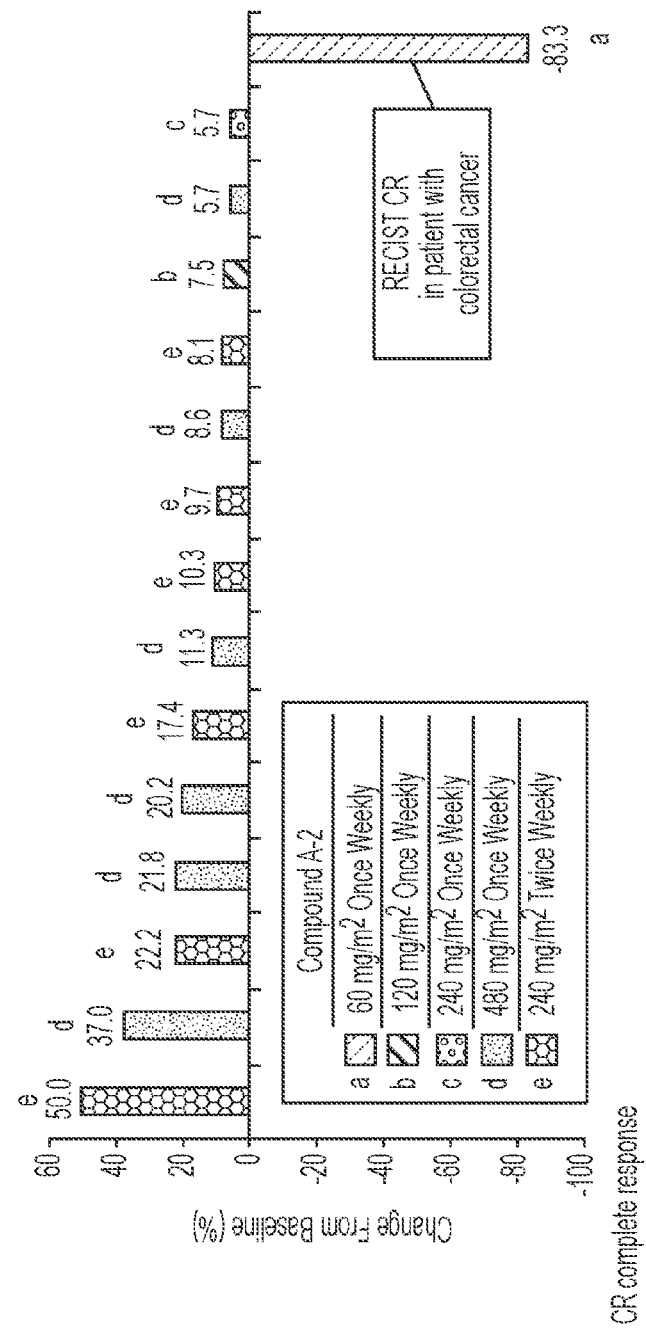
FIG. 12 shows tumor response showing changes from baseline in cancer subjects who received treatment of Compound A-2 as a monotherapy.

The 17 subjects received once weekly intravenous doses of Compound A-2 ranging from 60 to 480 mg/m² or twice weekly intravenous doses of 240 mg/m² of Compound A-2. Eleven of the subjects were given a once weekly dosage of Compound A-2 as a monotherapy. Six of the subjects were given a twice weekly dosage of Compound A-2 as a monotherapy. For the once weekly dosage, there were no dose limiting toxicities (DLTs) and adverse events began at a dose of 480 mg/m² as shown in Table 2. DLTs were defined according to the National Cancer Institute (NCI) CTCAE (Version 4). FIG. 12 shows tumor response showing changes from baseline in cancer subjects who received treatment of Compound A-2 as a monotherapy, and FIG. 13 shows duration of progression-free survival (PFS).

Figure 4:
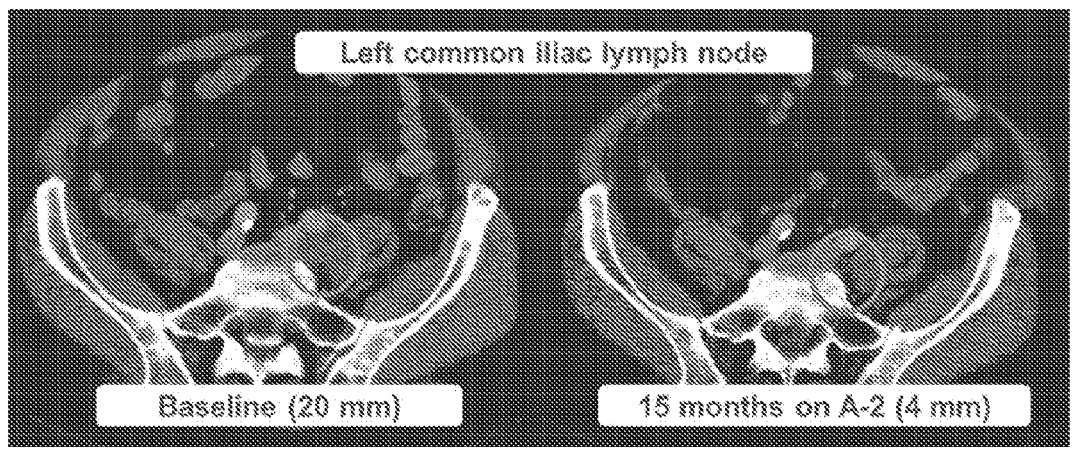
FIG. 4 shows radiographs of the left common iliac lymph node before treatment (left) and after 15 months of treatment (right) with 60 mg/m² of Compound A-2 weekly monotherapy.

As noted in Example 3, a subject with KRAS and BRAF wildtype metastatic colorectal cancer with serosal disease and abdominal lymphadenopathy had a RECIST complete response after treatment with 60 mg/m² monotherapy (weekly) of Compound A-2. The colorectal cancer had a complete loss of ATM signaling based on IHC analysis. There was loss of MLH1 and PMS2, and weak heterogeneous staining of MSH2 and MSH6 on immunohistochemistry. Targeted and whole exome next-generation sequencing (NGS) revealed a somatic truncating mutation in MLH1 at position p.Lys33*/c.97A>T, which was likely to contribute to tumor microsatellite instability (MSI). PTEN and CTNNB1 somatic mutations were also detected on NGS. The subject remains on trial with ongoing RECIST complete response lasting more than 28 months. Radiographs of the left common iliac lymph node before treatment (i.e., baseline) and after 15 months of treatment is shown in FIG. 4.

Prior to treatment with Compound A-2, the subject received 4 lines of treatment. The first line of treatment was folinic acid, Fluorouracil, irinotecan, and cetuximab, which resulted in a RECIST partial response. The second line of treatment was folinic acid, fluorouracil, oxaliplatin, and Avastin, which resulted in a RECIST partial response. The third line of treatment was fluorouracil and Avastin, which resulted in a RECIST progression. The fourth line of treatment was Capecitabine and mitomycin which resulted in a RECIST progression.

Figure 13:
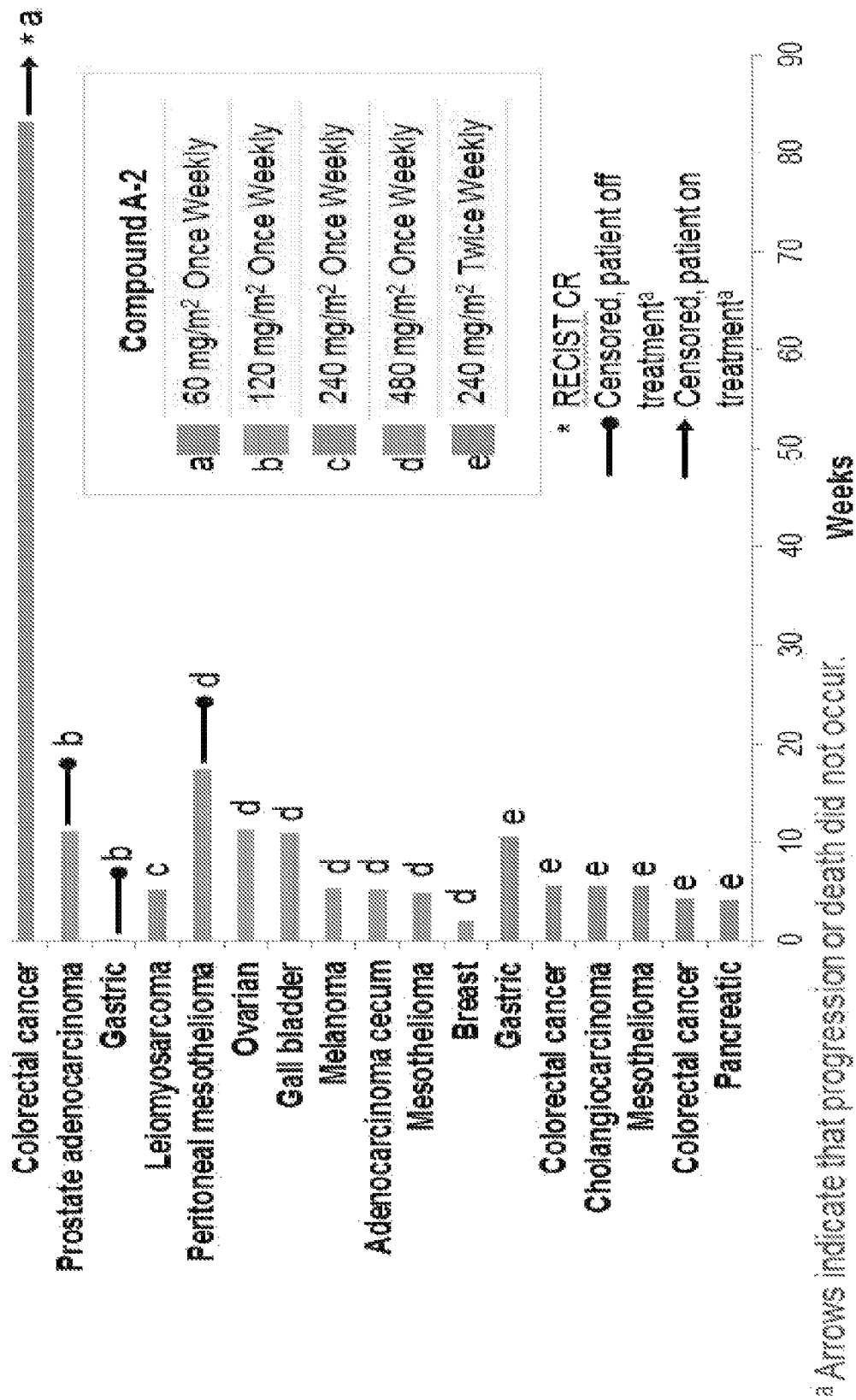
FIG. 13 shows duration of progression-free survival (PFS) from start of treatments of Compound A-2 as a monotherapy in subjects having cancer.

The tumor response and duration of progression free survival for several cancers are shown in FIGS. 12 and 13, respectively.

Example 5. Phase I Trial of First-in-Class Ataxia Telangiectasia-Mutated and Rad3-Related (ATR) Inhibitor a Compound of Formula A-2 in Combination with Carboplatin (CP) in Advanced Cancer Patients (Pts) with Preliminary Evidence of Target Modulation and Antitumor Activity This example further describes the Phase I dose-escalation trial of a compound of Formula A-2 (Compound A-2) in combination with carboplatin in Example 3.

TABLE 2

Compound A-2 monotherapy weekly treatment related adverse events.

| | mg/m² | | | | | | | | | | |
|---|---|---|---|---|---|---|---|---|---|---|---|
| | 60 Once Weekly (n = 1) n (%) | | 120 Once Weekly (n = 2) n (%) | | 240 Once Weekly (n = 1) n (%) | | 480 Once Weekly (n = 7) n (%) | | 240 Twice Weekly (n = 6) n (%) | | Total (N = 17) n (%) | |
| Event | Grade ≥3 | All Grades | Grade ≥3 | All Grades | Grade ≥3 | All Grades | Grade ≥3 | All Grades | Grade ≥3 | All Grades | Grade ≥3 | All Grades |
| Any Event | 0 | 1 (100) | 0 | 1 (50.0) | 0 | 0 | 0 | 7 (100) | 1 (16.7) | 6 (100) | 1 (5.9) | 15 (88.2) |
| Flushing | 0 | 0 | 0 | 0 | 0 | 0 | 0 | 3 (42.9) | 0 | 1 (16.7) | 0 | 4 (23.5) |
| Catheter site related reaction | 0 | 0 | 0 | 0 | 0 | 0 | 0 | 0 | 0 | 2 (33.3) | 0 | 2 (11.8) |
| Nausea | 0 | 0 | 0 | 0 | 0 | 0 | 0 | 2 (28.6) | 0 | 0 | 0 | 2 (11.8) |
| Pruritus | 0 | 0 | 0 | 0 | 0 | 0 | 0 | 2 (28.6) | 0 | 0 | 0 | 2 (11.8) |
| Infusion related reaction | 0 | 0 | 0 | 0 | 0 | 0 | 0 | 1 (14.3) | 0 | 1 (16.7) | 0 | 2 (11.8) |
| Headache | 0 | 0 | 0 | 0 | 0 | 0 | 0 | 2 (28.6) | 0 | 0 | 0 | 2 (11.8) |

The study included 19 patients. The subject demographic and baseline characteristics are shown in Table 3.

TABLE 3

Subject demographics and baseline characteristics.

| Baseline Characteristics | Part B (N = 19) |
|---|---|
| Age, mean (SD), years | 63.3 (8.7) |
| Sex, n (%) | |
| Male | 7 (36.8) |
| Female | 12 (63.2) |
| Race, n (%) | |
| White | 18 (94.7) |
| Black or African American | 0 |
| Asian | 0 |
| Other | 1 (5.3) |
| ECOG PS at baseline, n (%) | |
| 0 | 7 (36.8) |
| 1 | 12 (63.2) |
| Primary malignancy, n (%) | |
| NSCLC | 1 (5.3) |
| Breast cancer | 1 (5.3) |
| Ovarian cancer | 2 (10.5) |
| Colorectal cancer | 8 (42.1) |
| Other | 7 (36.8) |

The 15 subjects received a three week cycle of carboplatin on day 1, Compound A-2 on day 2, 24 hours after treatment with carboplatin, and Compound A-2 on day 9. The dose escalation and dose limiting toxicities are shown in Table 4.

TABLE 4

Dose escalation of Compound A-2 combination therapy.

| Cohort | A-2 Dose (mg/m$^2$) | Carboplatin Dose (AUC) | No. Subjects (Enrolled/ DLT evaluable) | DLTs |
|---|---|---|---|---|
| 1 | 240 | 5 mg/mL · min | 3/3 | 1 (febrile neutropenia) |
| 2 | 120 | 5 mg/mL · min | 3/3 | 1 (acute hypersensitivity) |
| 3 | 120 | 4 mg/mL · min | 3/3 | 0 |
| 4 | 90 | 5 mg/mL · min | 10/10 | 1 (febrile neutropenia) |

The adverse events are shown in Tables 5A-5B and include neutropenia and thrombocytopenia, which were believed to be a result of the mechanism of action of ATR when administered in combination with a DNA damaging agent.

TABLE 5A

Treatment related adverse events for combination therapy.

| | A-2 (mg/m$^2$) + Carboplatin (AUC, mg/mL · min) | | | | | | | | |
|---|---|---|---|---|---|---|---|---|---|
| | 240 + AUC5 (N = 3) | | 120 + AUC5 (N = 3) | | 120 + AUC4 (N = 3) | | 90 + AUC5 (N = 6) | | Total (N = 15) |
| Adverse Event | ≥3 | All | ≥3 | All | ≥3 | All | ≥3 | All | ≥3 | All |
| Anemia | 0 | 3 | 0 | 2 | 0 | 1 | 0 | 3 | 0 | 9 |
| Neutropenia | 2 | 3 | 1 | 2 | 0 | 0 | 1 | 2 | 4 | 7 |
| Thrombocytopenia | 1 | 3 | 0 | 1 | 0 | 1 | 0 | 2 | 1 | 7 |
| Nausea | 0 | 3 | 0 | 2 | 0 | 1 | 0 | 1 | 0 | 7 |
| Fatigue | 0 | 2 | 0 | 1 | 0 | 0 | 0 | 3 | 0 | 6 |
| Flushing | 0 | 1 | 1 | 1 | 0 | 1 | 0 | 0 | 1 | 3 |
| Vomiting | 0 | 2 | 0 | 0 | 0 | 0 | 0 | 0 | 0 | 2 |
| Alopecia | 0 | 0 | 0 | 0 | 0 | 0 | 0 | 2 | 0 | 2 |
| Headache | 0 | 2 | 0 | 0 | 0 | 0 | 0 | 0 | 0 | 2 |
| Neuropathy peripheral | 0 | 2 | 0 | 0 | 0 | 0 | 0 | 0 | 0 | 2 |
| Hypertension | 1 | 1 | 0 | 0 | 0 | 0 | 0 | 0 | 1 | 1 |
| Respiratory tract infection | 1 | 1 | 0 | 0 | 0 | 0 | 0 | 0 | 1 | 1 |

TABLE 5B

Treatment related adverse events for combination therapy.

| | A-2 (mg/m$^2$) + Carboplatin (AUC) | | | | | | | | | |
|---|---|---|---|---|---|---|---|---|---|---|
| | 240 + 5 (n = 3) n (%) | | 120 + 5 (n = 3) n (%) | | 120 + 4 (n = 3) n (%) | | 90 + 5 (n = 10) n (%) | | Total (N = 19) n (%) | |
| Event | Grade ≥3 | All Grades | Grade ≥3 | All Grades | Grade ≥3 | All Grades | Grade ≥3 | All Grades | Grade ≥3 | All Grades |
| Any Event | 2 (66.7) | 3 (100) | 2 (66.7) | 3 (100) | 0 | 2 (66.7) | 1 (10.0) | 9 (90.0) | 5 (26.3) | 17 (89.5) |
| Anemia | 0 | 3 (100) | 0 | 2 (66.7) | 0 | 1 (33.3) | 0 | 4 (40.0) | 0 | 10 (52.6) |
| Neutropenia | 2 (66.7) | 3 (100) | 1 (33.3) | 2 (66.7) | 0 | 0 | 1 (10.0) | 3 (30.0) | 4 (21.1) | 8 (42.1) |
| Nausea | 0 | 3 (100) | 0 | 2 (66.7) | 0 | 1 (33.3) | 0 | 3 (30.0) | 0 | 9 (47.4) |
| Thrombocytopenia | 1 (33.3) | 3 (100) | 0 | 1 (33.3) | 0 | 1 (33.3) | 0 | 2 (20.0) | 1 (5.3) | 7 (36.8) |
| Fatigue | 0 | 2 (66.7) | 0 | 1 (33.3) | 0 | 0 | 0 | 4 (40.0) | 0 | 7 (36.8) |
| Pruritus | 0 | 1 (33.3) | 0 | 0 | 0 | 1 (33.3) | 0 | 1 (10.0) | 0 | 3 (15.8) |
| Flushing | 0 | 1 (33.3) | 0 | 0 | 0 | 1 (33.3) | 0 | 1 (10.0) | 0 | 3 (15.8) |
| Vomiting | 0 | 2 (66.7) | 0 | 0 | 0 | 0 | 0 | 0 | 0 | 2 (10.5) |
| Infusion site erythema | 0 | 1 (33.3) | 0 | 1 (33.3) | 0 | 0 | 0 | 0 | 0 | 2 (10.5) |
| Alopecia | 0 | 0 | 0 | 0 | 0 | 0 | 0 | 2 (20.0) | 0 | 2 (10.5) |
| Headache | 0 | 2 (66.7) | 0 | 0 | 0 | 0 | 0 | 0 | 0 | 2 (10.5) |
| Neuropathy peripheral | 0 | 2 (66.7) | 0 | 0 | 0 | 0 | 0 | 0 | 0 | 2 (10.5) |
| Hypersensitivity | 0 | 1 (33.3) | 1 (33.3) | 1 (33.3) | 0 | 0 | 0 | 0 | 1 (5.3) | 2 (10.5) |
| Infusion related reaction | 0 | 0 | 0 | 1 (33.3) | 0 | 0 | 0 | 1 (10.0) | 0 | 2 (10.5) |

Figure 5A:
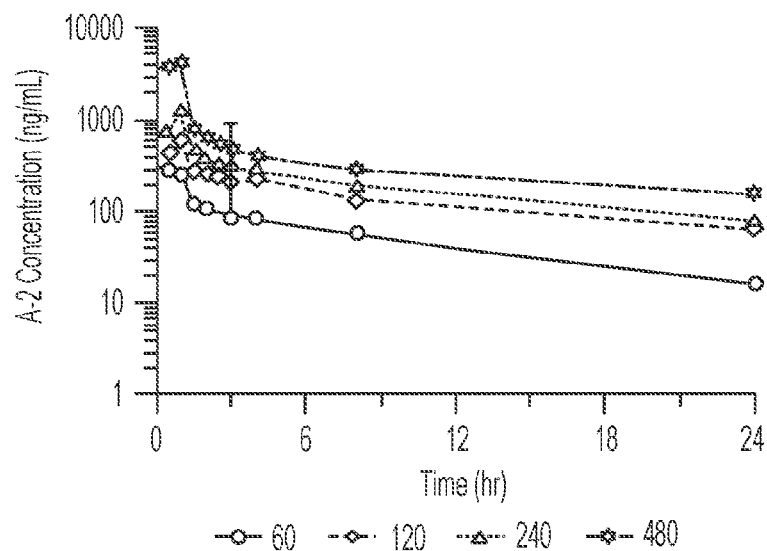
FIG. 5A shows a graph of plasma concentration versus time for Compound A-2 monotherapy.
Figure 5B:
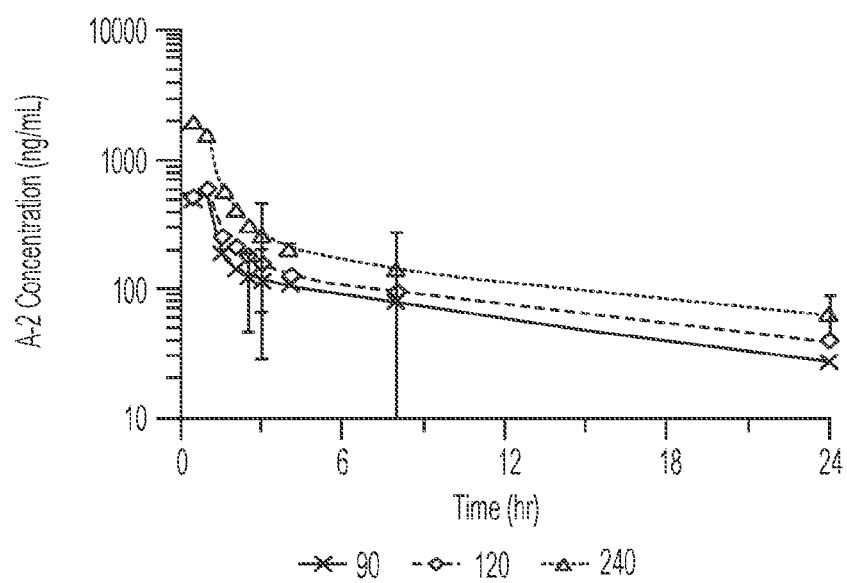
FIG. 5B shows a graph of plasma concentration versus time for combination therapy with carboplatin and Compound A-2.

The Compound A-2 plasma concentration-time profiles were similar with monotherapy and in combination with carboplatin as shown in FIG. 5A and FIG. 5B, respectively. This suggested that there was no interaction of Compound A-2 and carboplatin. In addition, exposure ($AUC_{inf}$ and $C_{max}$) increased proportionally with increasing dose. Terminal elimination half-life ($t_{1/2}$) was about 16 hours.

Figure 6:
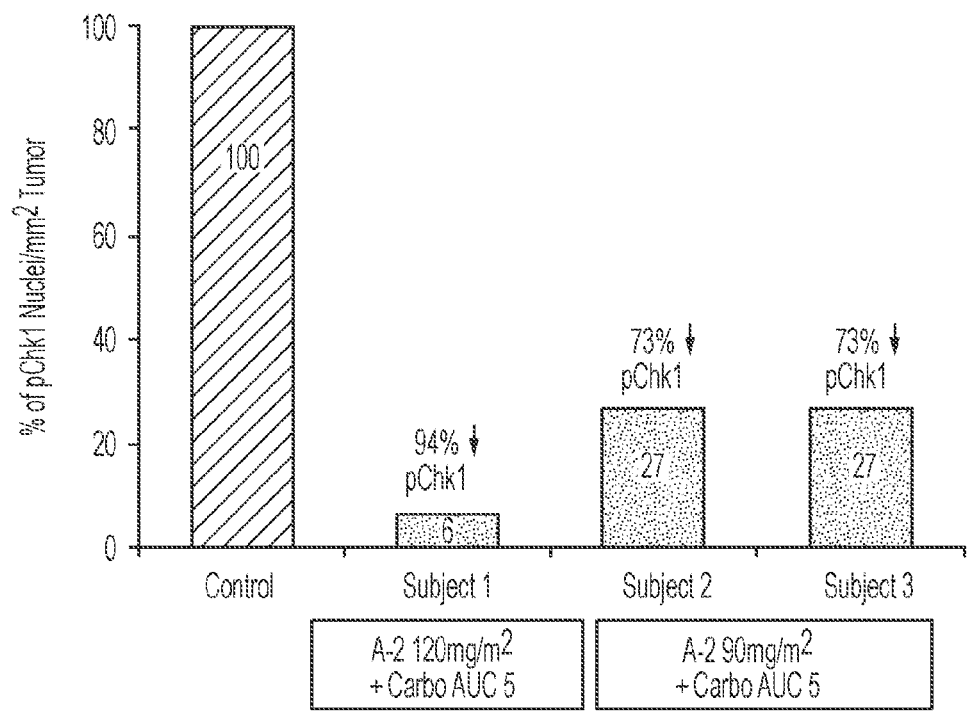
FIG. 6 shows a graph of percentage of pChk1 in the nuclei of cancer cells/mm² tumor before exposure to Compound A-2 (pre-dose) and after exposure to Compound A-2 (post-dose) for various subjects.

As noted in Example 3, phosphorylated Chk1 was used as a biomarker in paired tumor biopsies of three subjects to determine the efficacy of the combination therapy. A first tumor biopsy was taken on day 2, two hours before Compound A-2 administration, and a second tumor biopsy was taken two hours after Compound A-2 administration. The amount of pChk1 in the nuclei of cancer cells/mm$^2$ tumor in the first biopsy was set to 100% and used to normalize the amount in the second biopsy. As shown in FIG. 6, subject 1 was given target AUC of 5 mg/mL·min of carboplatin and 120 mg/m$^2$ of Compound A-2 and had a 94% decrease in pChk1. Subjects 2 and 3 were given target AUC of 5 mg/mL·min of carboplatin and 90 mg/m$^2$ of Compound A-2 and had a 73% decrease in pChk1.

Figure 7:
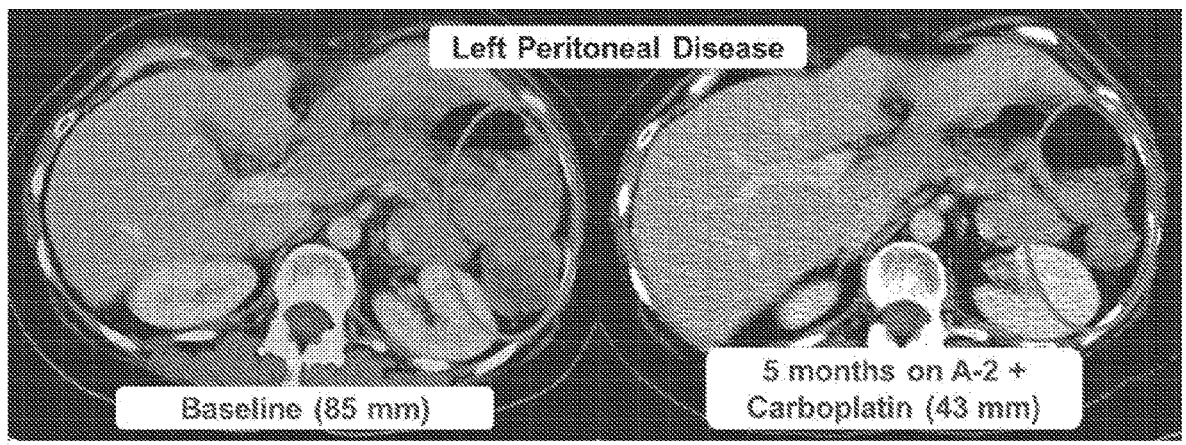
FIG. 7 shows radiographs of left peritoneal disease before treatment (left) and after 5 months of treatment (right) after combination treatment with a target AUC of 5 mg/mL·min of carboplatin on day 1 and 90 mg/m² of Compound A-2 on day 2, 24 hours after treatment with carboplatin, and 90 mg/m² of Compound A-2 on day 9.

As noted in Example 3, a subject with platinum and antimetabolite refractory metastatic high grade serous ovarian cancer having gBRCA1 Q1111Nfs*5 mutation and TP53 Y220C missense deleterious somatic mutation with peritoneal, liver and nodal disease had a RECIST partial response after combination treatment target AUC of 5 mg/mL·min of carboplatin on day 1 and 90 mg/m$^2$ of Compound A-2 on day 2, 24 hours after treatment with carboplatin, and 90 mg/m$^2$ of Compound A-2 on day 9. The subject remains on trial with ongoing RECIST partial response lasting more than 6 months. Radiographs of left peritoneal disease before treatment (i.e., baseline) and after 5 months of treatment is shown in FIG. 7.

Prior to treatment with Compound A-2, the subject had debulking surgery before receiving 7 lines of treatment. The seventh line of treatment was carboplatin and gemcitabine, which resulted in progressive disease after 3 cycles. Other lines of treatment included Talazoparib (BMN 673; Biomarin Pharmaceuticals) monotherapy, which resulted in progressive disease after 10 months; Olaparib (AstraZeneca) and AKT inhibitor AZD5363 (AstraZeneca), which resulted in progressive disease after 5 months; and αFR inhibitor, which resulted in progressive disease after 5 months.

Figure 14:
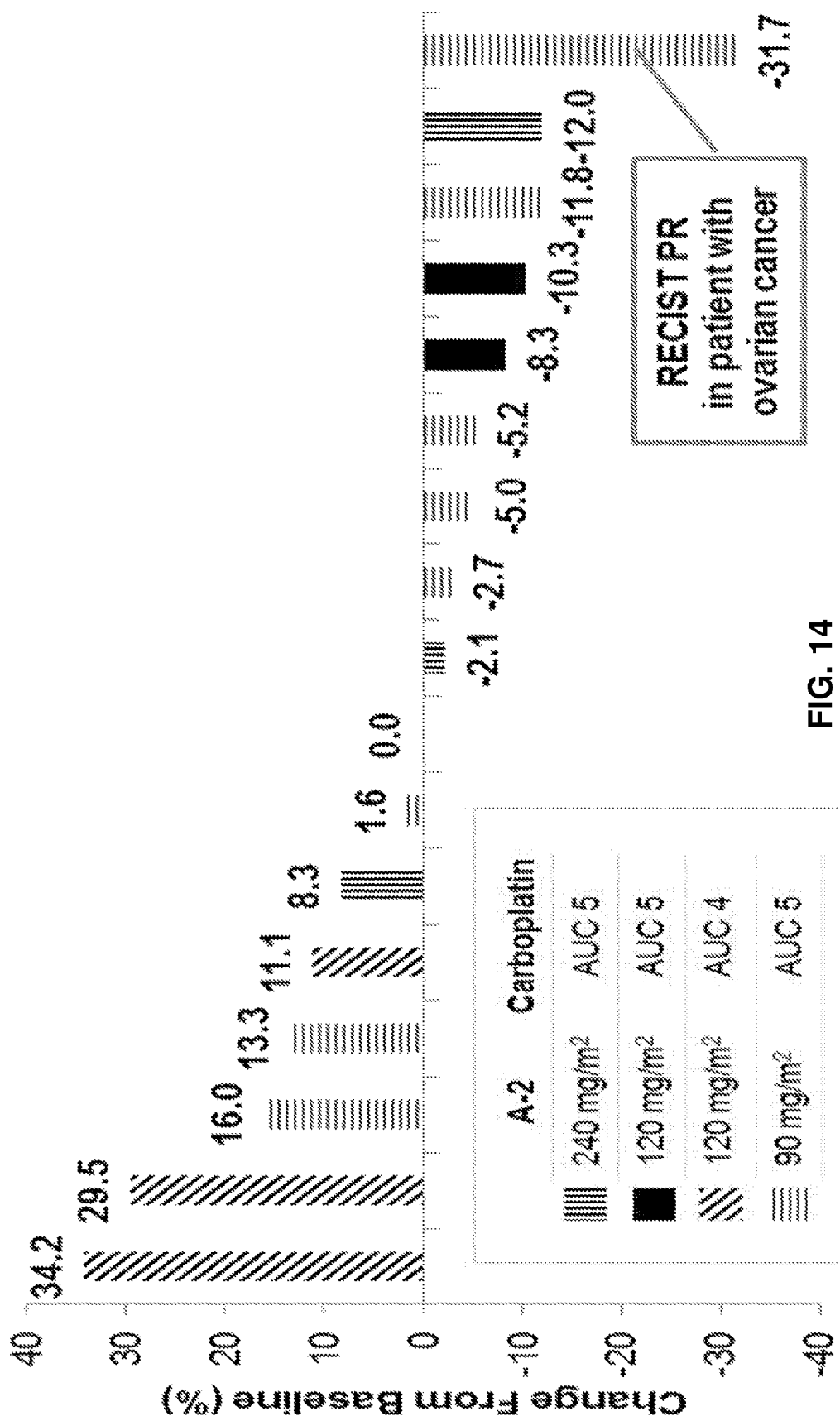
FIG. 14 shows tumor response showing changes from baseline in cancer subjects who received treatment of Compound A-2 and carboplatin.
Figure 15:
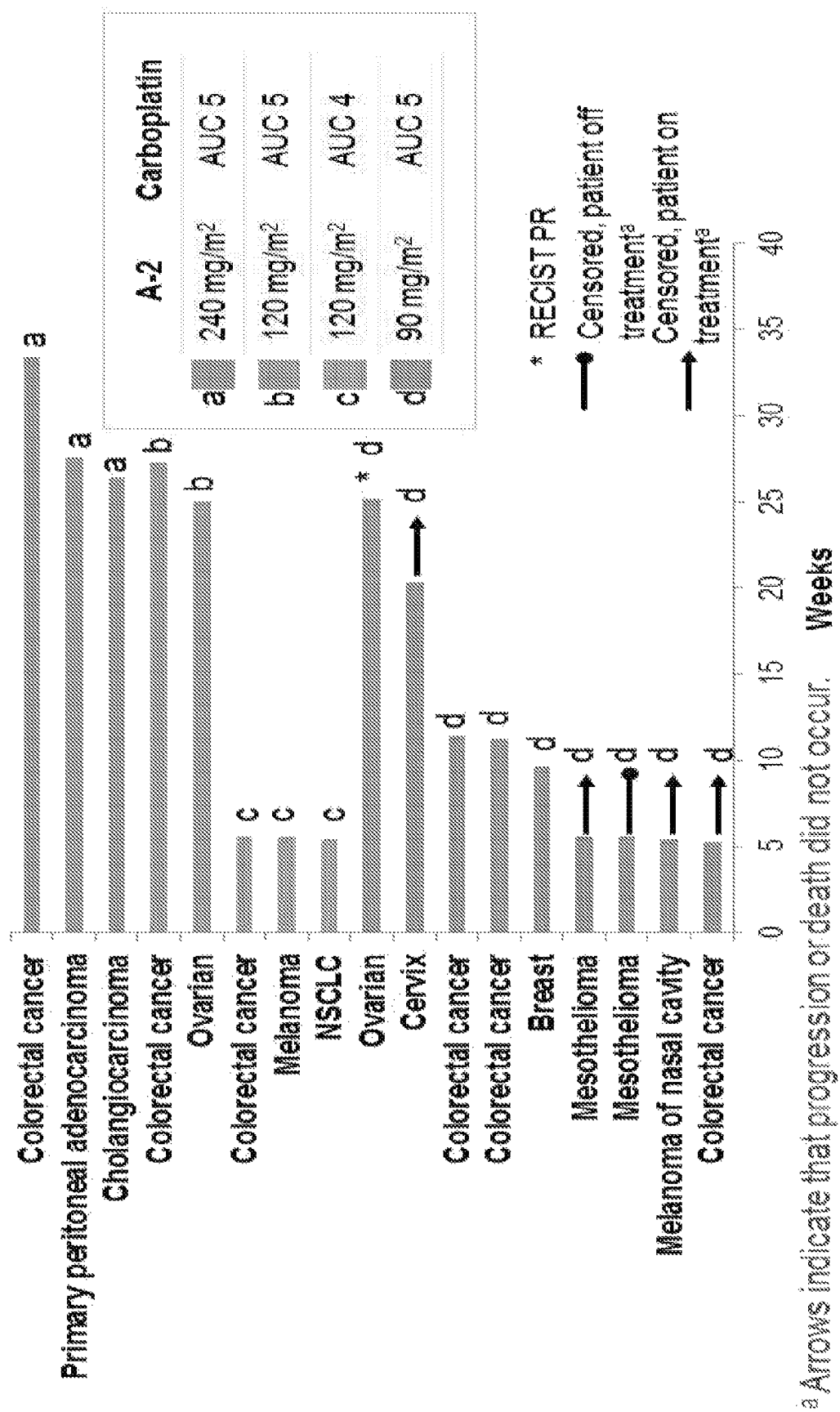
FIG. 15 shows duration of progression-free survival (PFS) from start of treatments of Compound A-2 and carboplatin in subjects having cancer.

The tumor response and duration of progression free survival for several cancers are shown in FIGS. 14 and 15, respectively.

Tumor response of subjects 1, 2, and 3 shown in FIG. 6 is summarized below:

|  | Treatment | | |
|---|---|---|---|
|  | Compound A-2 120 mg/m$^2$ + carboplatin AUC 5 mg/mL · min | Compound A-2 90 mg/m$^2$ + carboplatin AUC 5 mg/mL · min | |
|  | Tumor | | |
|  | Ovarian (Subject 1) | Ovarian (Subject 2) | Breast (Subject 3) |
| PFS (progression- free survival) (days) | 175 | 176 | 67 |
| Response | SD (Stable Disease) | PR (Partial Response) | SD (Stable Disease) |

Example 6. Phase I Trial of First-in-Class Ataxia Telangiectasia-Mutated and Rad3-Related (ATR) Inhibitor a Compound of Formula A-2 as a Monotherapy (Mono) or in Combination with Carboplatin (CP) in Advanced Cancer Patients (Pts)

ATR mediates the homologous recombination DNA repair pathway and cellular response to replication stress. A compound of Formula A-2 (Compound A-2) is a potent, selective inhibitor of ATR that enhanced ATR inhibition with cytotoxic chemotherapy and inhibited ATR in tumor cell lines with DNA repair pathway defects. Pharmacokinetics (PK), pharmacodynamics (PD), tolerability, and efficacy of a compound of Formula A-2±CP were assessed in a Phase I dose escalation trial.

Patients (pts) with advanced solid tumors measurable by RECIST 1.1 were enrolled in 2 parts. In part A, single pt cohorts received a compound of Formula A-2 once weekly in 21-day cycles with 3+3 dose escalation cohorts being implemented if grade 2 drug-related adverse events (AEs) occurred. In part B, 3+3 pt cohorts received CP on day 1+a compound of Formula A-2 on days 2 and 9 of each 21-day cycle. If no dose limiting toxicities (DLTs) occurred after 1 cycle, dose escalation was permitted in a new cohort. If a DLT was reported, the cohort was expanded to include 3 additional pts with subsequent dose escalation being permitted if no further DLTs occurred. Paired pre- and post-treatment biopsies from selected pts in part B were assessed for pCHK1 levels by immunohistochemistry. Models based on preclinical and clinical data were used to simulate hematologic toxicities and pCHK1 inhibition for pts treated with a compound of Formula A-2 and CP.

Twenty six (26) pts (10 males and 16 females) of median age, 68 years (range 49-76 years) in A and 65 yrs (range 49-74 yrs) in B, with Eastern Cooperative Oncology Group (ECOG) performance status 0/1: 9/17 were treated according to the above protocols using the dosage levels (DLs) shown in the table below.

Dose levels (DLs) were:

| DL | A compound of Formula A-2 dose (mg/m$^2$) | CP dose (AUC, mg/ mL · min) | # pts treated |
|---|---|---|---|
| A1 | 60 | — | 1 |
| A2 | 120 | — | 2 |
| A3 | 240 | — | 1 |
| A4 | 480 | — | 7 |
| B1 | 240 | 5 | 3 |
| B2 | 120 | 5 | 3 |
| B3 | 120 | 4 | 3 |
| B4 | 90 | 5 | 6 |

No DLTs occurred in part A. In part B, DLTs were: grade 3/4 neutropenia (2 pts at dosage levels B1 and B2) and grade 3 hypersensitivity (1 pt at dosage level B2). Grade 3/4-related AEs occurred in 5 pts in part B across the various DLs, while none occurred in part A. The best responses were complete response (CR (n=1)) in part A and partial response (PR (n=1)) in part B. The pharmacokinetics (PK) for a compound of Formula A-2 was dose proportional both as a monotherapy and in combination with CP. Based on the above data, the recommended Phase II doses were established at DLs A4 and B4, with modeling predicting 73% pCHK1 inhibition and 5% and <1% probabilities of grade 4 neutropenia and thrombocytopenia, respectively, at DL B4. A compound of Formula A-2 exposures at B4 also led to tumor regression in preclinical models.

Example 7. Phase I Trial of First-in-Class Ataxia Telangiectasia-Mutated and Rad3-Related (ATR) Inhibitor a Compound of Formula A-2 in Combination with Cisplatin (CIS) in Patients (Pts) with Advanced Solid Tumors In this Example, patients (pts) received intravenous a compound of Formula A-2 (Compound A-2) in combination with CIS using a 3+3 dose escalation design. CIS was administered on day 1 and a compound of Formula A-2 was administered on days 2 and 9 in 21-day cycles. Twenty eight (28) pts (12 males and 16 females) of median age, 62.5 yrs (range 28-79 yrs), with Eastern Cooperative Oncology Group (ECOG) performance status 0-1 were treated. Primary tumors were breast (n=4), colorectal (n=3), ovarian (n=3), pancreatic (n=2), non-small cell lung cancer (NSCLC) (n=1), and other cancers (n=15). The following table describes the dosage levels (DLs) and various parameters for the various treatment cohorts.
Dose levels were:

| Cohort | Compound A-2 dose (mg/m$^2$) | Cisplatin dose (mg/m$^2$) | No. pts treated/ No. pts evaluable for dose limiting toxicities (DLTs) | No. DLTs |
| --- | --- | --- | --- | --- |
| 1 | 90 | 40 | 3/3 | |
| 2 | 140 | 40 | 4/3 | |
| 3 | 210 | 40 | 4/4 | |
| 4 | 210 | 60 | 10/10 | 1 (grade 3 elevated ALT) |
| 5 | 140 | 75 | 7/6 | 1 (grade 3 drug hypersensitivity) |

Non-DLT grade 3-4 treatment-related adverse events occurred in 11 pts, including nausea, cytopenia, hypotension, hypoalbuminemia, hypokalemia, elevated liver function tests (LFTs), and drug hypersensitivity. The maximum tolerated combination dose was not reached. However, the Compound A-2 dose escalation was stopped because pharmacokinetic (PK) exposures of Compound A-2 at the 140 mg/m$^2$ DL exceeded exposures previously shown in preclinical models, which resulted in robust target engagement and tumor regression in combination with CIS. There was no effect of CIS on the pharmacokinetics of Compound A-2. Compound A-2 terminal elimination half-life was about 16 hours and the Compound A-2 PK was proportional across the dosage ranges. RECIST partial responses were observed in 3 platinum-resistant/refractory pts (mesothelioma, ovarian, and triple-negative breast cancers) receiving Compound A-2 at 140 mg/m$^2$. Based on the above data, the recommended Phase II doses of Compound A-2 is 140 mg/m$^2$ and CIS is 75 mg/m$^2$ with RECIST antitumor responses observed in platinum-refractory pts.

Figure 8:
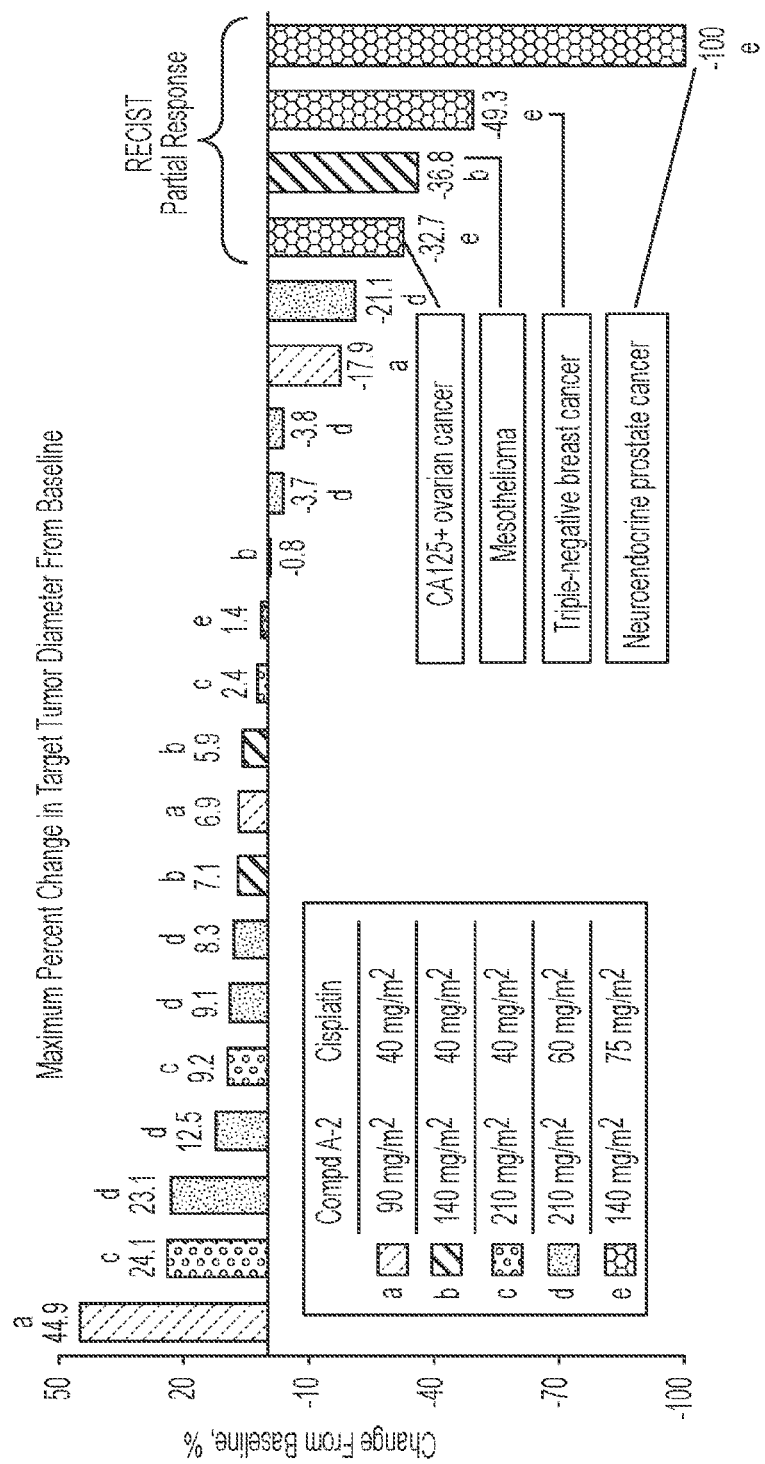
FIG. 8 shows a tumor response showing changes from baseline in cancer subjects who received treatment of Compound A-2 and cisplatin.
Figure 9:
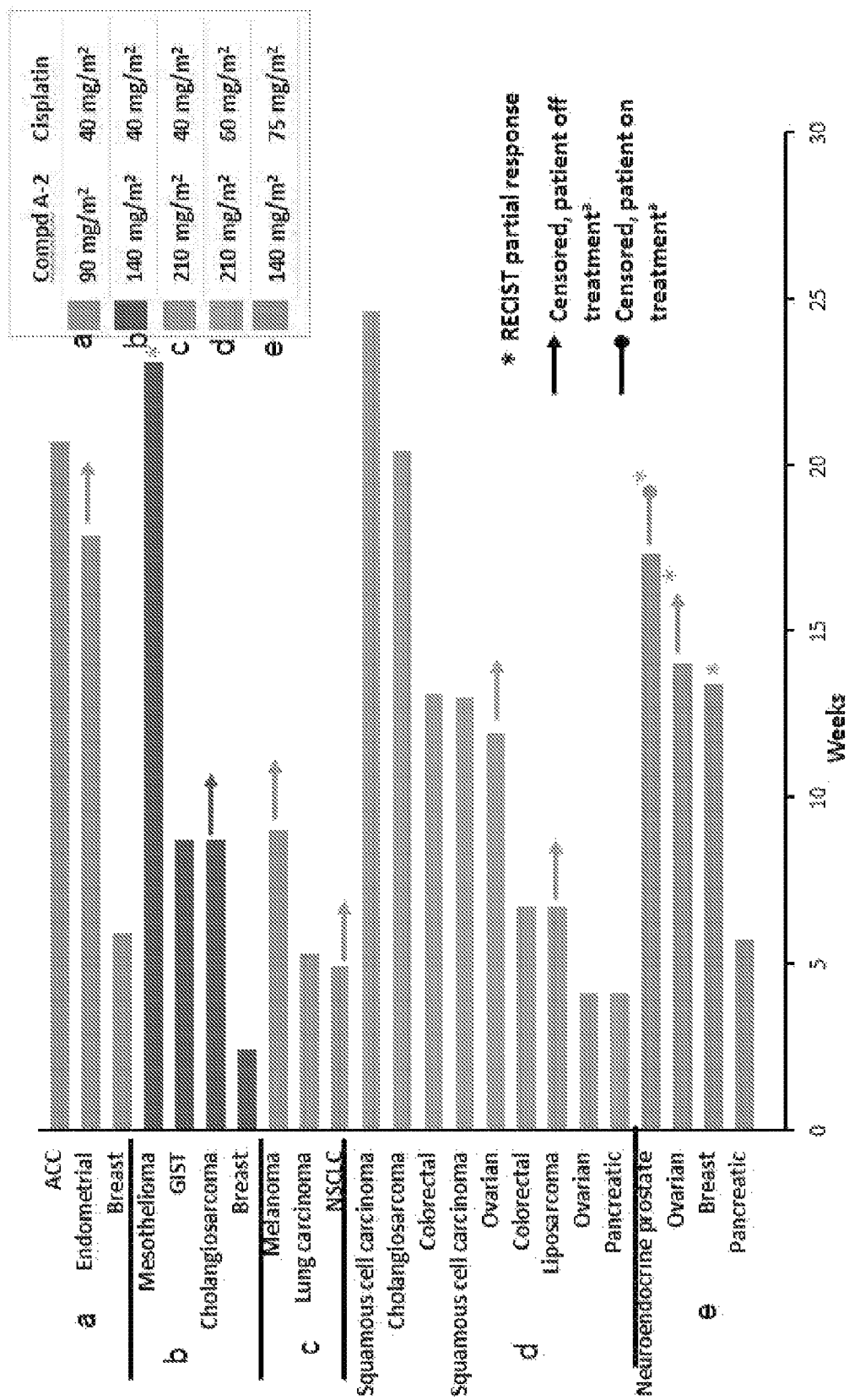
FIG. 9 shows duration of progression-free survival (PFS) from start of treatments of Compound A-2 and cisplatin in subjects having cancer.

FIG. 8 shows tumor response where maximum percent changes in target tumor diameter from baseline are depicted. Durations of progression free survival (PFS) in various cancers are shown in FIG. 9.

Figure 10:
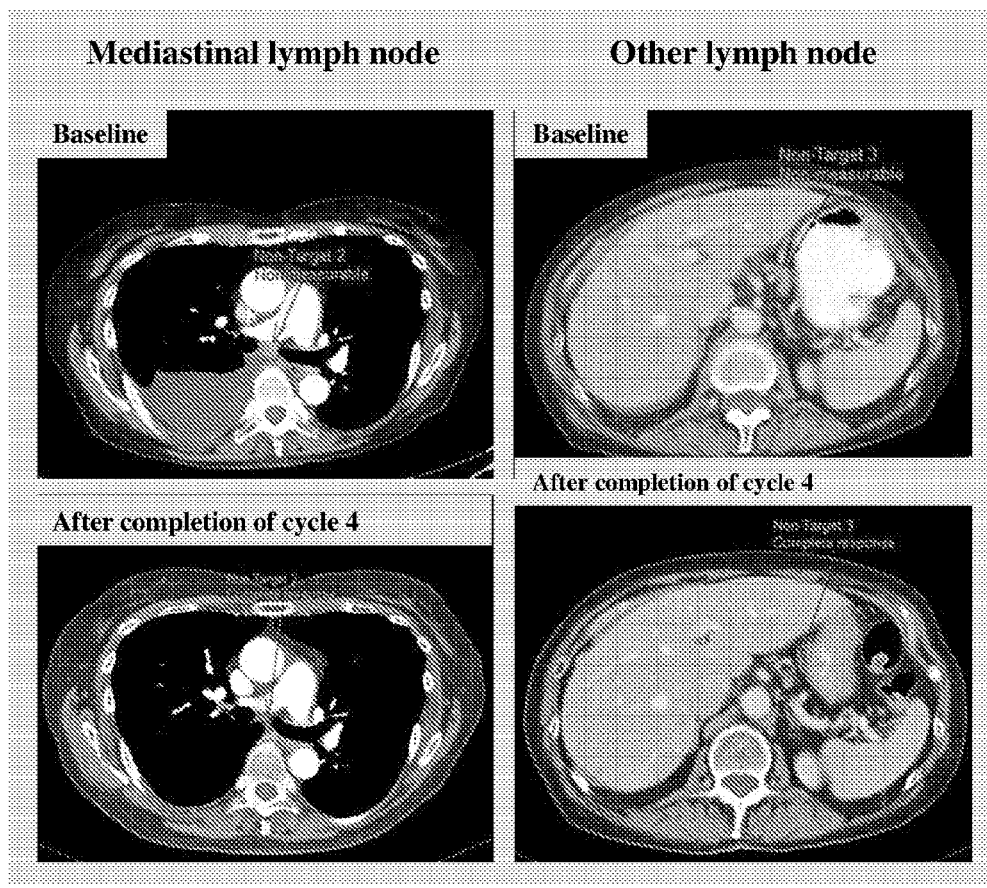
FIG. 10 shows radiographs of ovarian cancer before treatment (top) and after 4 cycles of treatment (bottom) with cisplatin and Compound A-2.

As shown in FIG. 10, partial response in the target region was observed in an ovarian cancer subject having BRCA2 germline mutation (W2626Q), where the patient received CIS 75 mg/m$^2$ on day 1 and Compound A-2 140 mg/m$^2$ on days 2 and 9 in cycle 1, and CIS 60 mg/m$^2$ in cycyle 2 due to AE. Prior to the treatment with Compound A-2, the subject received the following treatments:
(i) debulking and paclitaxel with carboplatin;
(ii) carboplatin and doxorubicin: platinum resistant;
(iii) paclitaxel and bevacizumab; and
(iv) olaparib: no response.

Figure 11:
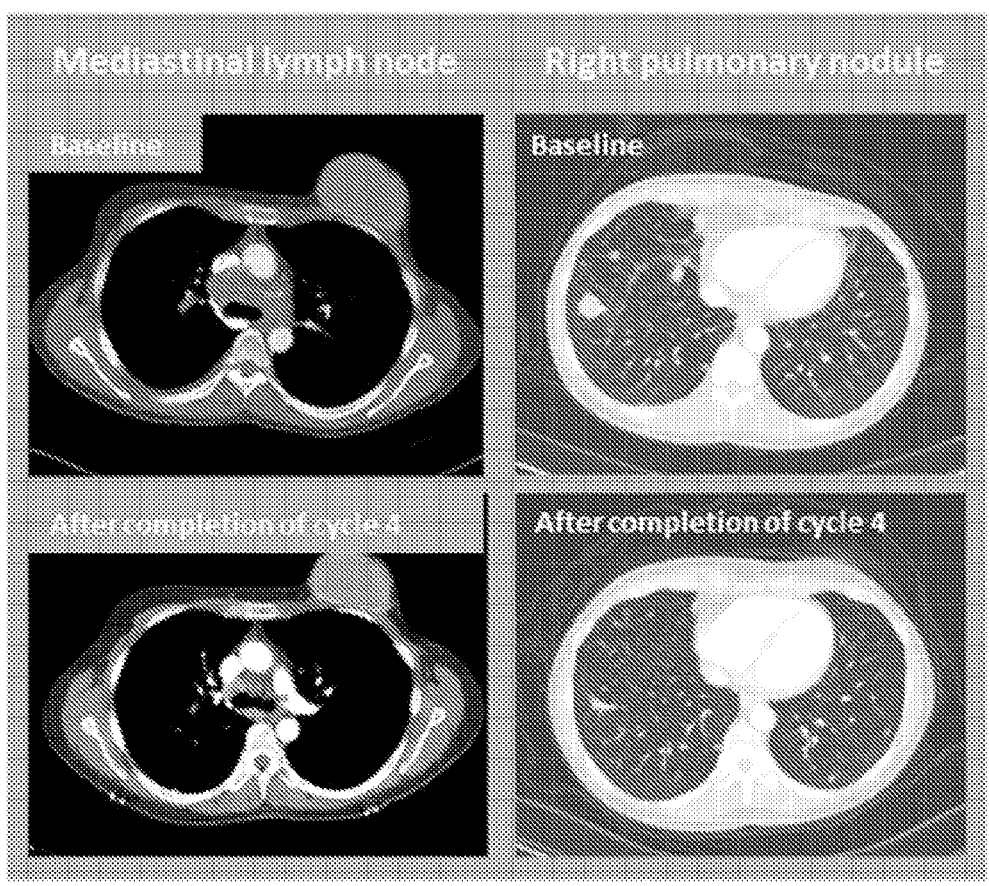
FIG. 11 shows radiographs of breast cancer before treatment (top) and after 4 cycles of treatment (bottom) with cisplatin and Compound A-2.

As shown in FIG. 11, partial response in the target region was observed in a triple-negative breast cancer subject having mutations in TP53 (R213*) and RB1 (deletion of exons 25-26), where the patient received CIS 75 mg/m$^2$ on day 1 and Compound A-2 140 mg/m$^2$ on days 2 and 9 in cycle 1. New brain metastases and leptomeningeal disease were discovered after completion of cycle 4, but no follow-up brain images are shown here as no brain imaging performed at the baseline. The subject Prior to the treatment with Compound A-2, the subject received the following treatments:
(i) mastectomy; doxorubicin, cyclophosphamide, paclitaxel; and radiation: progressive disease PD) after 17 months;
(ii) re-excision; gemcitabine and ciaplatin: PD after 3 months; and
(iii) certain investigation agent: PD after 6 weeks.

Example 8. Phase I Trial of First-in-Class Ataxia Telangiectasia-Mutated and Rad3-Related (ATR) Inhibitor a Compound of Formula A-2 in Combination with Gemcitabine (Gem) in Patients (Pts) with Advanced Solid Tumors In this Example, patients (pts), with advanced solid tumors measurable by RECIST 1.1 received IV a compound of Formula A-2 (Compound A-2) in combination with gem in a 3+3 dose-escalation design. Gem was administered on days 1 and 8 and Compound A-2 on days 2 and 9 of each 21-day cycle. Dose escalation was permitted if no dose-limiting toxicities (DLTs) were reported in a given treatment cycle. Fifty (50) pts (28 males and 22 females) of median age, 62 yrs (range 28-79 yrs), with Eastern Cooperative Oncology Group (ECOG) performance status 0/1: 15/35 were treated. Primary tumors included non-small cell lung (NSCLC; n=6), pancreatic (n=2), breast (n=4), colorectal (n=15), head and neck (n=1), and other/missing (n=22). The following table describes the dosage levels (DLs) and various parameters for the various treatment cohorts.
Dose levels (DLs) were:

| DL | Compound A-2 dose (mg/m$^2$) | Gem dose (mg/m$^2$) | No. pts treated |
| --- | --- | --- | --- |
| 1 | 18 | 875 | 3 |
| 2 | 36 | 875 | 3 |
| 3 | 60 | 875 | 4 |
| 4 | 72 | 875 | 7 |
| 5 | 90 | 500 | 6 |
| 6 | 140 | 500 | 8 |
| 7 | 210 | 500 | 3 |
| 8 | 210 | 750 | 3 |
| 9 | 210 | 875 | 7 |
| 10 | 210 | 1000 | 6 |

Figure 16:
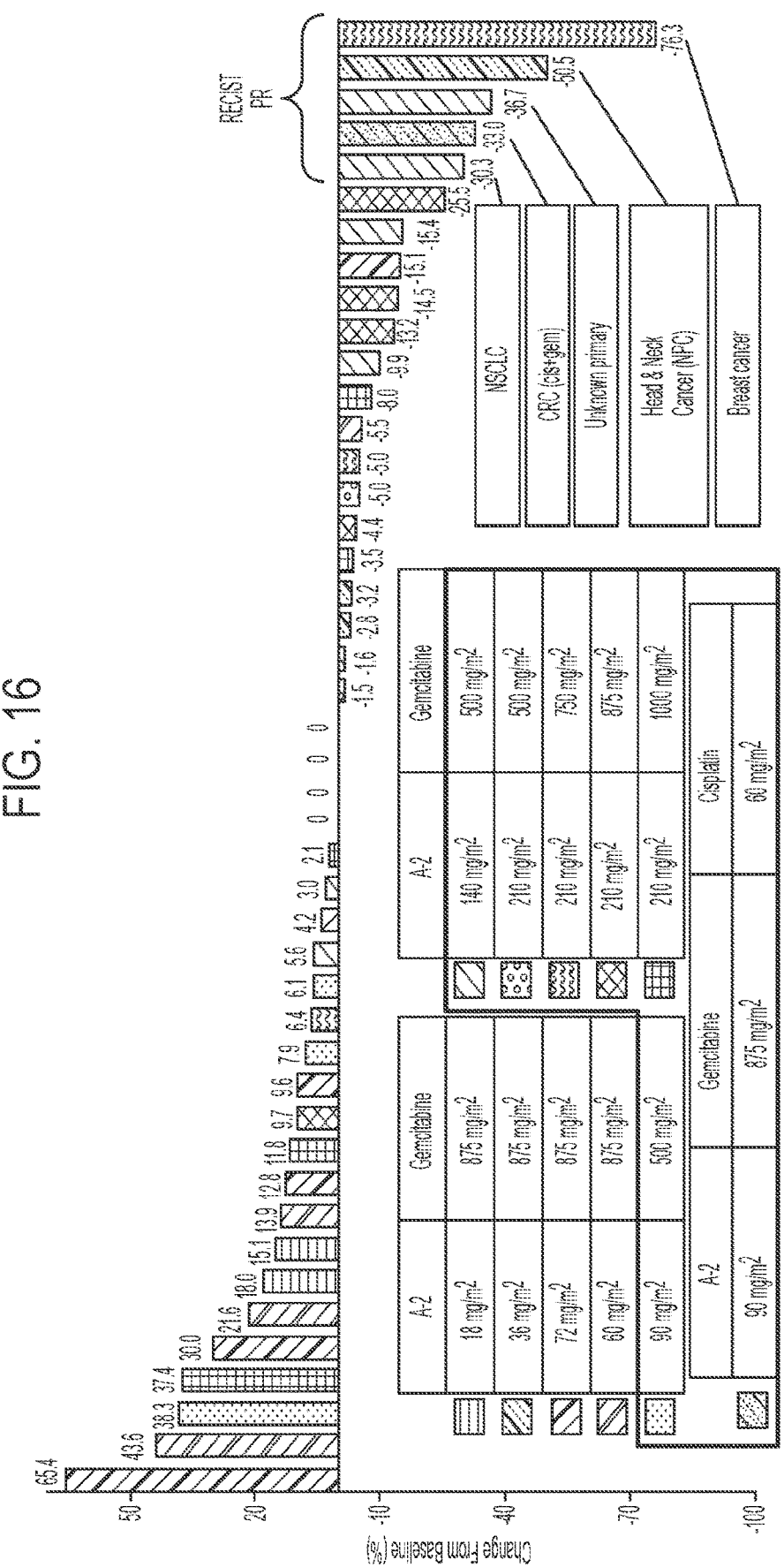
FIG. 16 shows tumor response showing changes from baseline in cancer subjects who received treatment of Compound A-2 and gemcitabine, and treatment of Compound A-2, gemcitabine, and cisplatin.
Figure 17:
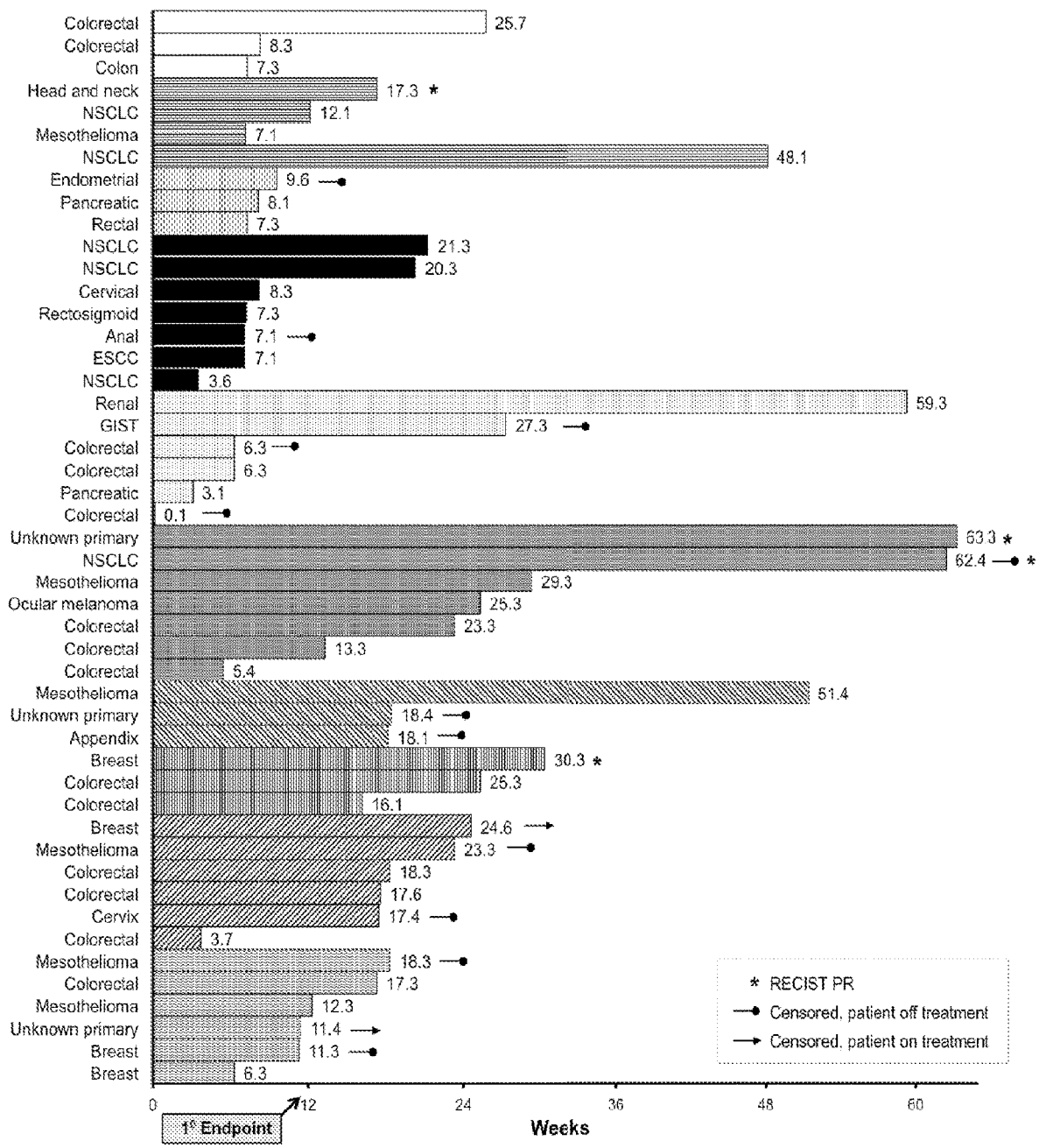
FIG. 17 shows duration of progression-free survival (PFS) from start of treatments of Compound A-2 and gemcitabine in subjects having cancer.

Grade 3/4 treatment-related adverse events (AEs) occurred in 25 pts. DLTs occurred in 4 pts: 2 pts in DL4 (grade 3 thrombocytopenia; grade 3 elevated ALT and fatigue); 1 pt in DL5 (grade 3 elevated AST); 1 pt in DL6, (grade 3 elevated AST, ALT and grade 2 elevated ALP). The maximum tolerated dose was not reached but dose escalation was stopped at DL10 per investigator recommendation. The Compound A-2 exposure was relatively linear based on $C_{max}$ and $AUC_{0-\infty}$ with the terminal elimination half-life of about 16 hours across DLs. No cumulative toxicity was observed. The best overall response was a partial response (PR) in 4 pts. The primary tumors in these four patients were breast cancer, head and neck cancer, NSCLC, and carcinoma of unknown primary origin. A pt with breast cancer in DL8 achieved PR at the 1st assessment and the pt remains on trial >133 days. Two (2) pts had prolonged stable disease (SD) responses. The tumor response and duration of progression free survival (PFS) are shown in FIGS. 16 and 17, respectively. For many patients, the duration of PFS extended beyond the 12-week primary endpoint. The median PFS was 8.3 weeks in patients treated at doses of Compound A-2<90 mg/m² in combination with gemcitabine 875 mg/m². Median PFS was 29.3 weeks in patients treated at doses of Compound A-2≥90 mg/m² in combination with gemcitabine 500 mg/m². Progression-free survival (PFS) of 415 days in 1 patient with renal cancer (papillary carcinoma) and >191 days (pt with GIST) were observed. Based on the above data, the recommended Phase II doses of Compound A-2 is 210 mg/m² and gem is 1000 mg/m².

Conclusion

Compound A-2 is well tolerated as monotherapy and in combination with CP, CIS, or gem with preliminary evidence of target modulation and antitumor activity. Compound A-2 will be further explored in early Phase II studies; in multiple tumor types, including triple-negative breast cancer and non-small cell lung cancer; and in patients with DDR aberrations.

Example 9: Phase I Dose Escalation Study of First-in-Class Ataxia Telangiectasia-Mutated and Rad3-Related (ATR) Inhibitor a Compound of Formula A-2 in Combination with Gemcitabine (Gem) and Cisplatin (CP) in Patients (Pts) with Advanced Solid Tumors In this Example, patients (pts) with advanced solid tumors received IV a compound of Formula A-2 (Compound A-2) in combination with gem and CP in a 3+3 dose-escalation design. Compound A-2 was administered days 2, 9, and 16 every 3 weeks; gem was administered days 1 and 8 every 3 weeks, and CP was administered on day 1 every 3 weeks. The following table describes the dosage levels (DLs) and various parameters for the various treatment cohorts. The tumor response is shown in FIG. 16.

| Cohort | Compound A-2 Dose (mg/m²) | Gemcitabine Dose (mg/m²) | Cisplatin Dose (mg/m²) | No. of Patients Treated/DLT Evaluable | No. of Patients with DLTs (DLT) |
|---|---|---|---|---|---|
| 11 | 90 | 875 | 60 | 6/6 | 1 (thrombocytopenia/neutropenia) |
| 12 | 120 | 875 | 60 | 2/2 | 2 (febrile neutropenia/thrombocytopenia, hypoxia/neutropenia) |

Other Embodiments

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example here.

What is claimed is:

1. A method of treating a proliferative disorder in a subject, the method comprising: administering to a subject in need thereof a platinating agent selected from the group consisting of cisplatin, oxaliplatin, carboplatin, nedaplatin, Lobaplatin, triplatin tetranitrate, picoplatin, satraplatin, ProLindac, and aroplatin, and between about 12 and about 48 hours later administering to the subject at least a first dose of a compound that inhibits ATR protein kinase, wherein the compound that inhibits ATR protein kinase is:

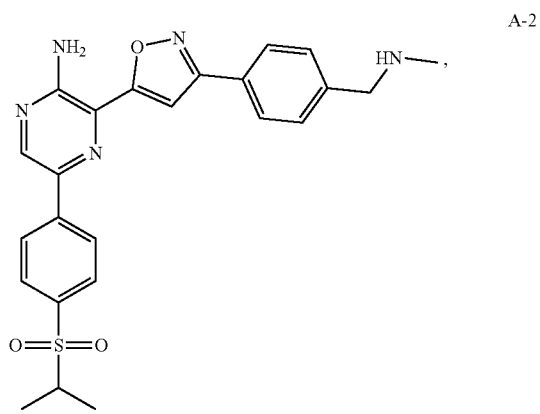 [SMILES: CNCc1ccc(-c2cc(-c3nc(-c4ccc(S(=O)(=O)C(C)C)cc4)cnc3N)on2)cc1]

A-2 or a pharmaceutically acceptable salt thereof;
wherein the subject is refractory to a treatment with the platinating agent or wherein the subject is resistant to a treatment with the platinating agent;
and wherein the proliferative disorder is a cancer selected from non-small cell lung cancer, colorectal cancer, breast cancer, and ovarian cancer.

2. The method of claim 1, wherein the compound that inhibits ATR is administered between about 18 and about 42 hours after administration of the platinating agent.

3. The method of claim 2, wherein the compound that inhibits ATR is administered between about 20 and about 40 hours after administration of the platinating agent.

4. The method of claim 1, wherein the compound that inhibits ATR is administered between about 12 and about 36 hours after administration of the platinating agent.

5. The method of claim 4, wherein the compound that inhibits ATR is administered between about 18 and about 36 hours after administration of the platinating agent.

6. The method of claim 5, wherein the compound that inhibits ATR is administered between about 20 and about 28 hours after administration of the platinating agent.

7. The method of claim 6, wherein the compound that inhibits ATR is administered about 24 hours after administration of the platinating agent.

8. The method of claim 1, wherein the cancer has a P53 Y220C missense mutation or a P53 R213* mutation.

9. The method of claim 1, further comprising administering to the subject in need thereof a second dose of the compound that inhibits ATR protein kinase between about 6 to about 9 days after administering the first dose of the compound.

10. The method of claim 9, wherein the platinating agent is administered on day 1.

11. The method of claim 9, wherein the first dose is administered on day 2.

12. The method of claim 9, wherein the second dose is administered on day 9.

13. The method of claim 1, wherein the platinating agent is selected from the group consisting of Cisplatin and Carboplatin.

14. The method of claim 1, wherein the cancer is ovarian cancer.

* * * * *